United States Patent
Hamilton et al.

(10) Patent No.: US 7,405,202 B2
(45) Date of Patent: Jul. 29, 2008

(54) CRISP POLYPEPTIDES AS CONTRACEPTIVES AND INHIBITORS OF SPERM CAPACITATION

(75) Inventors: David W. Hamilton, Edina, MN (US); Kenneth P. Roberts, St. Paul, MN (US); Kathy M. Ensrud, Roseville, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 76 days.

(21) Appl. No.: 10/515,868

(22) PCT Filed: May 28, 2003

(86) PCT No.: PCT/US03/16669

§ 371 (c)(1), (2), (4) Date: May 23, 2005

(87) PCT Pub. No.: WO03/100025

PCT Pub. Date: Dec. 4, 2003

(65) Prior Publication Data

US 2005/0282729 A1    Dec. 22, 2005

Related U.S. Application Data

(60) Provisional application No. 60/383,628, filed on May 28, 2002.

(51) Int. Cl.
*A61K 38/00* (2006.01)
(52) U.S. Cl. .......................................... 514/12; 530/350
(58) Field of Classification Search ................. None
See application file for complete search history.

(56) References Cited

U.S. PATENT DOCUMENTS

| | | | |
|---|---|---|---|
| 5,250,417 A | 10/1993 | Feuchter et al. |
| 5,565,197 A | 10/1996 | Allen |
| 5,569,581 A | 10/1996 | Killian et al. |
| 5,660,997 A | 8/1997 | Spaulding |
| 5,707,829 A | 1/1998 | Jacobs et al. |
| 5,718,896 A | 2/1998 | Allen |
| 5,723,305 A | 3/1998 | Sullivan et al. |
| 5,756,681 A | 5/1998 | Neurath et al. |
| 5,851,817 A | 12/1998 | Hardy et al. |
| 5,910,568 A | 6/1999 | Hammerstedt et al. |
| 5,969,093 A | 10/1999 | Jacobs et al. |
| 5,989,549 A | 11/1999 | Sullivan et al. |
| 6,011,013 A | 1/2000 | Carr et al. |
| 6,045,786 A | 4/2000 | Cone et al. |
| 6,051,603 A | 4/2000 | D'Cruz et al. |
| 6,083,940 A | 7/2000 | Tanabe et al. |
| 6,159,934 A | 12/2000 | Pescovitz |
| 6,166,178 A | 12/2000 | Cech et al. |
| 6,177,475 B1 | 1/2001 | Tatarintsev et al. |
| 6,180,682 B1 | 1/2001 | Place |
| 6,191,120 B1 | 2/2001 | D'Cruz et al. |
| 6,197,940 B1 | 3/2001 | Klinefelter |
| 6,231,862 B1 | 5/2001 | Majunder et al. |
| 6,235,708 B1 | 5/2001 | Holloway et al. |
| 6,245,529 B1 | 6/2001 | Holloway et al. |
| 6,251,671 B1 | 6/2001 | Hogan et al. |
| 6,258,364 B1 | 7/2001 | Herr et al. |
| 6,306,823 B1 | 10/2001 | Majumder et al. |
| 6,319,947 B1 | 11/2001 | D'Cruz et al. |
| 6,337,348 B1 | 1/2002 | Uckun et al. |
| 6,344,442 B2 | 2/2002 | Habenicht et al. |
| 6,350,736 B1 | 2/2002 | Uckun et al. |
| 6,355,235 B1 | 3/2002 | Cone et al. |
| 2002/0004479 A1 | 1/2002 | Habenicht et al. |
| 2002/0058309 A1 | 5/2002 | Baker et al. |
| 2002/0164368 A1 | 11/2002 | Zimmerman |

FOREIGN PATENT DOCUMENTS

| | | |
|---|---|---|
| EP | 1006125 | 6/2000 |
| GB | 974910 | 11/1964 |
| JP | 11279197 | 10/1999 |
| WO | 97 27218 | 7/1997 |
| WO | 99 54354 | 10/1999 |
| WO | 99 57267 | 11/1999 |
| WO | 0031264 | 6/2000 |
| WO | 01/31343 A | 5/2001 |
| WO | 01/66747 A | 9/2001 |
| WO | 0200001 | 1/2002 |
| WO | 02 14348 | 2/2002 |
| WO | 03100025 | 12/2003 |

OTHER PUBLICATIONS

Schwidetzky et al., "Isolation and characterization of the androgen-dependent mouse cysteine-rich secretory protein-3 (Crisp-3) gene", Biochem. J. 309: 831-836 (1995).*

(Continued)

*Primary Examiner*—Robert B. Mondesi
*Assistant Examiner*—Anand U Desai
(74) *Attorney, Agent, or Firm*—Mueting Raasch & Gebhardt, P.A.

(57) ABSTRACT

Included in the present invention are methods of inhibiting sperm capacitation, inhibiting the phosphorylation of a protein at tyrosine residues, inhibiting an acrosomal reaction, and inhibiting fertilization of an egg by sperm with the administration of a CRISP polypeptide.

3 Claims, 18 Drawing Sheets

OTHER PUBLICATIONS

Figure 1:
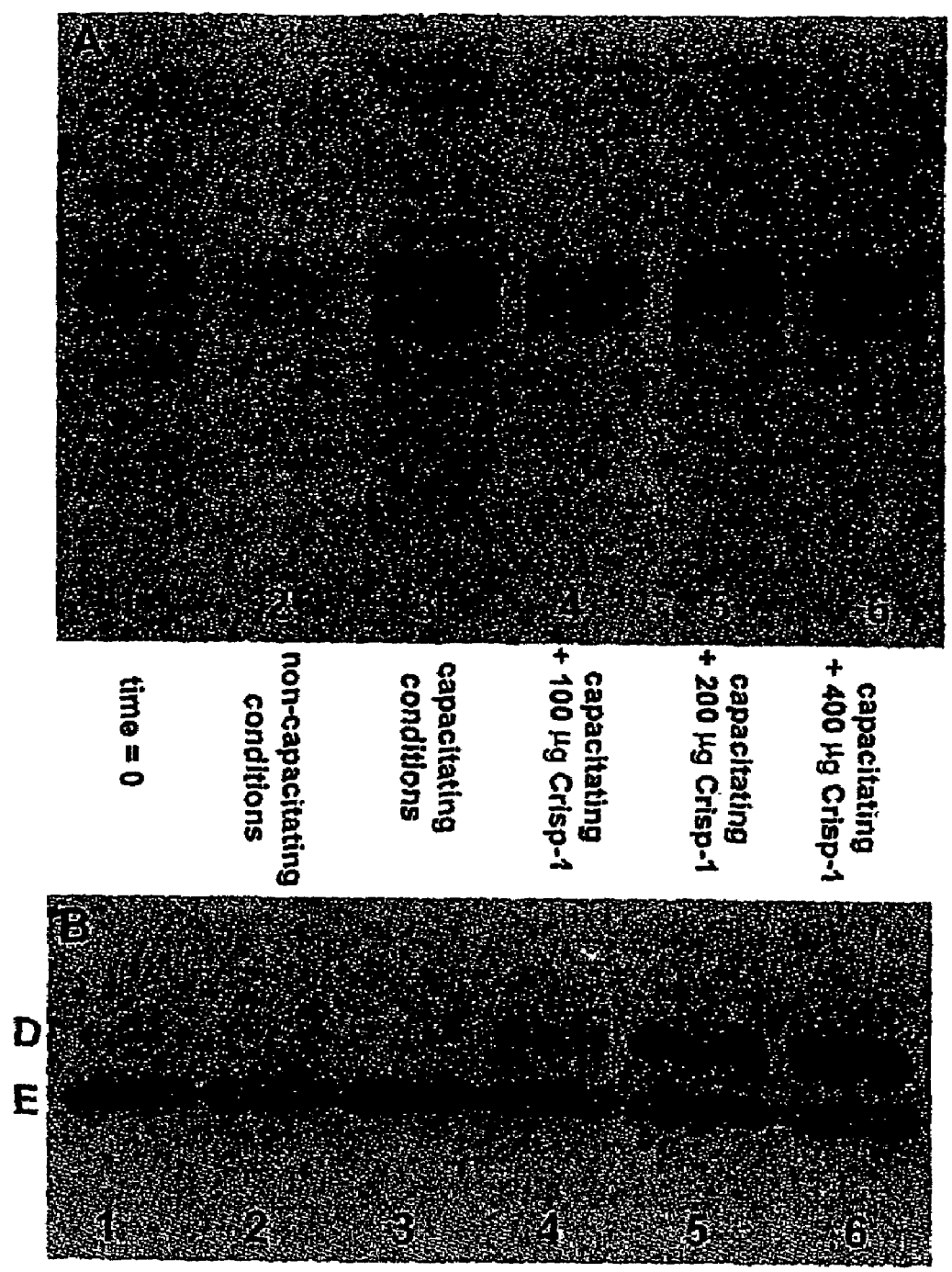

Martinez et al., "Potential contraceptive use of epididymal proteins: evidence for the participation of specific antibodies against rat epididymal protein DE in male and female fertility inhibition", Journal of Reproductive Immunology 29: 31-45 (1995).*

Nixon et al., "The identification of mouse sperm-surface-associated proteins and characterization of their ability to act as decapacitation factors", Biology of Reproduction 74: 275-287 (2006).*

Aonumo et al., "Studies on Sperm Capacitation. Characterization of Decapacitation Factor from Guinea-pig Spermatozoa," *Chem Pharm Bull* (Tokyo) 1976, 24:907-911.

Austin, "Observations on the Penetration of the Sperm into the Mammalian Egg," *Australian Journal of Scientific Research*, B 1951, 4:581-589.

Bedford, "Sperm Capacitation and Fertilization in Mammals," *Biol Reprod* 1970, 2:Supp 2:128-158.

Bendahmane et al., "Assessment of acrosomal status in rat spermatoza: studies on carbohydrate and non-carbohydrate agonists," *Arch Biochem Biophys* 2002, 404:38-47.

Biggers et al., "The Culture of Mouse Embryos in Vitro," *Methods in Mammalian Embryology* 1971, 86-116.

Bligh et al., "A Rapid Method of Total Lipid Extraction and Purification," *Canadian Journal of Biochemistry and Physiology* 1959, 37:911-917.

Boue et al., "Surface Localization of P34H, an Epididymal Protein, during Maturation, Capacitation, and Acrosome Reaction of Human Spermatozoa," *Biol Reprod* 1996, 54:1009-1017.

Brietbart, "Intracellular calcium regulation in sperm capacitation and acrosomal reaction," *Mol Cell Endocrinol* 2002, 187:139-144.

Brooks et al., "Molecular cloning of the cDNA for androgen-dependent sperm-coating glycoproteins secreted by the rat epididymis," *Eur. J. Biochem* 1986, 161(1):13-18.

Brooks et al., "Characterization and androgen-dependence of proteins associated with luminal fluid and spermatozoa in the rat epididymis," *Journal of Reproduction & Fertility* 1980, 59:363-375.

Brooks et al., "Localization of epididymal secretory proteins on rat spermatozoa," *Journal of Reproduction & Fertility* 1983, 69:651-657.

Cameo et al., "Androgen-Controlled Specific Proteins in Rat Epididymis," *Journal of Endocrinology* 1976, 69:47-55.

Chang, "Fertilizing Capacity of Spermatozoa deposited into the Fallopian Tubes," *Nature* 1951, 168:697-698.

Charest et al., "Molecular Cloning of Complementary Deoxyribonucleic Acid for an Androgen-Regulated Epididymal Protein: Sequence Homology with Metalloproteins," *Mol. Endocrinol.* 1988, 2(10):999-1004.

Choi et al., "Cyclodextrin Removes Cholesterol from Mouse Sperm and Induces Capactitation in a Protein-Free Medium," *Biol Reprod* 1998, 59:1328-1333.

Cohen et al., "Mammalian sperm-egg fusion: the development of rat oolemma fusibility during oogenesis involves the appearance of binding sites for sperm protein "DE"," *Biol Reprod.*, Jul. 1996, 55(1):202-206.

Cohen et al., "Relationship between the association of rat epididymal protein "DE" with spermatozoa and the behavior and function of the protein", *Molecular Reproduction and Development*, 2000, 56:180-188.

Cohen et al., "Mammalian sperm-egg fusion: evidence that epididymal protein DE plays a role in mouse gamete fusion", *Biol Reprod.*, Aug. 2000, 63(2):462-468.

Cohen et al., "Evidence that human epididymal protein ARP plays a role in gamete fusion through complementary sites on the surface of the human egg", *Biol Reprod.*, Oct. 2001, 65(4):1000-1005.

Cuasnicu et al., "Antibodies against epididymal glycoproteins block fertilizing ability in rat", *Journal of Reproduction & Fertility*, 1984, 72:467-471.

Cuasnicu et al., "Molecular Mechanisms Involved in Mammalian Gamete Fusion", *Arch Med Res*, Nov.-Dec. 2001, 32(6):614-618.

Davis. "Timing of fertilization in mammals: Sperm cholesterol/phospholipid ratio as a determinant of the capacitation interval," *Proc Natl Acad Sci USA*. 1981, 78:7560-7564.

Davis, "Influence of Serum Albumin on the Fertilizing Ability In Vitro of Rat Spermatozoa (39182)," *Proc Soc Exp Biol Med* 1976, 151:240-243.

Davis et al., "Studies on the mechanism of capacitation: Albumin-mediated changes in plasma membrane lipids during in vitro incubation of rat sperm cells," *Proc Natl Acad Sci USA*.1980, 77:1546-1550.

Dorval et al., "Regulation of the Phosphotyrosine Content of Human Sperm Proteins by Intracellular $Ca^{2+}$: Role of $CA^{2+}$-Adenosine Triphosphatases," *Biol Reprod* 2002, 67:1538-1545.

Eberspaecher et al., "Mouse androgen-dependent epididymal glycoprotein CRISP-1 (DE, AEG): isolation, biochemical characterization, and expression in recombinant form", *Mol. Reprod. Dev.* 1995, 42:157-172.

Ellerman et al., "Potential contraceptive use of epididymal proteins: immunization of male rats with epididymal protein DE inhibits sperm fusion ability", *Biol Reprod*., 1998, 59:1029-1036.

Eng et al., "Rabbit Sperm Reversible Decapacitation by Membrane Stabilization with a Highly Purified Glycoprotein from Seminal Plasma," *Biol Reprod* 1978, 19:1083-1094.

Evans, "Sperm disintegrins, egg integrins, and other cell adhesion molecules of mammalian gamete plasma membrane interactions", *Front in Biosci*, Jan. 15, 1999;4:d114-131.

Evans, "The molecular basis of sperm-oocyte membrane interactions during mammalian fertilization" *Human Reproduction Update*, 2002, 8(4):297-311.

Faye et al., "Purification, Radioimmunoassay, and Immunohistochemical Localization of a Glycoprotein Produced by the Rat Epididymis," *Biol Reprod* 1980, 23:423-432.

Flesch et al., "Bicarbonate stimulated phospholipid scrambling induces cholesterol redistribution and enables cholesterol depletion in the sperm plasma membrane," *J Cell Sci* 2001, 114:3543-3555.

Flesch, et al., "Dynamics of the mammalian sperm plasma membrane in the process of fertilization", *Biochimica et Biophysica Acta 1469*, 2000, 197-235.

Gadella et al., "Glycolipid migration from the apical to the equatorial subdomains of the sperm head plasma membrane precedes the acrosome reaction; Evidence for a primary capacitation event in boar spermatozoa," *J Cell Sci* 1995, 108 (Pt 3):935-946.

Giannini et al., "The Ryanodine Receptor/Calcium Channel Genes are Widely and Differentially Expressed in Murine Brain and Peripheral Tissues," *Journal of Cell Biology*.1995, 128:893-904.

Haendler et al., "Transcripts for cysteine-rich secretory protein-1 (CRISP-1); DE/AEG) and the novel related CRISP-3 are expressed under androgen control in the mouse salivary gland," *Endocrinology* 1993, 133(1):192-198.

Hall et al., "Purification and Characterization of Protein D/E, A Putative Sperm-Binding Protein Involved in Fertilization," *Prep. Biochem. Biotechnol.* 1997, 27(4):239-251.

Hayashi, M. "Analysis of the human acidic epididymal glycoprotein-like molecule: isolation of cDNA and tissue localization,". *Hokkaido Igaku Zasshi 70* 1995, (5),743-753.

Hayashi et al. "Characterization of a Human Glycoprotein with a Potential Role in Sperm-Egg Fusion: cDNA Cloning, Immunohistochemical Localization, and Chromosomal Assignment of the Gene (AEGL1)," *Genomics* 1996, 32:367-374.

Honda et al., "A Mouse Serine Protease TESPS Is Selectively Included into Lipid Rafts of Sperm Membrane Presumably as a Glycosylphosphatidylinositol-anchored Protein," *J Biol Chem*. 2002, 277:16976-16984.

Huang et al., "A Seminal Vesicle Autoantigen of Mouse is able to Suppress Sperm Capacitation-Related Events Stimulated by Sperm Albumin," *Biol Reprod* 2000, 63:1562-1566.

Huang et al., "Seminal vesicle autoantigen, a novel phospholipid-binding protein secreted from luminal epithelium of mouse seminal vesicle, exhibits the ability to suppress mouse sperm motility," *Biochem J* 1999, 343 Pt 1:241-248.

Iusem et al., "Identification of a Major Secretory Glycoprotein from Rat Epididymis: Interaction with Spermatozoa," *Biol Reprod* 1989, 40:307-316.

Kanwar et al., "Effects of Human Seminal Plasma on Fertilizing Capacity of Human Spermatozoa," *Fertil Steril* 1979, 31:321-327.

Kim et al., "Differential release of guinea pig sperm acrosomal components during exocytosis", *Biol Reprod.*, Jan. 2001, 64(1):148-156.

Klemme et al., "Cloning and characterization of the rat *Crisp-1* gene", *Gene*, Nov. 29, 1999 240(2):279-288.

Kohane et al., "Interaction of proteins of epidiymal origin with spermatozoa", *Biol Reprod.*, Nov. 1980, 23(4):737-742.

Kratzschmar et al., "The Human Cysteine-Rich Secretory Protein (CRISP) Family. Primary Structure and Tissue Distribution of CRISP-1, CRISP-2 and CRISP-3", *Eur. J. Biochem.* Mar. 15, 1996 236(3):827-836.

Laemmli,"Cleavage of Structural Proteins during the Assembly of the Head of Bacteriophage T4," *Nature* 1970, 227:680-685.

Luo et al.,"A Novel Heat-labile Phospholipid-binding Protein, SVS VII, in Mouse Seminal Vesicle as a Sperm Motility Enhancer," *J Biol Chem* 2001, 276:6913-6921.

Manco et al., "A Major Secretory Protein From Rat Seminal Vesicle Binds Ejaculated Spermatozoa," *Gamete Res* 1988; 21:71-84.

Manco et al., "Detection of sperm-coating antigens immunologically related to a seminal protein in rat," *Eur J Cell Biol* 1988, 47:270-274.

Moore et al., "Rat Epididymis-Specific Sperm Maturation Antigens. 1. Evidence that the 26 kD 4E9 Antigen Found on Rat Caudal Epididymal Sperm Tail is Derived from a Protein Secreted by the Epididymis," *Molecular Reproduction & Development* 1994, 37:181-194.

Moore, "Glycoprotein Secretions of the Epididymis in the Rabbit and Hamster: Localization on Epididymal Spermatozoa and the Effect of Specific Antibodies on Fertilization in Vivo," *Exp Zool* 1981, 215:77-85.

Morrissette et al., "Primary Structure and Properties of Helothermine, a Peptide Toxin that Blocks Ryanodine Receptors," *Biophysical Journal* 1995, 68:2280-2288.

National Center for Biotechnology Information, National Library of Medicine, National Institutes of Health, GenBank *Accession No. AAD41529* "acidic epididymal glycoprotein D/E (*Rattus norvegicus*)." Retrieved from the Internet. <URL.

National Center for Biotechnology Information, National Library of Medicine, National Institutes of Health, *GenBank Accession No. AH007912* "*Rattus norvegicus* Egi: 5305209." GenBank RNCRISP01-RNCRISP12, Accession No. U60949-60960. Retrieved from the Internet: <URL.

National Center for Biotechnology Information, National Library of Medicine, National Institutes of Health, *GenBank Accession No. A49202*, "cysteine-rich secretory protein-1—mouse". Retrieved from the Internet: <URL.

National Center for Biotechnology Information, National Library of Medicine, National Institutes of Health, *GenBank Accession No. NP 001122*, "acidic epididymal glycoprotein-like 1 (*Home sapiens*)". Retrieved from the Internet: <URL.

National Center for Biotechnology Information, National Library of Medicine, National Institutes of Health, *GenBank Accession No. CAA64524*, "cysteine-rich secretory protein-1 (*Homo sapiens*)". Retireved from the Internet: <URL.

National Center for Biotechnology Information, National Library of Medicine, National Institutes of Health, *GenBank Accession No. L05559* "Mouse cysteine-rich secretory protein-1 mRNA, complete cds." Retrieved from the Internet: <URL.

National Center for Biotechnology Information, National Library of Medicine, National Institutes of Health, *GenBank Accession No. X95237* "*H. sapiens* mRNAS for cysteine-rich secretory protein-1." Retrieved from the Internet: <URL.

National Center for Biotechnology Information, National Library of Medicine, National Institutes of Health, *GenBank Accession No. P16562*, "Testis-specific protein TPX-1 precursor (Cysteine-rich secretory protein-2) (CRISP-2)." Retrieved from the Internet: <URL.

National Center for Biotechnology Information, National Library of Medicine, National Institutes of Health, *GenBank Accession No. NP 033769*, "acidic epididymal glycoprotein 2 (*Mus musculus*)." Retrieved from the Internet: <URL.

National Center for Biotechnology Information, National Library of Medicine, National Institutes of Health, *GenBank Accession No. AAD48090.* "Cysteine-rich secretory protein-2 CRISP-2; TPX-1 (*Rattus norvegicus*)" Retrieved from the Internet: <URL.

National Center for Biotechnology Information, National Library of Medicine, National Institutes of Health, *GenBank Accession No. P54108.* "Cysteine-rich secretory protein-3 precursor (CRISP-3) (SGP28 protein)". Retrieved from the Internet: <URL.

National Center for Biotechnology Information, National Library of Medicine, National Institutes of Health, *GenBank Accession No. Q03402.* Sperm-coating glycoprotein 2 precursor (SCP 2) (Acidic epididymal glycoprotein 2) (Cysteine-rich secretory protein-3) (Crisp-3). Retrieved from the Internet: <URL.

National Center for Biotechnology Information, National Library of Medicine, National Institutes of Health, *GenBank Accession No. NM 22859.* "*Rattus norvegicus* epididymal glycoprotein (Aerg), mRNA." Retrieved from the Internet: <URL.

National Center for Biotechnology Information, National Library of Medicine, National Institutes of Health, *GenBank Accession No. X95239.* "*H.sapiens* mRNA for cysteine-rich secretory protein-2/type I." Retrieved from the Internet: <URL.

National Center for Biotechnology Information, National Library of Medicine, National Institutes of Health, *GenBank Accession No. AF078552.* "*Rattus norvegicus* cysteine-rich secretory protein-2 CRISP-2 (tpx-1) mRNA, complete cds." Retrieved from the Internet: <URL.

National Center for Biotechnology Information, National Library of Medicine, National Institutes of Health, *GenBank Accession No. X95240.* "*H. sapiens* mRNA for cysteine-rich secretory protein-3." Retrieved from the Internet: <URL.

National Center for Biotechnology Information, National Library of Medicine, National Institutes of Health, *GenBank Accession No. L05560.* "Mouse cysteine-rich secretory protein-3 mRNA, complete cds." Retrieved from the Internet: <URL.

O'Bryan et al.,"Identification of a Rat Testis-Specific Gene Encoding a Potential Rat Outer Dense Fibre Protein," *Mol. Reprod. Dev.* 1998; 50(3):313-322.

Olson et al., "Allurin, a 21-kDa sperm chemoattractant from *Xenopus* egg jelly, is related to mammalian sperm-binding proteins", *Proc Natl Acad Sci USA*, Sep. 25, 2001, 98(20):11205-11210.

Paonessa et al., "Transglutaminase-Mediated Modifications of the Rat Sperm Surface in Vitro," *Science* 1984, 226:852-855.

Perez Martinez et al., "Potential contraceptive use of epididymal proteins: evidence for the participation of specific antibodies against rat epididymal protein DE in male and female fertility inhibition", *Journal of Reproductive Immunology*. 1995, 29:31-45.

Rankin et al., "Isolation, Immunolocalization, and Sperm-Assodication of Three Proteins of 18, 25 and 29 Kilodaltons Secreted by the Mouse Epididymis," *Biology of Reproduction* 1992, 46:747-766.

*Remington's Pharmaceutical Sciences*, 15th Edition. Copyright Page, and Table of Contents.

Roberts et al., "Expression of Crisp-1 mRNA Splice Variants in the Rat Epididymis, and Comparative Analysis of the Rat and Mouse Crisp-1 Gene Regulatory Regions", *J Androl*, Jan.-Feb. 22, 2001, 22(1):157-63.

Roberts et al., "A Comparative Analysis of Expression and Processing of the Rat Epididymal Fluid and Sperm-Bound Forms of Protein D and E," *Biology of Reproduction*. 2002, 67:525-533.

Roberts et al. "Inhibition of Capacitation-Associated Tyrosine Phosphorylation Signaling in Rat Sperm by Epididymal Protein Crisp-1," *Biol. of Reprod.* , 2003, 69:572-581.

Rochwerger et al., "Redistribution of a Rat Sperm Epididymal Glycoprotein After In Vitro and In Vivo Capacitation," *Molecular Reproduction & Development* 1992, 31:34-41.

Rochwerger et al., "Mammalian sperm-egg fusion: the rat egg has complementary sites of a sperm protein that mediates gamete fusion", *Dev Biol.*, Sep. 1992, 153(1):83-90.

Sansone et al., "Zinc-Protein From Rat Prostate Fluid Binds Epididymal Spermatozoa," *J Exp Zool* 1991, 25:379-385.

Schambony et al., "Equine CRISP-3: primary structure and expression in the male genital tract," *Biochim Biophys Acta*, Sep. 8, 1998, 1387(1-2):206-216.

Simons, "Lipid Rafts and Signal Transduction," *Nat Rev Mol Cell Biol* 2000, 1:31-39.

Sinclair et al., "Specific Expression of Soluble Adenylyl Cyclase in Male Germ Cells," *Mol Reprod Dev* 2000, 56:6-11.

Snell et al., "The Molecules of Mammalian Fertilization", *Cell*, May 1996, 31;85:629-637.

Tatusova et al., "BLAST 2 Sequences, a new tool for comparing protein and nucleotide sequences," *FEMS Microbiol. Lett.* 1999, 174:247-250.

Tezon et al., "Immunochemical Localization of Secretory Antigens in the Human Epididymis and Their Association with Spermatozoa," *Biol Reprod* 1985, 32:591-597.

Tomes et al., "Treatment of human spermatozoa with seminal plasma inhibits protein tyrosine phosphorylation," *Mol Hum Reprod* 1998, 4:17-25.

Travis et al., "Expression and Localization of Caveolin-1, and the Presence of Membrane Rafts, in Mouse and Guinea Pig Spermatozoa," *Dev Biol* 2001, 240:599-610.

Trevino et al., "Identification of mouse *trp* homologs and lipid rafts from spermatogenic cells and sperm," *FEBS Lett* 2001, 509:119-125.

Trevino et al., "Localisation of inositol trisphosphate and ryanodine receptors during mouse spermatogenesis: possible functional implications," *Zygote* 1998, 6:159-172.

Tubbs et al., "Binding of Protein D/E to the Surface of Rat Epididymal Sperm Before Ejaculation and After Deposition in the Female Reproductive Tract," *J Androl* 2002, 23:512-521.

Visconti et al., "Capacitation of Mouse Spermatozoa. I. Correlation between the capacitation state and protein tyrosine phosphorylation" *Development*; 1995, 121:1129-1137.

Visconti et al., "Capacitation of Mouse Spermatozoa. II. Protein tyrosine phosphorylation and capacitation are regulated by a cAMP-dependent pathway," *Development*; 1995, 121:1139-1150.

Visconti et al., "The Molecular Basis of Sperm Capacitation," J Androl 1998, 19:242-248.

Visconti et al., "Roles of Bicarbonate, cAMP, an Protein Tyrosine Phosphorylation on Capacitation and the Spontaneous Acrosome Reaction of Hamster Sperm," *Biol Repro*; 1999, 61:76-84.

Visconti et al., "Novel signaling pathways involved in sperm acquisition of fertilizing capacity," J Reprod Immunol 2002, 53:133-150.

Vreeburg et al., "Secretion of epididymal proteins and their interactions with spermatozoa," *Bull Assoc Anat* (Nancy). 1991, 75:171-173.

Wong et al., "Studies on the Binding of a 32K Rat Epididymal Protein to Rat Epididymal Spermatozoa," Biol Reprod 1982, 27:1239-1246.

Wuttke et al., "Bicarbonate-Regulated Soluble Adenylyl Cyclase," *JOP*, 2001, 2:154-158.

Xu et al., "Identification of the Rat Epididymis-Secreted 4E9 Antigen as Protein E: Further Biochemical Characterization of the Highly Homologous Epididymal Secretory Proteins D and E," *Mol Reprod Dev* 1996, 43:347-357.

Xu et al., "The 26 kD Protein Recognized on Rat Cauda Epididymal Sperm by Monoclonal Antibody 4E9 Has Internal Peptide Sequence That Is Identical to the Secreted Form of Epididymal Protein $E^1$," Mol Reprod Dev.1997, 46:377-382.

Yanagimachi, "Mammalian Fertilization" in *The Physiology of Reproduction*, Knobil et al., eds, Raven Press, New York, 1994, pp. 186-317.

Roberts et al., "Rat epididymal protein Crisp-1 inhibits sperm capacitation," Molecular biology of the Cell (Nov. 2002) vol. 13, No. Supplement, pp. 386A. 42nd Annual Meeting of the American Society for Cell Biology. San Francisco, CA, USA. Dec. 14-18, 2002.

Roberts et al., "Epididymal secreted protein CRISP-1 and sperm function," Molecular and Cellular Endocrinology. Epub doi:10.1016/j.mce.2005.12.034 Jan. 13, 2006. (Epub ahead of print). 6 pages.

Roberts et al., "Processing and Localization of the D and E Forms of Rat CRISP-1," International Society of Andrology. Abstract presented at The VIIth International Congress of Andrology, Montreal, Canada, Jun. 15-19, 2001. 1 page.

Nolan et al., "Identification of Rat Cysteine-Rich Secretory Protein 4 (Crisp4) as the Ortholog to Human CRISP1 and Mouse Crisp4," 2006, *Biol. Of Reprod.*, 74:984-991.

* cited by examiner

```
meikhllflv aaacllpmls mkkksardqf nklvtdlpnv qeeivnihna
lrrrvvppas nmlkmswsee aaqnarifsk ycdmtesnpl errlpntfcg
enmhmtsypv swssvigvwy sestsfkhge wtttdddittt dhytqivwat
syligcaias crqqgspryl yvchychegn dpetknepyk tgvpceacps
ncedklctnp ciyydeyfdc diqvhylgcn hsttilfcka tclcdteik
```
human CRISP-1 (SEQ ID NO:1)
Accession No. CAA64524

```
almlvllfla avlppsllqd ttdewdrdle nlsttklsvq eeiinkhnql
rrtvspsgsd llrvewdhda yvnaqkwanr ciynhsplqh rtttlkcgen
lfmanypasw ssviqdwyde sldfvfgfgp kkvgvkvghy tqvvwnstfl
vacgvaec
```
rat CRISP-1 (SEQ ID NO:2)
Accession No. AAD41529

```
malmlvlffl aavlppsllq dssqenrlek lsttkmsvqe eivskhnqlr
rmvspsgsdl lkmewnydaq vnaqqwadkc tfshspielr ttnlrcgenl
fmssylasws saiqgwyney kdltydvgpk qpdsvvghyt qvvwnstfqv
acgvaecpkn plryyyvchy cpvgnyqgrl ytpytagepc ascpdhcedg
lctnscghed kytnckylkk mlscehellk kgckatclce gkih
```
mouse CRISP-1 (SEQ ID NO:3)
Accession No. A49202

```
mallpvlflv tvllpslpae gkdpaftall ttqlqvqrei vnkhnelrka
vsppasnmlk mewsrevttn aqrwankctl qhsdpedrkt strcgenlym
ssdptswssa iqswydeild fvygvgpksp navvghytql vwystyqvgc
giaycpnqds lkyyyvcqyc pagnnmnrkn tpyqqgtpca gcpddcdkgl
ctnscqyqdl lsncdslknt agcehellke kckatclcen kiy
```
human CRISP-2 (SEQ ID NO:4)
Accession No. P16562

```
mawfqvmlfv fgvllplppt egkdpdfatl ttnqiqvqre iiakhnelrr
qvsppgsnil kmewnvqaaa naqkwannci lehsstedrk inikcgenly
mstdptswrt viqswyeene nfvfgvgakp nsavghytql vwyssfkvgc
gvaycpnqdt lkyfyvchyc pmgnnvmkks tpyhqgtpca scpnncdngl
ctnscdfedl lsnceslkss arckhellka kceatclced kih
```
rat CRISP-2 (SEQ ID NO:5)
Accession No. AAD48090

FIGURE 11A

```
mtlfpvllfl vagllpsfpa nedkdpafta llttqtqvqr eivnkhnelr
ravspparnm lkmewnkeaa anaqkwanqc nyrhsnpkdr mtslkcgenl
ymssassswz qaiqswfdey ndfdfgvgpk tpnavvghyt qvvwyssylv
gcgnaycpnq kvlkyyyvcq ycpagnwanr lyvpyeqgap cascpdncdd
glctngckye dlysnckslk ltltckhqlv rdsckascnc snsiy
```
Human CRISP-3 (SEQ ID NO:6)
Accession No. P54108

```
malmlvlffl aavlppsllq dnsqenslek lstskksvqe eivskhnqlr
rkvspsgsdl lnmewnydaq vnaqqradkc tfshspielr ttnlkcgenl
fmssylvpws sviqgwynes kglifgvgpk qnvsvvghht qvvwksnlqv
acgvaecpen plryfyvcry cpvlnysghy psrpylayta rapcascpdr
cedglctksc qykdmsfwck rleyvckhpg lkkrclatcq c
```
mouse CRISP-3 (SEQ ID NO:7)
Accession No. Q03402

FIGURE 11B

Human CRISP-1 cDNA sequence (SEQ ID NO:8)
Accession Number X95237

```
gcacaaatac actacataga gaaaggcttg gttcttatca ggacacaaat
ttaaaggctg tgtggacttg gggatggaaa ttaaacacct cttgtttttg
gttgctgctg cttgcttact gcctatgttg tccatgaaaa agaaatcagc
tagagaccaa tttaataagc tcgtcaccga cttgccaaat gtacaagaag
agatcgttaa tatacacaac gccctcagga gaagagtagt tccaccagcc
agcaacatgc tgaagatgag ttggagtgaa gaggctgcac aaaatgccag
aattttttca aagtattgtg atatgacaga gagcaacccc cttgagagga
gacttccaaa tacctttgt ggagaaaata tgcatatgac atcttatcct
gtatcatggt caagtgtaat tggagtctgg tacagtgagt ctacaagttt
caaacatgga gaatggacaa caacggatga tgacataact actgaccact
acactcagat tgtttgggcc acatcttacc tgattggctg tgccattgca
tcttgccgcc aacaaggatc acctcgatat ctctacgttt gtcactattg
tcatgaggga aatgatcctg aaacaaagaa tgaaccttat aagacaggcg
tcccatgtga agcctgccca agtaactgtg aagacaaact ttgcactaac
ccctgcatct actatgatga atacttcgac tgtgacatac aagtccatta
tctgggatgc aaccactcaa caactatcct attctgtaaa gccacttgtc
tgtgtgacac tgagataaaa taggtctttg ttattttcaa ctgttctatg
ctgtgacgat gaggaggaga tgtctgttgg attcatgtct tttgctatag
ttcagtagct tctgctaaat ttcactgatt ttaatcatgc tggagacctt
aactcccatc ctgatacatc ctgaagtaac actgttttaa actttcttag
tgctggagta aaaggtcaag tccaacacct gccttaaatt taaatcatgt
gatttatagt ttttaagttg gcataattca acttatggta taactgggtc
cctcaacagt aacctgggct aaaataggtc ttatgtggtt caactcccac
ccccgccttc cccatatttt caaccactct gattatcttc cctgcacaac
taacatccag taataattct tcactttaa aatttactt ctactttaaa
tcaatcatta aaggaatcca caaagcaaac agagttcagt ctcatcttgc
aaggtaaata tcatttaatt ggaagtagtt taaatgtctc attgttttat
tgacacatct atatatacat ttgtgaagca agaaacaata aaaaagcttc
gtatgccatt aatttaacaa aatatgtatt cagtactgat tgcatacaag
atgcatgttt atatatatgg aaggaatata gtttcatttc attgcaaagg
cagtataaaa gatatataaa atagcataat atgagaaatt aagtccctaa
agacatatag gtcacatatt attattgcca gatgagcata aatagcttct
gtttggagat tcaggaaagc cttagggtgg aatgaggaac atcttctgag
taaacagggt tgcaaaggtt atgattattt caacacaatg gaagagcaca
gttaaggcca actaacgtaa aatgcactga agccttaggg aatattgaag
ggcctgacat ggggaaaggg aaggctagaa atacttggtc aaattttaac
attataccaa agttataccc agttctacct acttgtatat ttctttactc
atttcaataa agtgtttgaa aaaaaaaaa aaaaaa
```

FIGURE 12A rat CRISP-1 cDNA sequence (SEQ ID NO:9)
Accession Number NM_022859

```
aactcctcag gaagaccagc agagtcaact aacctggacc cttggtagct
cccggcgact gaatcattaa gcaaagggac aatatctcat tctgctctga
aaatagaacc atggcattaa tgttagtgct gttgttcctg gctgctgtat
tgccaccatc tcttcttcaa gataccactg atgaatggga tagagatctt
gagaatttgt caaccactaa actgtcagtc caagaagaga tcataaacaa
gcacaaccaa ttgagacgaa cggtttctcc gtctggtagt gacttactaa
gagtggaatg ggaccatgat gcttatgtga acgctcagaa atgggcaaac
aggtgcattt acaatcacag tcctctacaa cacaggacaa ccacattaaa
atgtggtgag aatttgttca tggcaaatta ccctgcatcg tggtcttctg
taatccaaga ttggtatgat gaatcccttg attttgtctt tggtttcggc
ccaaaaaaag ttggtgttaa agtcggacac tatactcagg ttgtttggaa
ttcaactttc ctggttgcat gtggagttgc tgaatgccct gaccaaccat
tgaaatactt ttatgtttgt cactattgtc ctggtggcaa ttatgtagga
agactatact caccttacac agaaggagaa ccttgtgaca gttgtcctgg
taattgtgaa gatgggctgt gcaccaatag ttgtgaatat gaagataatt
attctaactg tggcgatctg aagaagatgg tgagctgcga cgatccactt
cttaaagaag gttgcagagc ttcatgcttc tgtgaagaca aaattcatta
aatttccagt ccacataatc aggaccatgt agaaaaggaa aataccctct
acttagtctt atcatgtccc accaaaaata tgtaggttta gtacactgaa
ataattccaa atggtaaaga ttctgtttct tctcctattt ctctctattt
tgcataagtc atttacccca aaatattta aaataacaaa atcaatacca
cctttggaac tggccatatg aaatctgtga cacatttatg gaatcaaatc
tatcccacga ttatatatta tttgtctgta tgacttaagt cactaaatct
ctggcttgaa aatatgaatc atgttcccag agcacaatga aataagagaa
cagatagcat atagtccctc tgtattggcc aatcactttt tttttagttc
taccactatt tttagctaat tatctccgga gaaaacattc acattaattg
tcttctattt cttctcacca ttcattattc ttcacattca tcagaattag
tggtttaaat tctaaactac catttatgtt ttgttgtcgg gtctttaaga
atgatattaa aatgtaactt aataaacaga atttgcttgt tcaggggtaa
tgaccttggt tgcttcagaa aaaaaataaa tcttaatctt agcatatt
``` mouse CRISP-1 cDNA sequence (SEQ ID NO:10)
Accession Number L05559

```
ctcattctac tctgaagcca gcaccatggc attaatgctt gtgctgttct
tcttggctgc tgtactgccc ccatcccttc ttcaagatag ctctcaggaa
aatcgtcttg agaaactttc aaccactaaa atgtcagtcc aagaagagat
tgtaagcaag cacaaccaat tgagacgaat ggtttctcca tctggcagtg
acttactaaa aatggaatgg aactatgatg ctcaagtgaa tgctcagcaa
tgggcagaca agtgtacatt cagtcacagt cctatagaac tcaggacaac
taatttaaga tgtggggaga atttgttcat gtcatcttac cttgcatcat
ggtcttctgc aatccaagga tggtataatg aatacaaaga tcttacatat
gatgttggcc caaagcaacc tgatagtgtg gttggacatt atactcaggt
tgtttggaac tcaactttcc aagttgcatg tggagttgct gaatgcccta
aaaatccact gagatactat tatgtttgtc actattgtcc tgttggcaat
```

FIGURE 12B

```
tatcaaggaa ggctatacac accttacact gcaggagaac cgtgtgccag
ttgtcctgat cactgtgaag atgggctatg caccaatagt tgtggacatg
aagataagta tactaactgt aaatatctga agaagatgct atcctgtgaa
catgaacttc ttaaaaaagg ttgcaaagct acatgcctct gtgaaggcaa
aattcactaa atttcctgta ctcgtagcca ggaccatgta gagaaagctc
atactctcta gttaggctta tcacatccca ccaagaaagt atagatttag
gacattgaaa taattccaga tagtaaagat tctgtttctt cttctatttc
tttctatttt acagaaatca tttacsccaa atattttaaa ataacaaatt
tgataatacc tttgtacctt gacatatgaa atctgtgaca cattttcgga
gtcaagtcta gcccatgatt atacattgtc tgtatgacta aagtcactaa
aactcatatg actaatgttc caagagcaca atgaagtaaa ggaatagaaa
acatatagtt cctgtataat ggtcagtcat cttttctagc tctacctagt
ttactctctc tggagaaaat cacattaatc gtcttttatt ttctttctca
ctattcctta ttcttcaaat tcatcataat cagtggttta aattctaaac
tactatttac attttagttt tttttaaaga atgatataaa atgtacctta
acgagcagaa tttatagttt gcttgttcag gggacaatga cctttgttgc
tttagaaaaa taataaatct taatcttggc aaaaaaaaaa aaaaaaaaa
aaa
```

Human CRISP-2 cDNA sequence (SEQ ID NO:11)
Accession No. X95239

```
cggtgagagg ggcgcgcagc agcagctcct caacgccgca acgcgccggc
ccaactgcag gaaggtctgt gctctggagc cagggtaaat ggttataaaa
ttatacacca tggccctcct aaagacactc taggaaaacc atgtcatcct
gatcttaaaa cacctgcaag aaagagcaca gtacttcacc attaataaag
tagatatttc atcctgctca gaaaaccaac atttccagca atggctttac
taccggtgtt gtttctggtt actgtgctgc ttccatcttt acctgcagaa
ggaaaggatc ccgcttttac tgctttgtta accacccagt tgcaagtgca
aagggagatt gtaaataaac acaatgaact aaggaaagca gtctctccac
ctgccagtaa catgctaaag atggaatgga gcagagaggt aacaacgaat
gcccaaaggt gggcaaacaa gtgcacttta cacatagtg atccagagga
ccgcaaaacc agtacaagat gtggtgagaa tctctatatg tcaagtgacc
ctacttcctg gtcttctgca atccaaagct ggtatgacga atcctagat
tttgtctatg gtgtaggacc aaagagtccc aatgcagttg ttggacatta
tactcagctt gtttggtact cgacttacca ggtaggctgt ggaattgcct
actgtcccaa tcaagatagt ctaaaatact actatgtttg ccaatattgt
cctgctggta ataatatgaa tagaaagaat accccgtacc aacaaggaac
accttgtgcc ggttgccctg atgactgtga caaggacta tgcaccaata
gttgccagta tcaagatctc ctaagtaact gtgattcctt gaagaataca
gctggctgtg aacatgagtt actcaaggaa aagtgcaagg ctacttgcct
atgtgagaac aaaatttact gatttaccta gtgagcattg tgcaagactg
catggataag ggctgcatca tttaattgcg acataccagt ggaaattgta
tgtatgttag tgacaaattt gatttcaaag agcaatgcat cttctccccc
agatcatcac agaaatcact ttcaggcaat gatttacaaa agtagcatag
tagatgatga caactgtgaa ctctgacata aatttagtgc tttataacga
actgaatcag gttgaggatt ttgaaaactg tataaccata ggatttaggt
```

FIGURE 12C

```
        cactaggact ttggatcaaa atggtgcatt acgtatttcc tgaaacatgc
        taaagaagaa gactgtaaca tcattgccat tcctactacc tgagtttta
        cttgcataaa caataaattc aaagctttac atctgcaaaa aaaaaaaaaa
                   aaaaaa
``` rat CRISP-2 cDNA sequence (SEQ ID NO:12)
Accession No. AF078552

```
        ccggcaatga gcaggtggtt gaggtctgca gaaatagcag cagcccccat
        gctgacctct ttcctttctg acaccatgaa gacctgggct gtggagctag
        ggataaggaa aacaaacacc atgaccctca cactttaaaa gaagcatgtc
        ctcctgatct tcaaacatca gaagaaagga caagataagg cagatatttc
        aactgtcaaa tcaacactaa ctgtcaaatc aacacttcca gccatggctt
        ggttccaggt gatgctgttt gtctttggtg tnctgctacc attgccaccc
        acagaaggaa aggatccaga cttcgctact ttgacaacca accaaataca
        agttcaaaga gagatcatag ctaaacacaa tgaactgagg agacaagtta
        gcccccctgg cagcaacata ctaaaaatgg aatggaacgt acaagcagca
        gcaaatgctc aaaagtgggc taataactgt attttagaac acagtagtac
        agaagaccgg aaaatcaata taaaatgtgg cgagaatctc tatatgtcga
        ctgacccttac atcctggaga accgtaattc aaagctggta tgaagaaaat
        gaaaacttcg ttttcggcgt aggagctaaa cccaattccg ctgtcggaca
        ctacactcag cttgtttggt attcatcttt caaagttgga tgtggagttg
        cttactgtcc caatcaagat accctgaaat acttctatgt ttgccattac
        tgtcctatgg gtaacaacgt gatgaaaaag agtaccccat atcatcaagg
        gacaccttgt gctagttgtc ccaataactg tgataatgga ttgtgcacca
        atagctgtga ttttgaagat ttacttagta actgtgaatc cttgaagagt
        tcagcacgct gtaaacatga gttgctcaag gcaaagtgtg aggctacttg
        cctatgtgag gacaaaattc attaacatgc ccagcgtgca gcatgacaga
        ctacatgagg gggggtacaa gacttagttg agacttgaga ggggaaacct
        ataggagagt agtgaaacag tgcatcccaa atgacaaggc ttctttcctt
        cctggattta tatagaaatg tctttcatac aagccattaa gaaagtgtca
        tttaggataa caactctgga ttttgaccaa ctttgctgct tcaaatgtag
        tgaagcgaat caagtggaga attttgaaag ttgcaccata actggtcatt
        cacctctaga actttgaaaa ggagagaact gtttgtgtgt cctaaaccaa
        cctgcaatgg aagaatgggc tgtagttaca tcaccatcaa cctacttcat
        agtgcctacc aggatgaatc ttgacatcta gatttgtctt atgtcttctt
        actttaacac aaatgatcat cttttccaat aa
``` human CRISP-3 cDNA sequence (SEQ ID NO:13)
Accession No. X95240

```
        ctggaaacca ctgcaatgac attattccca gtgctgttgt tcctggttgc
        tgggctgctt ccatcttttc cagcaaatga agataaggat cccgctttta
        ctgctttgtt aaccacccaa acacaagtgc aaagggagat tgtgaataag
        cacaatgaac tgaggagagc agtatctccc cctgccagaa acatgctgaa
        gatggaatgg aacaaagagg ctgcagcaaa tgcccaaaag tgggcaaacc
        agtgcaatta cagacacagt aacccaaagg atcgaatgac aagtctaaaa
```

FIGURE 12D

```
tgtggtgaga atctctacat gtcaagtgcc tccagctcat ggtcacaagc
aatccaaagc tggtttgatg agtacaatga ttttgacttt ggtgtagggc
caaagactcc caacgcagtg gttggacatt atacacaggt tgtttggtac
tcttcatacc tcgttggatg tggaaatgcc tactgtccca atcaaaaagt
tctaaaatac tactatgttt gccaatattg tcctgctggt aattgggcta
atagactata tgtcccttat gaacaaggag caccttgtgc cagttccca
gataactgtg acgatggact atgcaccaat ggttgcaagt acgaagatct
ctatagtaac tgtaaaagtt tgaagctcac attaacctgt aaacatcagt
tggtcaggga cagttgcaag gcctcctgca attgttcaaa cagcatttat
taaatacgca ttacacaccg agtagggcta tgtagagagg agtcagatta
tctacttaga tttggcatct acttagattt aacatatact agctgagaaa
ttgtaggcat gtttgataca catttgattt caaatgtttt tcttctggat
ctgcttttta ttttacaaaa atatttttca tacaaatggt taaaaagaaa
caaaatctat aacaacaact ttggattttt atatataaac tttgtgattt
aaatttactg aatttaatta gggtgaaaat tttgaaagtt gtattctcat
atgactaagt tcactaaaac cctggattga aagtgaaaat tatgttccta
gaacaaaatg tacaaaaaga acaatataat tttcacatga acccttggct
gtagttgcct ttcctagctc cactctaagg ctaagcatct tcaaagacgt
tttcccatat gctgtcttaa ttctttttcac tcattcaccc ttcttcccaa
tcatctggct ggcatcctca caattgagtt gaagctgttc ctcctaaaac
aatcctgact tttattttgc caaaatcaat acaatccttt gaattttta
tctgcataaa ttttacagta gaatatgatc aaaccttcat ttttaaacct
ctcttctctt tgacaaaact tccttaaaaa agaatacaag ataatatagg
taaatacccct ccactcaagg aggtagaact cagtcctctc ccttgtgagt
cttcactaaa atcagtgact cacttccaaa gagtggagta tggaaaggga
aacatagtaa ctttacaggg gagaaaaatg acaaatgacg tcttcaccaa
gtgatcaaaa ttaacgtcac cagtgataag tcattcagat ttgttctaga
taatctttct aaaaattcat aatcccaatc taattatgag ctaaaacatc
cagcaaactc aagttgaagg acattctaca aaatatccct ggggtatttt
agagtattcc tcaaaactgt aaaaatcatg gaaataagg gaatcctgag
aaacaatcac agaccacatg agactaagga gacatgtgag ccaaatgcaa
tgtgcttctt ggatcagatc ctggaacaga aaaagatcag taatgaaaaa
actgatgaag tctgaataga atctggagta tttttaacag tagtgttgat
ttcttaatct tgacaaatat agcagggtaa tgtaagatga taacgttaga
gaaactgaaa ctgggtgagg gctatctagg aattctctgt actatcttac
caaattttcg gtaagtctaa gaaagcaatg caaaataaaa agtgtcttga
           aaaaaaaaaa aaaaaaaaaa aaaaaaa
``` mouse CRISP-3 cDNA sequence (SEQ ID NO:14)
Accession No. L05560

```
          ctcattctac tctgaagcca gcaccatggc attaatgctt gtgctgttct
          tcctggctgc tgtactgccc ccatcccttc ttcaagataa ctctcaggag
          aacagtcttg agaaactttc aaccagtaaa aaatcagtcc aagaagagat
          tgtaagcaag cacaaccaat tgagacgaaa ggtttctcca tctggcagtg
          acttactaaa tatggaatgg aactatgatg ctcaagtgaa tgctcagcaa
          cgggcagaca agtgtacatt cagtcacagt cctatagaac tcaggacaac
```

FIGURE 12E

```
taatttaaaa tgtggtgaga atttgttcat gtcatcttac cttgtaccat
ggtcttctgt aatccaagga tggtataatg aatccaaagg tcttatattt
ggtgtgggcc caaagcaaaa tgttagtgtg gttggacatc atactcaggt
tgtttggaaa tcaaatttac aagttgcatg tggagttgct gaatgccctg
aaaatccact gagatacttt tatgtttgtc gctattgtcc tgtattgaat
tacagtggcc attatccaag caggccatac ctagcttaca cagcaagagc
accatgtgcc agttgtcctg atcgctgtga agatggactg tgcaccaaga
gttgtcaata taaggatatg tcttttggt gtaaacgtct ggaatacgtc
tgtaaacatc caggtcttaa aaaacgttgc ctagctacat gccaatgtta
aggcaaaatt cactaaattt cctgtccagg ctgccaggac caagtagaga
aaggtcatac tctctagtca ggcttatcac atcccaccaa gaatatatag
atttaataca ttggaacaat tccagatggt aaagattctg tttcttcttc
tatttctttc tattttgcag atatcattta ccccaaatat tttaaagtaa
caaaattgat aataacctt ggaccttgac atttgaaatc tgtgacacat
tcatgaagtc aaatctagcc aatgactata cattgtctgt atgactaaag
tcactaaaac tcatatgact aatgttccaa gagcacaatg aagtaaggga
atagaaaaca tatagttcct gtgtaatggt cagtcatctt ttgtagctct
acctagttaa gtctctctga agaaaattca cattgtcttt ttttttttct
cactattcat tattcttcac attcaacata atcagtggtt taaattctaa
aataccattt acattttagt tgttttttt tctaagaatg atataaaatg
taccttaatg agaagaattt gcttgttcag gggacaatga cctttgttgc
tttagaaaaa aaataaatct taatcttggc ttattaaaaa aaaaaaaaa
                              aaaaaa
```

FIGURE 12F

SEQUENCE LISTING

```
<160> NUMBER OF SEQ ID NOS: 14

<210> SEQ ID NO 1
<211> LENGTH: 249
<212> TYPE: PRT
<213> ORGANISM: HOMOSAPIEN

<400> SEQUENCE: 1

Met Glu Ile Lys His Leu Leu Phe Leu Val Ala Ala Cys Leu Leu
1               5                   10                  15

Pro Met Leu Ser Met Lys Lys Lys Ser Ala Arg Asp Gln Phe Asn Lys
                20                  25                  30

Leu Val Thr Asp Leu Pro Asn Val Gln Glu Glu Ile Val Asn Ile His
                35                  40                  45

Asn Ala Leu Arg Arg Arg Val Pro Pro Ala Ser Asn Met Leu Lys
        50                  55                  60

Met Ser Trp Ser Glu Glu Ala Ala Gln Asn Ala Arg Ile Phe Ser Lys
65                  70                  75                  80

Tyr Cys Asp Met Thr Glu Ser Asn Pro Leu Glu Arg Arg Leu Pro Asn
                    85                  90                  95

Thr Phe Cys Gly Glu Asn Met His Met Thr Ser Tyr Pro Val Ser Trp
                100                 105                 110

Ser Ser Val Ile Gly Val Trp Tyr Ser Glu Ser Thr Ser Phe Lys His
            115                 120                 125

Gly Glu Trp Thr Thr Thr Asp Asp Asp Ile Thr Thr Asp His Tyr Thr
        130                 135                 140

Gln Ile Val Trp Ala Thr Ser Tyr Leu Ile Gly Cys Ala Ile Ala Ser
145                 150                 155                 160

Cys Arg Gln Gln Gly Ser Pro Arg Tyr Leu Tyr Val Cys His Tyr Cys
                    165                 170                 175

His Glu Gly Asn Asp Pro Glu Thr Lys Asn Glu Pro Tyr Lys Thr Gly
                180                 185                 190

Val Pro Cys Glu Ala Cys Pro Ser Asn Cys Glu Asp Lys Leu Cys Thr
            195                 200                 205

Asn Pro Cys Ile Tyr Tyr Asp Glu Tyr Phe Asp Cys Asp Ile Gln Val
        210                 215                 220
```

```
His Tyr Leu Gly Cys Asn His Ser Thr Thr Ile Leu Phe Cys Lys Ala
225                 230                 235                 240

Thr Cys Leu Cys Asp Thr Glu Ile Lys
                245

<210> SEQ ID NO 2
<211> LENGTH: 158
<212> TYPE: PRT
<213> ORGANISM: Rattus norvegicus

<400> SEQUENCE: 2

Ala Leu Met Leu Val Leu Leu Phe Leu Ala Ala Val Leu Pro Pro Ser
1               5                   10                  15

Leu Leu Gln Asp Thr Thr Asp Glu Trp Asp Arg Asp Leu Glu Asn Leu
                20                  25                  30

Ser Thr Thr Lys Leu Ser Val Gln Glu Glu Ile Ile Asn Lys His Asn
            35                  40                  45

Gln Leu Arg Arg Thr Val Ser Pro Ser Gly Ser Asp Leu Leu Arg Val
        50                  55                  60

Glu Trp Asp His Asp Ala Tyr Val Asn Ala Gln Lys Trp Ala Asn Arg
65                  70                  75                  80

Cys Ile Tyr Asn His Ser Pro Leu Gln His Arg Thr Thr Thr Leu Lys
                85                  90                  95

Cys Gly Glu Asn Leu Phe Met Ala Asn Tyr Pro Ala Ser Trp Ser Ser
            100                 105                 110

Val Ile Gln Asp Trp Tyr Asp Glu Ser Leu Asp Phe Val Phe Gly Phe
        115                 120                 125

Gly Pro Lys Lys Val Gly Val Lys Val Gly His Tyr Thr Gln Val Val
    130                 135                 140

Trp Asn Ser Thr Phe Leu Val Ala Cys Gly Val Ala Glu Cys
145                 150                 155

<210> SEQ ID NO 3
<211> LENGTH: 244
<212> TYPE: PRT
<213> ORGANISM: MUS MUSCULUS

<400> SEQUENCE: 3

Met Ala Leu Met Leu Val Leu Phe Phe Leu Ala Ala Val Leu Pro Pro
1               5                   10                  15

Ser Leu Leu Gln Asp Ser Ser Gln Glu Asn Arg Leu Glu Lys Leu Ser
                20                  25                  30

Thr Thr Lys Met Ser Val Gln Glu Glu Ile Val Ser Lys His Asn Gln
            35                  40                  45

Leu Arg Arg Met Val Ser Pro Ser Gly Ser Asp Leu Leu Lys Met Glu
        50                  55                  60

Trp Asn Tyr Asp Ala Gln Val Asn Ala Gln Gln Trp Ala Asp Lys Cys
65                  70                  75                  80

Thr Phe Ser His Ser Pro Ile Glu Leu Arg Thr Thr Asn Leu Arg Cys
                85                  90                  95

Gly Glu Asn Leu Phe Met Ser Ser Tyr Leu Ala Ser Trp Ser Ser Ala
            100                 105                 110

Ile Gln Gly Trp Tyr Asn Glu Tyr Lys Asp Leu Thr Tyr Asp Val Gly
        115                 120                 125

Pro Lys Gln Pro Asp Ser Val Val Gly His Tyr Thr Gln Val Val Trp
    130                 135                 140
```

Asn Ser Thr Phe Gln Val Ala Cys Gly Val Ala Glu Cys Pro Lys Asn
145                 150                 155                 160

Pro Leu Arg Tyr Tyr Val Cys His Tyr Cys Pro Val Gly Asn Tyr
            165                 170                 175

Gln Gly Arg Leu Tyr Thr Pro Tyr Thr Ala Gly Glu Pro Cys Ala Ser
            180                 185                 190

Cys Pro Asp His Cys Glu Asp Gly Leu Cys Thr Asn Ser Cys Gly His
                195                 200                 205

Glu Asp Lys Tyr Thr Asn Cys Lys Tyr Leu Lys Lys Met Leu Ser Cys
210                 215                 220

Glu His Glu Leu Leu Lys Lys Gly Cys Lys Ala Thr Cys Leu Cys Glu
225                 230                 235                 240

Gly Lys Ile His

<210> SEQ ID NO 4
<211> LENGTH: 243
<212> TYPE: PRT
<213> ORGANISM: HOMOSAPIEN

<400> SEQUENCE: 4

Met Ala Leu Leu Pro Val Leu Phe Leu Val Thr Val Leu Leu Pro Ser
1               5                   10                  15

Leu Pro Ala Glu Gly Lys Asp Pro Ala Phe Thr Ala Leu Leu Thr Thr
            20                  25                  30

Gln Leu Gln Val Gln Arg Glu Ile Val Asn Lys His Asn Glu Leu Arg
        35                  40                  45

Lys Ala Val Ser Pro Pro Ala Ser Asn Met Leu Lys Met Glu Trp Ser
50                  55                  60

Arg Glu Val Thr Thr Asn Ala Gln Arg Trp Ala Asn Lys Cys Thr Leu
65                  70                  75                  80

Gln His Ser Asp Pro Glu Asp Arg Lys Thr Ser Thr Arg Cys Gly Glu
                85                  90                  95

Asn Leu Tyr Met Ser Ser Asp Pro Thr Ser Trp Ser Ser Ala Ile Gln
            100                 105                 110

Ser Trp Tyr Asp Glu Ile Leu Asp Phe Val Tyr Gly Val Gly Pro Lys
        115                 120                 125

Ser Pro Asn Ala Val Val Gly His Tyr Thr Gln Leu Val Trp Tyr Ser
130                 135                 140

Thr Tyr Gln Val Gly Cys Gly Ile Ala Tyr Cys Pro Asn Gln Asp Ser
145                 150                 155                 160

Leu Lys Tyr Tyr Tyr Val Cys Gln Tyr Cys Pro Ala Gly Asn Asn Met
            165                 170                 175

Asn Arg Lys Asn Thr Pro Tyr Gln Gln Gly Thr Pro Cys Ala Gly Cys
            180                 185                 190

Pro Asp Asp Cys Asp Lys Gly Leu Cys Thr Asn Ser Cys Gln Tyr Gln
            195                 200                 205

Asp Leu Leu Ser Asn Cys Asp Ser Leu Lys Asn Thr Ala Gly Cys Glu
210                 215                 220

His Glu Leu Leu Lys Glu Lys Cys Lys Ala Thr Cys Leu Cys Glu Asn
225                 230                 235                 240

Lys Ile Tyr

<210> SEQ ID NO 5
<211> LENGTH: 243

```
<212> TYPE: PRT
<213> ORGANISM: Rattus norvegicus

<400> SEQUENCE: 5

Met Ala Trp Phe Gln Val Met Leu Phe Val Phe Gly Val Leu Leu Pro
1               5                   10                  15

Leu Pro Pro Thr Glu Gly Lys Asp Pro Asp Phe Ala Thr Leu Thr Thr
            20                  25                  30

Asn Gln Ile Gln Val Gln Arg Glu Ile Ile Ala Lys His Asn Glu Leu
        35                  40                  45

Arg Arg Gln Val Ser Pro Gly Ser Asn Ile Leu Lys Met Glu Trp
    50                  55                  60

Asn Val Gln Ala Ala Asn Ala Gln Lys Trp Ala Asn Asn Cys Ile
65              70                  75                  80

Leu Glu His Ser Ser Thr Glu Asp Arg Lys Ile Asn Ile Lys Cys Gly
                85                  90                  95

Glu Asn Leu Tyr Met Ser Thr Asp Pro Thr Ser Trp Arg Thr Val Ile
            100                 105                 110

Gln Ser Trp Tyr Glu Glu Asn Glu Asn Phe Val Phe Gly Val Gly Ala
        115                 120                 125

Lys Pro Asn Ser Ala Val Gly His Tyr Thr Gln Leu Val Trp Tyr Ser
    130                 135                 140

Ser Phe Lys Val Gly Cys Gly Val Ala Tyr Cys Pro Asn Gln Asp Thr
145                 150                 155                 160

Leu Lys Tyr Phe Tyr Val Cys His Tyr Cys Pro Met Gly Asn Asn Val
                165                 170                 175

Met Lys Lys Ser Thr Pro Tyr His Gln Gly Thr Pro Cys Ala Ser Cys
            180                 185                 190

Pro Asn Asn Cys Asp Asn Gly Leu Cys Thr Asn Ser Cys Asp Phe Glu
        195                 200                 205

Asp Leu Leu Ser Asn Cys Glu Ser Leu Lys Ser Ser Ala Arg Cys Lys
    210                 215                 220

His Glu Leu Leu Lys Ala Lys Cys Glu Ala Thr Cys Leu Cys Glu Asp
225                 230                 235                 240

Lys Ile His

<210> SEQ ID NO 6
<211> LENGTH: 245
<212> TYPE: PRT
<213> ORGANISM: HOMOSAPIEN

<400> SEQUENCE: 6

Met Thr Leu Phe Pro Val Leu Leu Phe Leu Val Ala Gly Leu Leu Pro
1               5                   10                  15

Ser Phe Pro Ala Asn Glu Asp Lys Asp Pro Ala Phe Thr Ala Leu Leu
            20                  25                  30

Thr Thr Gln Thr Gln Val Gln Arg Glu Ile Val Asn Lys His Asn Glu
        35                  40                  45

Leu Arg Arg Ala Val Ser Pro Pro Ala Arg Asn Met Leu Lys Met Glu
    50                  55                  60

Trp Asn Lys Glu Ala Ala Ala Asn Ala Gln Lys Trp Ala Asn Gln Cys
65              70                  75                  80

Asn Tyr Arg His Ser Asn Pro Lys Asp Arg Met Thr Ser Leu Lys Cys
                85                  90                  95

Gly Glu Asn Leu Tyr Met Ser Ser Ala Ser Ser Ser Trp Ser Gln Ala
```

-continued

```
                    100                 105                 110
Ile Gln Ser Trp Phe Asp Glu Tyr Asn Asp Phe Asp Phe Gly Val Gly
            115                 120                 125

Pro Lys Thr Pro Asn Ala Val Val Gly His Tyr Thr Gln Val Val Trp
        130                 135                 140

Tyr Ser Ser Tyr Leu Val Gly Cys Gly Asn Ala Tyr Cys Pro Asn Gln
145                 150                 155                 160

Lys Val Leu Lys Tyr Tyr Val Cys Gln Tyr Cys Pro Ala Gly Asn
            165                 170                 175

Trp Ala Asn Arg Leu Tyr Val Pro Tyr Glu Gln Gly Ala Pro Cys Ala
        180                 185                 190

Ser Cys Pro Asp Asn Cys Asp Asp Gly Leu Cys Thr Asn Gly Cys Lys
            195                 200                 205

Tyr Glu Asp Leu Tyr Ser Asn Cys Lys Ser Leu Lys Leu Thr Leu Thr
        210                 215                 220

Cys Lys His Gln Leu Val Arg Asp Ser Cys Lys Ala Ser Cys Asn Cys
225                 230                 235                 240

Ser Asn Ser Ile Tyr
            245

<210> SEQ ID NO 7
<211> LENGTH: 241
<212> TYPE: PRT
<213> ORGANISM: MUS MUSCULUS

<400> SEQUENCE: 7

Met Ala Leu Met Leu Val Leu Phe Phe Leu Ala Ala Val Leu Pro Pro
1               5                   10                  15

Ser Leu Leu Gln Asp Asn Ser Gln Glu Asn Ser Leu Glu Lys Leu Ser
            20                  25                  30

Thr Ser Lys Lys Ser Val Gln Glu Glu Ile Val Ser Lys His Asn Gln
        35                  40                  45

Leu Arg Arg Lys Val Ser Pro Ser Gly Ser Asp Leu Leu Asn Met Glu
    50                  55                  60

Trp Asn Tyr Asp Ala Gln Val Asn Ala Gln Gln Arg Ala Asp Lys Cys
65                  70                  75                  80

Thr Phe Ser His Ser Pro Ile Glu Leu Arg Thr Thr Asn Leu Lys Cys
            85                  90                  95

Gly Glu Asn Leu Phe Met Ser Ser Tyr Leu Val Pro Trp Ser Ser Val
        100                 105                 110

Ile Gln Gly Trp Tyr Asn Glu Ser Lys Gly Leu Ile Phe Gly Val Gly
            115                 120                 125

Pro Lys Gln Asn Val Ser Val Val Gly His His Thr Gln Val Val Trp
        130                 135                 140

Lys Ser Asn Leu Gln Val Ala Cys Gly Val Ala Glu Cys Pro Glu Asn
145                 150                 155                 160

Pro Leu Arg Tyr Phe Tyr Val Cys Arg Tyr Cys Pro Val Leu Asn Tyr
            165                 170                 175

Ser Gly His Tyr Pro Ser Arg Pro Tyr Leu Ala Tyr Thr Ala Arg Ala
        180                 185                 190

Pro Cys Ala Ser Cys Pro Asp Arg Cys Glu Asp Gly Leu Cys Thr Lys
            195                 200                 205

Ser Cys Gln Tyr Lys Asp Met Ser Phe Trp Cys Lys Arg Leu Glu Tyr
        210                 215                 220
```

```
Val Cys Lys His Pro Gly Leu Lys Lys Arg Cys Leu Ala Thr Cys Gln
225                 230                 235                 240

Cys

<210> SEQ ID NO 8
<211> LENGTH: 1886
<212> TYPE: PRT
<213> ORGANISM: HOMOSAPIEN

<400> SEQUENCE: 8

Gly Cys Ala Cys Ala Ala Thr Ala Cys Ala Cys Thr Ala Cys Ala
1               5                   10                  15

Thr Ala Gly Ala Gly Ala Ala Gly Gly Cys Thr Thr Gly Gly Thr
                20                  25                  30

Thr Cys Thr Thr Ala Thr Cys Ala Gly Ala Cys Ala Cys Ala Ala
            35                  40                  45

Ala Thr Thr Thr Ala Ala Gly Gly Cys Thr Gly Thr Gly Thr Gly
        50                  55                  60

Gly Ala Cys Thr Thr Gly Gly Gly Ala Thr Gly Gly Ala Ala Ala
65                  70                  75                  80

Thr Thr Ala Ala Ala Cys Ala Cys Thr Cys Thr Thr Gly Thr Thr
                85                  90                  95

Thr Thr Thr Gly Gly Thr Thr Gly Cys Thr Gly Cys Thr Gly Cys Thr
            100                 105                 110

Thr Gly Cys Thr Thr Ala Cys Thr Gly Cys Cys Thr Ala Thr Gly Thr
        115                 120                 125

Thr Gly Thr Cys Cys Ala Thr Gly Ala Ala Ala Ala Gly Ala Ala
    130                 135                 140

Ala Thr Cys Ala Gly Cys Thr Ala Gly Ala Gly Ala Cys Cys Ala Ala
145                 150                 155                 160

Thr Thr Thr Ala Ala Thr Ala Ala Gly Cys Thr Cys Gly Thr Cys Ala
                165                 170                 175

Cys Cys Gly Ala Cys Thr Thr Gly Cys Cys Ala Ala Thr Gly Thr
            180                 185                 190

Ala Cys Ala Ala Gly Ala Ala Gly Ala Gly Ala Thr Cys Gly Thr Thr
        195                 200                 205

Ala Ala Thr Ala Thr Ala Cys Ala Cys Ala Ala Cys Gly Cys Cys
    210                 215                 220

Thr Cys Ala Gly Gly Ala Gly Ala Ala Gly Ala Gly Thr Ala Gly Thr
225                 230                 235                 240

Thr Cys Cys Ala Cys Cys Ala Gly Cys Cys Ala Gly Cys Ala Ala Cys
                245                 250                 255

Ala Thr Gly Cys Thr Gly Ala Ala Gly Ala Thr Gly Ala Gly Thr Thr
            260                 265                 270

Gly Gly Ala Gly Thr Gly Ala Ala Gly Ala Gly Gly Cys Thr Gly Cys
        275                 280                 285

Ala Cys Ala Ala Ala Thr Gly Cys Cys Ala Gly Ala Ala Thr Thr
    290                 295                 300

Thr Thr Thr Thr Cys Ala Ala Ala Gly Thr Ala Thr Thr Gly Thr Gly
305                 310                 315                 320

Ala Thr Ala Thr Gly Ala Cys Ala Gly Ala Gly Ala Gly Cys Ala Ala
                325                 330                 335

Cys Cys Cys Cys Cys Thr Thr Gly Ala Gly Ala Gly Gly Ala Gly Ala
            340                 345                 350
```

-continued

```
Cys Thr Thr Cys Cys Ala Ala Ala Thr Ala Cys Cys Thr Thr Thr Thr
        355                 360                 365

Gly Thr Gly Gly Ala Gly Ala Ala Ala Ala Thr Ala Thr Gly Cys Ala
    370                 375                 380

Thr Ala Thr Gly Ala Cys Ala Thr Cys Thr Thr Ala Thr Cys Cys Thr
385                 390                 395                 400

Gly Thr Ala Thr Cys Ala Thr Gly Gly Thr Cys Ala Ala Gly Thr Gly
                405                 410                 415

Thr Ala Ala Thr Thr Gly Gly Ala Gly Thr Cys Thr Gly Gly Thr Ala
            420                 425                 430

Cys Ala Gly Thr Gly Ala Gly Thr Cys Thr Ala Cys Ala Ala Gly Thr
        435                 440                 445

Thr Thr Cys Ala Ala Ala Cys Ala Thr Gly Gly Ala Gly Ala Ala Thr
    450                 455                 460

Gly Gly Ala Cys Ala Ala Cys Ala Ala Cys Gly Gly Ala Thr Gly Ala
465                 470                 475                 480

Thr Gly Ala Cys Ala Thr Ala Ala Cys Thr Ala Cys Thr Gly Ala Cys
                485                 490                 495

Cys Ala Cys Thr Ala Cys Ala Cys Thr Cys Ala Gly Ala Thr Thr Gly
            500                 505                 510

Thr Thr Thr Gly Gly Gly Cys Cys Ala Cys Ala Thr Cys Thr Thr Ala
        515                 520                 525

Cys Cys Thr Gly Ala Thr Thr Gly Gly Cys Thr Gly Thr Gly Cys Cys
    530                 535                 540

Ala Thr Thr Gly Cys Ala Thr Cys Thr Thr Gly Cys Cys Gly Cys Cys
545                 550                 555                 560

Ala Ala Cys Ala Ala Gly Gly Ala Thr Cys Ala Cys Cys Thr Cys Gly
                565                 570                 575

Ala Thr Ala Thr Cys Thr Cys Thr Ala Cys Gly Thr Thr Thr Gly Thr
            580                 585                 590

Cys Ala Cys Thr Ala Thr Thr Gly Thr Cys Ala Thr Gly Ala Gly Gly
        595                 600                 605

Gly Ala Ala Ala Thr Gly Ala Thr Cys Cys Thr Gly Ala Ala Ala Cys
    610                 615                 620

Ala Ala Ala Gly Ala Ala Thr Gly Ala Ala Cys Cys Thr Thr Ala Thr
625                 630                 635                 640

Ala Ala Gly Ala Cys Ala Gly Gly Cys Gly Thr Cys Cys Cys Ala Thr
                645                 650                 655

Gly Thr Gly Ala Ala Gly Cys Cys Thr Gly Cys Cys Cys Ala Ala Gly
            660                 665                 670

Thr Ala Ala Cys Thr Gly Thr Gly Ala Ala Gly Ala Cys Ala Ala Ala
        675                 680                 685

Cys Thr Thr Thr Gly Cys Ala Cys Thr Ala Ala Cys Cys Cys Cys Thr
    690                 695                 700

Gly Cys Ala Thr Cys Thr Ala Cys Thr Ala Thr Gly Ala Thr Gly Ala
705                 710                 715                 720

Ala Thr Ala Cys Thr Thr Cys Gly Ala Cys Thr Gly Thr Gly Ala Cys
                725                 730                 735

Ala Thr Ala Cys Ala Ala Gly Thr Cys Cys Ala Thr Thr Ala Thr Cys
            740                 745                 750

Thr Gly Gly Gly Ala Thr Gly Cys Ala Ala Cys Cys Ala Cys Thr Cys
        755                 760                 765

Ala Ala Cys Ala Ala Cys Thr Ala Thr Cys Cys Thr Ala Thr Thr Cys
```

-continued

```
                  770             775             780
Thr Gly Thr Ala Ala Ala Gly Cys Cys Ala Cys Thr Thr Gly Thr Cys
785                     790                 795                 800
Thr Gly Thr Gly Thr Gly Ala Cys Ala Cys Thr Gly Ala Gly Ala Thr
            805                 810                 815
Ala Ala Ala Ala Thr Ala Gly Gly Thr Cys Thr Thr Thr Gly Thr Thr
            820                 825                 830
Ala Thr Thr Thr Thr Cys Ala Ala Cys Thr Gly Thr Thr Cys Thr Ala
            835                 840                 845
Thr Gly Cys Thr Gly Thr Gly Ala Cys Gly Ala Thr Gly Ala Gly Gly
        850                 855                 860
Ala Gly Gly Ala Gly Ala Thr Gly Thr Cys Thr Gly Thr Thr Gly Gly
865                 870                 875                 880
Ala Thr Thr Cys Ala Thr Gly Thr Cys Thr Thr Thr Gly Cys Thr
            885                 890                 895
Ala Thr Ala Gly Thr Thr Cys Ala Gly Thr Ala Gly Cys Thr Thr Cys
            900                 905                 910
Thr Gly Cys Thr Ala Ala Ala Thr Thr Cys Ala Cys Thr Gly Ala
        915                 920                 925
Thr Thr Thr Thr Ala Ala Thr Cys Ala Thr Gly Cys Thr Gly Gly Ala
        930                 935                 940
Gly Ala Cys Cys Thr Thr Ala Ala Cys Thr Cys Cys Ala Thr Cys
945                 950                 955                 960
Cys Thr Gly Ala Thr Ala Cys Ala Thr Cys Thr Gly Ala Ala Gly
            965                 970                 975
Thr Ala Ala Cys Ala Cys Thr Gly Thr Thr Thr Ala Ala Ala Cys
            980                 985                 990
Thr Thr Thr Cys Thr Thr Ala Gly  Thr Gly Cys Thr Gly  Gly Ala Gly
            995                 1000                1005
Thr Ala  Ala Ala Gly Gly  Thr Cys Ala Ala Gly  Thr Cys Cys
    1010                1015                1020
Ala Ala  Cys Ala Cys Cys Thr  Gly Cys Cys Thr Thr  Ala Ala Ala
    1025                1030                1035
Thr Thr  Thr Ala Ala Ala Thr  Cys Ala Thr Gly Thr  Gly Ala Thr
    1040                1045                1050
Thr Thr  Ala Thr Ala Gly Thr  Thr Thr Thr Ala  Ala Gly Thr
    1055                1060                1065
Thr Gly  Gly Cys Ala Thr Ala  Ala Thr Thr Cys Ala  Ala Cys Thr
    1070                1075                1080
Thr Ala  Thr Gly Gly Thr Ala  Thr Ala Ala Cys Thr  Gly Gly Gly
    1085                1090                1095
Thr Cys  Cys Cys Thr Cys Ala  Ala Cys Ala Gly Thr  Ala Ala Cys
    1100                1105                1110
Cys Thr  Gly Gly Gly Cys Thr  Ala Ala Ala Ala Thr  Ala Gly Gly
    1115                1120                1125
Thr Cys  Thr Thr Ala Thr Gly  Thr Gly Gly Thr Thr  Cys Ala Ala
    1130                1135                1140
Cys Thr  Cys Cys Cys Ala Cys  Cys Cys Cys Gly  Cys Cys Thr
    1145                1150                1155
Thr Cys  Cys Cys Cys Ala Thr  Ala Thr Thr Thr  Cys Ala Ala
    1160                1165                1170
Cys Cys  Ala Cys Thr Cys Thr  Gly Ala Thr Thr Ala  Thr Cys Thr
    1175                1180                1185
```

-continued

```
Thr Cys Cys Cys Thr Gly Cys Ala Cys Ala Ala Cys Thr Ala Ala
    1190             1195             1200

Cys Ala Thr Cys Cys Ala Gly Thr Ala Ala Thr Ala Ala Thr Thr
    1205             1210             1215

Cys Thr Thr Cys Ala Cys Thr Thr Thr Ala Ala Ala Ala Thr
    1220             1225             1230

Thr Thr Thr Ala Cys Thr Thr Cys Thr Ala Cys Thr Thr Thr Ala
    1235             1240             1245

Ala Ala Thr Cys Ala Ala Thr Cys Ala Thr Thr Ala Ala Ala Gly
    1250             1255             1260

Gly Ala Ala Thr Cys Cys Ala Cys Ala Ala Ala Gly Cys Ala Ala
    1265             1270             1275

Ala Cys Ala Gly Ala Gly Thr Thr Cys Ala Gly Thr Cys Thr Cys
    1280             1285             1290

Ala Thr Cys Thr Thr Gly Cys Ala Ala Gly Gly Thr Ala Ala Ala
    1295             1300             1305

Thr Ala Thr Cys Ala Thr Thr Thr Ala Ala Thr Thr Gly Gly Ala
    1310             1315             1320

Ala Gly Thr Ala Gly Thr Thr Thr Ala Ala Ala Thr Gly Thr Cys
    1325             1330             1335

Thr Cys Ala Thr Thr Gly Thr Thr Thr Thr Ala Thr Thr Gly Ala
    1340             1345             1350

Cys Ala Cys Ala Thr Cys Thr Ala Thr Ala Thr Ala Thr Ala Cys
    1355             1360             1365

Ala Thr Thr Thr Gly Thr Gly Ala Ala Gly Cys Ala Ala Gly Ala
    1370             1375             1380

Ala Ala Cys Ala Ala Thr Ala Ala Ala Ala Ala Ala Gly Cys Thr
    1385             1390             1395

Thr Cys Gly Thr Ala Thr Gly Cys Cys Ala Thr Thr Ala Ala Thr
    1400             1405             1410

Thr Thr Ala Ala Cys Ala Ala Ala Ala Thr Ala Thr Gly Thr Ala
    1415             1420             1425

Thr Thr Cys Ala Gly Thr Ala Cys Thr Gly Ala Thr Thr Gly Cys
    1430             1435             1440

Ala Thr Ala Cys Ala Ala Gly Ala Thr Gly Cys Ala Thr Gly Thr
    1445             1450             1455

Thr Thr Ala Thr Ala Thr Ala Thr Ala Thr Gly Gly Ala Ala Gly
    1460             1465             1470

Gly Ala Ala Thr Ala Thr Ala Gly Thr Thr Thr Cys Ala Thr Thr
    1475             1480             1485

Thr Cys Ala Thr Thr Gly Cys Ala Ala Ala Gly Gly Cys Ala Gly
    1490             1495             1500

Thr Ala Thr Ala Ala Ala Ala Gly Ala Thr Ala Thr Ala Thr Ala
    1505             1510             1515

Ala Ala Ala Thr Ala Gly Cys Ala Thr Ala Ala Thr Ala Thr Gly
    1520             1525             1530

Ala Gly Ala Ala Ala Thr Thr Ala Ala Gly Thr Cys Cys Cys Thr
    1535             1540             1545

Ala Ala Ala Gly Ala Cys Ala Thr Ala Thr Ala Gly Gly Thr Cys
    1550             1555             1560

Ala Cys Ala Thr Ala Thr Thr Ala Thr Thr Ala Thr Thr Gly Cys
    1565             1570             1575
```

| | | | | | | | | |
|---|---|---|---|---|---|---|---|---|
| Cys | Ala | Gly | Ala | Thr | Gly | Ala | Gly | Cys | Ala | Thr | Ala | Ala | Ala | Thr |
| 1580 | | | | | 1585 | | | | | 1590 | | | | |

Cys Ala Gly Ala Thr Gly Ala Gly Cys Ala Thr Ala Ala Ala Thr
        1580                    1585                    1590

Ala Gly Cys Thr Thr Cys Thr Gly Thr Thr Thr Gly Gly Ala Gly
        1595                    1600                    1605

Ala Thr Thr Cys Ala Gly Gly Ala Ala Ala Gly Cys Cys Thr Thr
        1610                    1615                    1620

Ala Gly Gly Gly Thr Gly Gly Ala Ala Thr Gly Ala Gly Gly Ala
        1625                    1630                    1635

Ala Cys Ala Thr Cys Thr Thr Cys Thr Gly Ala Gly Thr Ala Ala
        1640                    1645                    1650

Ala Cys Ala Gly Gly Gly Thr Thr Gly Cys Ala Ala Ala Gly Gly
        1655                    1660                    1665

Thr Thr Ala Thr Gly Ala Thr Thr Ala Thr Thr Thr Cys Ala Ala
        1670                    1675                    1680

Cys Ala Cys Ala Ala Thr Gly Gly Ala Ala Gly Ala Gly Cys Ala
        1685                    1690                    1695

Cys Ala Gly Thr Thr Ala Ala Gly Gly Cys Cys Ala Ala Cys Thr
        1700                    1705                    1710

Ala Ala Cys Gly Thr Ala Ala Ala Ala Thr Gly Cys Ala Cys Thr
        1715                    1720                    1725

Gly Ala Ala Gly Cys Cys Thr Thr Ala Gly Gly Gly Ala Ala Thr
        1730                    1735                    1740

Ala Thr Thr Gly Ala Ala Gly Gly Gly Cys Cys Thr Gly Ala Cys
        1745                    1750                    1755

Ala Thr Gly Gly Gly Gly Ala Ala Ala Gly Gly Gly Ala Ala Gly
        1760                    1765                    1770

Gly Cys Thr Ala Gly Ala Ala Ala Thr Ala Cys Thr Thr Gly Gly
        1775                    1780                    1785

Thr Cys Ala Ala Ala Thr Thr Thr Thr Ala Ala Cys Ala Thr Thr
        1790                    1795                    1800

Ala Thr Ala Cys Cys Ala Ala Ala Gly Thr Thr Ala Thr Ala Cys
        1805                    1810                    1815

Cys Cys Ala Gly Thr Thr Cys Thr Ala Cys Cys Thr Ala Cys Thr
        1820                    1825                    1830

Thr Gly Thr Ala Thr Ala Thr Thr Thr Cys Thr Thr Thr Ala Cys
        1835                    1840                    1845

Thr Cys Ala Thr Thr Thr Cys Ala Ala Thr Ala Ala Ala Gly Thr
        1850                    1855                    1860

Gly Thr Thr Thr Gly Ala Ala Ala Ala Ala Ala Ala Ala Ala Ala
        1865                    1870                    1875

Ala Ala Ala Ala Ala Ala Ala Ala
        1880                    1885

<210> SEQ ID NO 9
<211> LENGTH: 1498
<212> TYPE: DNA
<213> ORGANISM: Rattus norvegicus

<400> SEQUENCE: 9
aactcctcag gaagaccagc agagtcaact aacctggacc cttggtagct cccggcgact    60
gaatcattaa gcaaagggac aatatctcat tctgctctga aaatagaacc atggcattaa   120
tgttagtgct gttgttcctg gctgctgtat tgccaccatc tcttcttcaa gataccactg   180
atgaatggga tagagatctt gagaatttgt caaccactaa actgtcagtc caagaagaga   240

-continued

```
tcataaacaa gcacaaccaa ttgagacgaa cggtttctcc gtctggtagt gacttactaa    300
gagtggaatg ggaccatgat gcttatgtga acgctcagaa atgggcaaac aggtgcattt    360
acaatcacag tcctctacaa cacaggacaa ccacattaaa atgtggtgag aatttgttca    420
tggcaaatta ccctgcatcg tggtcttctg taatccaaga ttggtatgat gaatcccttg    480
attttgtctt tggtttcggc ccaaaaaaag ttggtgttaa agtcggacac tatactcagg    540
ttgtttggaa ttcaactttc ctggttgcat gtggagttgc tgaatgccct gaccaaccat    600
tgaaatactt ttatgtttgt cactattgtc ctggtggcaa ttatgtagga agactatact    660
caccttacac agaaggagaa ccttgtgaca gttgtcctgg taattgtgaa gatgggctgt    720
gcaccaatag ttgtgaatat gaagataatt attctaactg tggcgatctg aagaagatgg    780
tgagctgcga cgatccactt cttaaagaag gttgcagagc ttcatgcttc tgtgaagaca    840
aaattcatta aatttccagt ccacataatc aggaccatgt agaaaaggaa aatacccctct   900 acttagtctt atcatgtccc accaaaaata tgtaggttta gtacactgaa ataattccaa    960
atggtaaaga ttctgtttct tctcctattt ctctctattt tgcataagtc atttaccccca  1020 aaatatttta aaataacaaa atcaataccc cctttggaac tggccatatg aaatctgtga   1080
cacatttatg gaatcaaatc tatcccacga ttatatatta tttgtctgta tgacttaagt   1140
cactaaatct ctggcttgaa aatatgaatc atgttcccag agcacaatga aataagagaa   1200
cagatagcat atagtccctc tgtattggcc aatcacttttt ttttagttc taccactatt   1260 tttagctaat tatctccgga gaaaacattc acattaattg tcttctattt cttctcacca   1320
ttcattattc ttcacattca tcagaattag tggtttaaat tctaaactac catttatgtt   1380
ttgttgtcgg gtctttaaga atgatattaa aatgtaactt aataaacaga atttgcttgt   1440 tcagggggtaa tgaccttggt tgcttcagaa aaaaaataaa tcttaatctt agcatatt    1498
```

<210> SEQ ID NO 10
<211> LENGTH: 1403
<212> TYPE: DNA
<213> ORGANISM: MUS MUSCULUS

<400> SEQUENCE: 10

```
ctcattctac tctgaagcca gcaccatggc attaatgctt gtgctgttct tcttggctgc     60
tgtactgccc ccatcccttc ttcaagatag ctctcaggaa aatcgtcttg agaaacttttc   120 aaccactaaa atgtcagtcc aagaagagat tgtaagcaag cacaaccaat tgagacgaat   180
ggtttctcca tctggcagtg acttactaaa atggaatgg aactatgatg ctcaagtgaa   240
tgctcagcaa tgggcagaca agtgtacatt cagtcacagt cctatagaac tcaggacaac   300
taatttaaga tgtgggggaga atttgttcat gtcatcttac cttgcatcat ggtcttctgc   360
aatccaagga tggtataatg aatacaaaga tcttacatat gatgttggcc caaagcaacc   420
tgatagtgtg gttggacatt atactcaggt tgtttggaac tcaactttcc aagttgcatg   480
tggagttgct gaatgcccta aaaatccact gagatactat tatgtttgtc actattgtcc   540
tgttggcaat tatcaaggaa ggctatacac accttacact gcaggagaac cgtgtgccag   600
ttgtcctgat cactgtgaag atgggctatg caccaatagt tgtggacatg aagataagta   660
tactaactgt aaatatctga agaagatgct atcctgtgaa catgaacttc ttaaaaaagg   720
ttgcaaagct acatgcctct gtgaaggcaa aattcactaa atttcctgta ctcgtagcca   780
ggaccatgta gagaaagctc atactctcta gttaggctta tcacatccca ccaagaaagt   840
atagatttag gacattgaaa taattccaga tagtaaagat tctgtttctt cttctatttc    900
```

-continued

| | |
|---|---|
| tttctatttt acagaaatca tttaccccaa atattttaaa ataacaaatt tgataatacc | 960 |
| tttgtacctt gacatatgaa atctgtgaca cattttcgga gtcaagtcta gcccatgatt | 1020 |
| atacattgtc tgtatgacta aagtcactaa aactcatatg actaatgttc aagagcaca | 1080 |
| atgaagtaaa ggaatagaaa acatatagtt cctgtataat ggtcagtcat cttttctagc | 1140 |
| tctacctagt ttactctctc tggagaaaat cacattaatc gtcttttatt ttctttctca | 1200 |
| ctattcctta ttcttcaaat tcatcataat cagtggttta aattctaaac tactatttac | 1260 |
| attttagttt tttttaaaga atgatataaa atgtacctta acgagcagaa tttatagttt | 1320 |
| gcttgttcag gggacaatga cctttgttgc tttagaaaaa taataaatct taatcttggc | 1380 |
| aaaaaaaaaa aaaaaaaaaa aaa | 1403 |

<210> SEQ ID NO 11
<211> LENGTH: 1406
<212> TYPE: DNA
<213> ORGANISM: HOMOSAPIEN

<400> SEQUENCE: 11

| | |
|---|---|
| cggtgagagg ggcgcgcagc agcagctcct caacgccgca acgcgccggc ccaactgcag | 60 |
| gaaggtctgt gctctggagc cagggtaaat ggttataaaa ttatacacca tggccctcct | 120 |
| aaagacactc taggaaaacc atgtcatcct gatcttaaaa cacctgcaag aaagagcaca | 180 |
| gtacttcacc attaataaag tagatatttc atcctgctca gaaaaccaac atttccagca | 240 |
| atggctttac taccggtgtt gtttctggtt actgtgctgc ttccatcttt acctgcagaa | 300 |
| ggaaaggatc ccgcttttac tgctttgtta accacccagt tgcaagtgca aagggagatt | 360 |
| gtaaataaac acaatgaact aaggaaagca gtctctccac ctgccagtaa catgctaaag | 420 |
| atggaatgga gcagagaggt aacaacgaat gcccaaaggt gggcaaacaa gtgcacttta | 480 |
| caacatagtg atccagagga ccgcaaaacc agtacaagat gtggtgagaa tctctatatg | 540 |
| tcaagtgacc ctacttcctg gtcttctgca atccaaagct ggtatgacga gatcctagat | 600 |
| tttgtctatg gtgtaggacc aaagagtccc aatgcagttg ttggacatta tactcagctt | 660 |
| gtttggtact cgacttacca ggtaggctgt ggaattgcct actgtcccaa tcaagatagt | 720 |
| ctaaatact actatgtttg ccaatattgt cctgctggta ataatatgaa tagaaagaat | 780 |
| accccgtacc aacaaggaac accttgtgcc ggttgccctg atgactgtga caaaggacta | 840 |
| tgcaccaata gttgccagta tcaagatctc ctaagtaact gtgattcctt gaagaataca | 900 |
| gctggctgtg aacatgagtt actcaaggaa aagtgcaagg ctacttgcct atgtgagaac | 960 |
| aaaatttact gatttaccta gtgagcattg tgcaagactg catggataag ggctgcatca | 1020 |
| tttaattgcg acataccagt ggaaattgta tgtatgttag tgacaaattt gatttcaaag | 1080 |
| agcaatgcat cttctccccc agatcatcac agaaatcact ttcaggcaat gatttacaaa | 1140 |
| agtagcatag tagatgatga caactgtgaa ctctgacata aatttagtgc tttataacga | 1200 |
| actgaatcag gttgaggatt ttgaaaactg tataaccata ggatttaggt cactaggact | 1260 |
| ttggatcaaa atggtgcatt acgtatttcc tgaaacatgc taaagaagaa gactgtaaca | 1320 |
| tcattgccat tcctactacc tgagttttta cttgcataaa caataaattc aaagctttac | 1380 |
| atctgcaaaa aaaaaaaaaa aaaaaa | 1406 |

<210> SEQ ID NO 12
<211> LENGTH: 1432
<212> TYPE: DNA

<213> ORGANISM: Rattus norvegicus
<220> FEATURE:
<221> NAME/KEY: misc_feature
<222> LOCATION: (282)..(282)
<223> OTHER INFORMATION: A, T, C, or G

<400> SEQUENCE: 12

```
ccggcaatga gcaggtggtt gaggtctgca gaaatagcag cagcccccat gctgacctct      60
ttcctttctg acaccatgaa gacctgggct gtggagctag ggataaggaa aacaaacacc     120
atgaccctca cactttaaaa gaagcatgtc ctcctgatct tcaaacatca gaagaaagga     180
caagataagg cagatatttc aactgtcaaa tcaacactaa ctgtcaaatc aacacttcca     240
gccatggctt ggttccaggt gatgctgttt gtctttggtg tnctgctacc attgccaccc     300
acagaaggaa aggatccaga cttcgctact ttgacaacca accaaataca agttcaaaga     360
gagatcatag ctaaacacaa tgaactgagg agacaagtta gccccctgg cagcaacata      420
ctaaaaatga aatggaacgt acaagcagca gcaaatgctc aaaagtgggc taataactgt     480
attttagaac acagtagtac agaagaccgg aaaatcaata taaaatgtgg cgagaatctc     540
tatatgtcga ctgaccctac atcctggaga accgtaattc aaagctggta tgaagaaaat     600
gaaaacttcg ttttcggcgt aggagctaaa cccaattccg ctgtcggaca ctacactcag     660
cttgtttggt attcatcttt caaagttgga tgtggagttg cttactgtcc aatcaagat      720
accctgaaat acttctatgt tgccattac tgtcctatgg gtaacaacgt gatgaaaaag      780
agtaccccat atcatcaagg gacaccttgt gctagttgtc ccataactg tgataatgga      840
ttgtgcacca atagctgtga ttttgaagat ttacttagta actgtgaatc cttgaagagt     900
tcagcacgct gtaaacatga gttgctcaag gcaaagtgtg aggctacttg cctatgtgag     960
gacaaaattc attaacatgc ccagcgtgca gcatgacaga ctacatgagg gggggtacaa    1020
gacttagttg agacttgaga ggggaaacct ataggagagt agtgaaacag tgcatcccaa    1080
atgacaaggc ttcttcctt cctggattta tatagaaatg tctttcatac aagccattaa    1140
gaaagtgtca tttaggataa caactctgga ttttgaccaa ctttgctgct tcaaatgtag    1200
tgaagcgaat caagtggaga attttgaaag ttgcaccata actggtcatt cacctctaga    1260
actttgaaaa ggagagaact gttttgtgtgt cctaaaccaa cctgcaatgg aagaatgggc    1320
tgtagttaca tcaccatcaa cctacttcat agtgcctacc aggatgaatc ttgacatcta    1380
gatttgtctt atgtcttctt actttaacac aaatgatcat cttttccaat aa            1432
```

<210> SEQ ID NO 13
<211> LENGTH: 2128
<212> TYPE: DNA
<213> ORGANISM: HOMOSAPIEN

<400> SEQUENCE: 13

```
ctggaaacca ctgcaatgac attattccca gtgctgttgt tcctggttgc tgggctgctt      60
ccatcttttc cagcaaatga agataaggat cccgctttta ctgctttgtt aaccacccaa     120
acacaagtgc aaagggagat tgtgaataag cacaatgaac tgaggagagc agtatctccc     180
cctgccagaa acatgctgaa gatggaatgg aacaagagg ctgcagcaaa tgcccaaaag      240
tgggcaaacc agtgcaatta cagacacagt aacccaaagg atcgaatgac aagtctaaaa     300
tgtggtgaga atctctacat gtcaagtgcc tccagctcat ggtcacaagc aatccaaagc     360
tggtttgatg agtacaatga ttttgacttt ggtgtagggc aaagactcc caacgcagtg     420
gttggacatt atacacaggt tgtttggtac tcttcatacc tcgttggatg tggaaatgcc    480
```

```
tactgtccca atcaaaaagt tctaaaatac tactatgttt gccaatattg tcctgctggt      540
aattgggcta atagactata tgtcccttat gaacaaggag caccttgtgc cagttgccca      600
gataactgtg acgatggact atgcaccaat ggttgcaagt acgaagatct ctatagtaac      660
tgtaaaagtt tgaagctcac attaacctgt aaacatcagt tggtcaggga cagttgcaag      720
gcctcctgca attgttcaaa cagcatttat taaatacgca ttacacaccg agtagggcta      780
tgtagagagg agtcagatta tctacttaga tttggcatct acttagattt aacatatact      840
agctgagaaa ttgtaggcat gtttgataca catttgattt caaatgtttt tcttctggat      900
ctgcttttta ttttacaaaa atattttca tacaaatggt taaaagaaa caaaatctat       960 aacaacaact ttggattttt atatataaac tttgtgattt aaatttactg aatttaatta     1020
gggtgaaaat tttgaaagtt gtattctcat atgactaagt tcactaaaac cctggattga     1080
aagtgaaaat tatgttccta gaacaaaatg tacaaaaaga acaatataat tttcacatga     1140
acccttggct gtagttgcct ttcctagctc cactctaagg ctaagcatct tcaaagacgt     1200
tttcccatat gctgtcttaa ttcttttcac tcattcaccc ttcttcccaa tcatctggct     1260
ggcatcctca caattgagtt gaagctgttc ctcctaaaac aatcctgact tttattttgc     1320
caaaatcaat acaatccttt gaatttttta tctgcataaa ttttacagta gaatatgatc     1380
aaaccttcat ttttaaacct ctcttctctt tgacaaaact tccttaaaaa agaatacaag     1440
ataatatagg taaatacctt ccactcaagg aggtagaact cagtcctctc ccttgtgagt     1500
cttcactaaa atcagtgact cacttccaaa gagtggagta tggaaaggga aacatagtaa     1560
ctttacaggg gagaaaaatg acaaatgacg tcttcaccaa gtgatcaaaa ttaacgtcac     1620
cagtgataag tcattcagat ttgttctaga taatctttct aaaaattcat aatcccaatc     1680
taattatgag ctaaacatc cagcaaactc aagttgaagg acattctaca aaatatccct     1740
ggggtatttt agagtattcc tcaaaactgt aaaaatcatg gaaataagg gaatcctgag     1800 aaacaatcac agaccacatg agactaagga gacatgtgag ccaaatgcaa tgtgcttctt     1860
ggatcagatc ctggaacaga aaagatcag taatgaaaaa actgatgaag tctgaataga     1920
atctggagta ttttttaacag tagtgttgat ttcttaatct tgacaaatat agcagggtaa     1980
tgtaagatga taacgttaga gaaactgaaa ctgggtgagg gctatctagg aattctctgt     2040
actatcttac caaattttcg gtaagtctaa gaaagcaatg caaaataaaa agtgtcttga     2100
aaaaaaaaaa aaaaaaaaaa aaaaaaaa                                        2128
```

<210> SEQ ID NO 14
<211> LENGTH: 1406
<212> TYPE: DNA
<213> ORGANISM: MUS MUSCULUS

<400> SEQUENCE: 14

```
ctcattctac tctgaagcca gcaccatggc attaatgctt gtgctgttct tcctggctgc       60
tgtactgccc ccatcccttc ttcaagataa ctctcaggag aacagtcttg agaaactttc      120
aaccagtaaa aaatcagtcc aagaagagat tgtaagcaag cacaaccaat tgagacgaaa      180
ggtttctcca tctggcagtg acttactaaa tatggaatgg aactatgatg ctcaagtgaa      240
tgctcagcaa cgggcagaca agtgtacatt cagtcacagt cctatagaac tcaggacaac      300
taatttaaaa tgtggtgaga atttgttcat gtcatcttac cttgtaccat ggtcttctgt      360
aatccaagga tggtataatg aatccaaagg tcttatattt ggtgtgggcc caaagcaaaa      420
```

```
tgttagtgtg gttggacatc atactcaggt tgtttggaaa tcaaatttac aagttgcatg    480
tggagttgct gaatgccctg aaaatccact gagatacttt tatgtttgtc gctattgtcc    540
tgtattgaat tacagtggcc attatccaag caggccatac ctagcttaca cagcaagagc    600
accatgtgcc agttgtcctg atcgctgtga agatggactg tgcaccaaga gttgtcaata    660
taaggatatg tcttttggt gtaaacgtct ggaatacgtc tgtaaacatc caggtcttaa     720
aaaacgttgc ctagctacat gccaatgtta aggcaaaatt cactaaattt cctgtccagg    780
ctgccaggac caagtagaga aaggtcatac tctctagtca ggcttatcac atcccaccaa    840
gaatatatag atttaataca ttggaacaat tccagatggt aaagattctg tttcttcttc    900
tatttctttc tattttgcag atatcattta ccccaaatat tttaaagtaa caaaattgat    960
aataaccttt ggaccttgac atttgaaatc tgtgacacat tcatgaagtc aaatctagcc   1020
aatgactata cattgtctgt atgactaaag tcactaaaac tcatatgact aatgttccaa   1080
gagcacaatg aagtaaggga atagaaaaca tatagttcct gtgtaatggt cagtcatctt   1140
ttgtagctct acctagttaa gtctctctga agaaaattca cattgtcttt ttttttttct   1200
cactattcat tattcttcac attcaacata atcagtggtt taaattctaa aataccattt   1260
acattttagt tgtttttttt tctaagaatg atataaaatg taccttaatg agaagaattt   1320
gcttgttcag gggacaatga cctttgttgc tttagaaaaa aaataaatct taatcttggc   1380
ttattaaaaa aaaaaaaaaa aaaaaa                                         1406
```

CRISP POLYPEPTIDES AS CONTRACEPTIVES AND INHIBITORS OF SPERM CAPACITATION

STATEMENT OF GOVERNMENT RIGHTS

This invention was made with government support under a grant from the National Institutes of Health, Grant No. HD 11962. The U.S. Government has certain rights in this invention.

This application is a national stage filing of International Patent Application No. PCT/US03/16669, filed May 28, 2003, which in turn claims priority to U.S. Provisional Application Ser. No. 60/383,628, filed May 28, 2002, both of which are incorporated herein by reference in their entirety.

BACKGROUND

An effective, safe and easily reversible male contraceptive with universal acceptability remains an elusive goal. Although a variety of approaches for achieving male contraception have been tried, no single mode of male contraception is without its immediate drawbacks for efficacy or compliance. Even seemingly simple interventions have not proven to be widely acceptable. For example, surgical or non-surgical vasectomy, methods that interrupt sperm transport in the male reproductive tract, are not without their complications or long-term risk. More complex approaches, such as regimens for the hormonal control of male fertility, have also not been fully satisfactory. Such methods have focused on the suppression of spermatogenesis to the point of azoospermia, a goal that has been difficult to achieve. The use of the immune response to block contraception has been an important front in efforts to develop more sophisticated contraceptive systems. Unfortunately, such approaches have thus far failed, as male autoimmunity against sperm does not suppress sperm production in men; this is known because such autoimmunity can occur after vasectomy. Thus, inhibiting sperm fertilizing-ability without affecting the hormonal balance in either the male or female remains an important goal in the field of reproductive biology. The present invention achieves this goal.

SUMMARY OF THE INVENTION

The present invention includes a method of inhibiting sperm capacitation including contacting sperm with a CRISP polypeptide. Also included in the present invention is a method of inhibiting sperm capacitation in an individual including the administration of a CRISP polypeptide to the individual.

In another aspect, the present invention also includes a method for inhibiting fertilization of an egg by sperm in an individual, comprising the administration of a CRISP polypeptide to the individual.

In another aspect, the present invention includes a method of inhibiting the phosphorylation of a protein at tyrosine residues including contacting the protein with a CRISP polypeptide. In some embodiments of the present invention, the protein may be on the surface of mammalian sperm.

A further aspect of the present invention includes a method of inhibiting an acrosomal reaction including contacting the acrosomal reaction with a CRISP polypeptide.

In some embodiments of the methods of the present invention, the CRISP polypeptide may be administered orally. In some embodiments of the methods of the present invention, the CRISP polypeptide may be administered parenterally. In some embodiments of the methods of the present invention, the CRISP polypeptide may be administered transdermally. In some embodiments of the methods of the present invention, the CRISP polypeptide may be administered in a composition including a pharmaceutically acceptable carrier.

In some embodiments of the methods of the present invention, the individual may be a mammalian male. In some embodiments of the methods of the present invention, the individual may be a mammalian female. In some embodiments of the methods of the present invention, the CRISP polypeptide may be administered intravaginally, including administered as a time released, vaginal implant. In other embodiments of the methods of the present invention, the CRISP polypeptide is administered to the vagina of the mammalian female in an amount capable of inhibiting sperm capacitation, rendering said sperm incapable of fertilization.

In other embodiments of the methods of the present invention, the CRISP polypeptide has at least about 40% structural identity to a polypeptide selected from the group consisting of human CRISP-1 (SEQ ID NO:1), rat CRISP-1 (SEQ ID NO:2), mouse CRISP-1 (SEQ ID NO:3), human CRISP-2 (SEQ ID NO:4), rat CRISP-2 (SEQ ID NO:5), human CRISP-3 (SEQ ID NO:6), mouse CRISP-3 (SEQ ID NO:7), and biologically active analogs thereof.

In yet other embodiments of the methods of the present invention, the CRISP polypeptide has at least about 40% structural identity to human CRISP-1 (SEQ ID NO:1) or a biologically active analog thereof. In some embodiments of the methods of the present invention, the CRISP polypeptide is human CRISP-1 (SEQ ID NO:1).

In other embodiments of the methods of the present invention, the CRISP polypeptide has about at least 40% structural identity to rat CRISP-1 (SEQ ID NO:2) of a biologically active analog thereof. In some embodiments of the methods of the present invention, the CRISP polypeptide is rat CRISP-1 (SEQ ID NO:2).

Also included in the present invention is a contraceptive composition including a CRISP polypeptide in an amount effective to inhibit sperm capacitation, inhibit phosphorylation of a protein at tyrosine residues, inhibit an acrosome reaction, and/or inhibit fertilization of an egg by sperm. In some embodiments of the contraceptive composition of the present invention, the CRISP polypeptide has at least about 40% structural identity to a polypeptide selected from the group consisting of human CRISP-1 (SEQ ID NO:1, rat CRISP-1 (SEQ ID NO:2), mouse CRISP-1 (SEQ ID NO:3), human CRISP-2 (SEQ ID NO:4), rat CRISP-2 (SEQ ID NO:5), human CRISP-3 (SEQ ID NO:6), mouse CRISP-3 (SEQ ID NO:7) and biologically active analogs thereof. In some embodiments of the contraceptive composition of the present invention, the CRISP polypeptide has at least about 40% structural identity to human CRISP-1 (SEQ ID NO:1) and biologically active analogs thereof. In some embodiments of the contraceptive composition of the present invention, the CRISP polypeptide is human CRISP-1 (SEQ ID NO:1). In some embodiments of the contraceptive composition of the present invention, the CRISP polypeptide has at least about 40% structural identity to rat CRISP-1 (SEQ ID NO:2), and biologically active analogs thereof. In other embodiments of the contraceptive composition of the present invention, the CRISP polypeptide is rat CRISP-1 (SEQ ID NO:2). In some embodiments of the contraceptive composition of the present invention, the contraceptive composition further includes a spermicidal or an antiviral agent.

DETAILED DESCRIPTION OF THE DRAWINGS

FIG. 1. Immunoblot of solubilized rat sperm collected from the end of the epididymis and incubated in a defined capacitation medium in vitro for 5 hours under controlled conditions. A sample of sperm was taken at the beginning of incubation to provide the time zero conditions (lane 1). Aliquots of collected sperm were incubated under the following various conditions: 5 hours under non-capacitation conditions (lane 2); 5 hours under capacitating conditions (lane 3); and 5 hours under capacitating conditions with increasing concentrations of CRISP-1 (lanes 4, 5, and 6). In FIG. 1A, the immunoblot is stained with an anti-phosphotyrosine antibody. FIG. 1B shows the same gel stained with an anti-CRISP-1 antibody.

Figure 2:
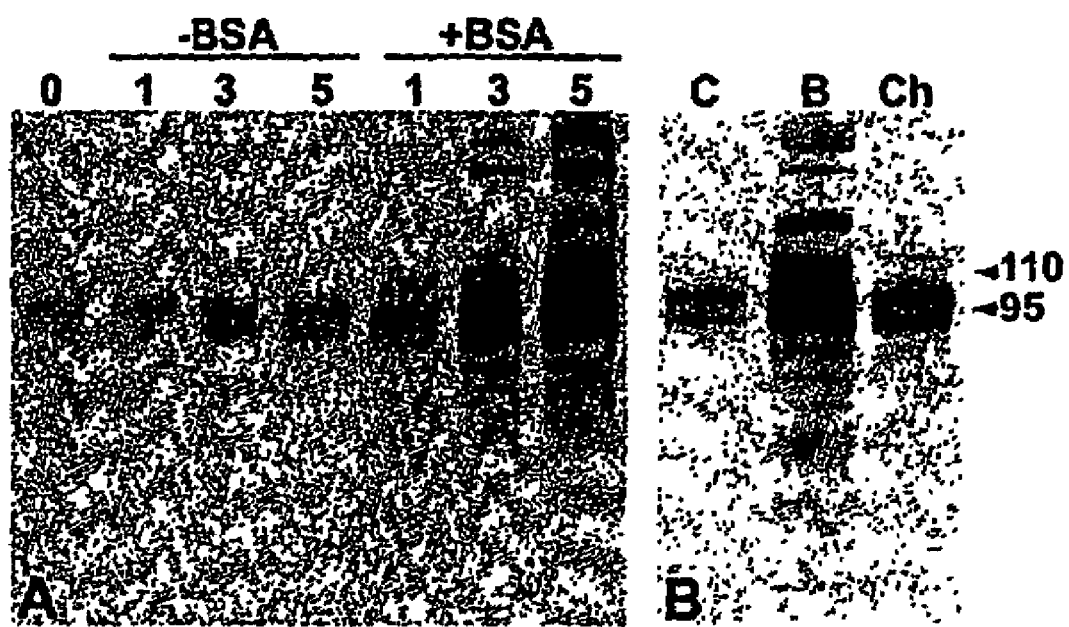

FIG. 2. The requirement of incubating rat sperm with bovine serum albumin (BSA) to achieve the tyrosine phosphorylation associated with capacitation. Rat epididymal sperm were isolated in BWW with (+BSA) or without (−BSA) 15 mg/ml lipid-rich BSA for 5 hours. Aliquots of sperm were checked for tyrosine phosphorylation at 1, 3, and 5 hour time points by western blot analysis using an anti-phosphotyrosine antibody (FIG. 2A). A steady accumulation of tyrosine phosphorylation was observed in the presence of BSA, with negligible phosphorylation in BWW alone. To determine if extraction of cholesterol was the action of the BSA that led to the tyrosine phosphorylation, sperm were incubated with 15 mg/ml BSA with (Ch) or without (B) the addition of 30 µM cholesterol sulfate and tyrosine phosphorylation compared to levels seen in sperm incubated in BWW alone (C). The addition of exogenous cholesterol sulfate eliminated the BSA-induced phosphorylation of sperm proteins (FIG. 2B).

Figure 3:
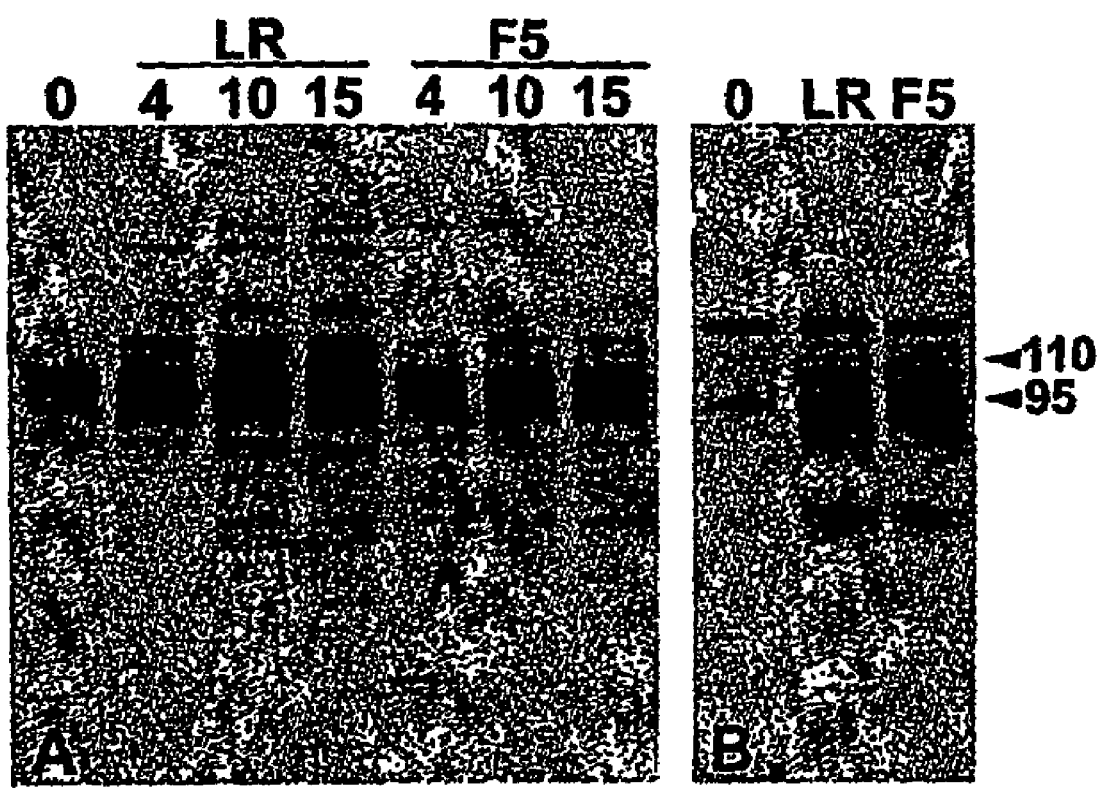

FIG. 3. The comparative activity of lipid-rich BSA and Fraction V BSA in the induction of protein tyrosine phosphorylation of rat and mouse sperm. Rat epididymal sperm were incubated in increasing concentrations of lipid-rich (LR) or Fraction V (F5) BSA and protein tyrosine phosphorylation was determined after 5 hours (FIG. 3A). Both lipid-rich and Fraction V BSA showed maximal induction of phosphorylation at 15 mg/ml, but phosphorylation was greatest in lipid-rich BSA at each concentration. Since Fraction V BSA is routinely used for capacitation studies in other species, 4 mg/ml lipid-rich or Fraction V BSA were tested in capacitation incubations with mouse sperm (FIG. 3B). With mouse sperm, both lipid-rich and Fraction V are equipotent at inducing protein tyrosine phosphorylation.

Figure 4:
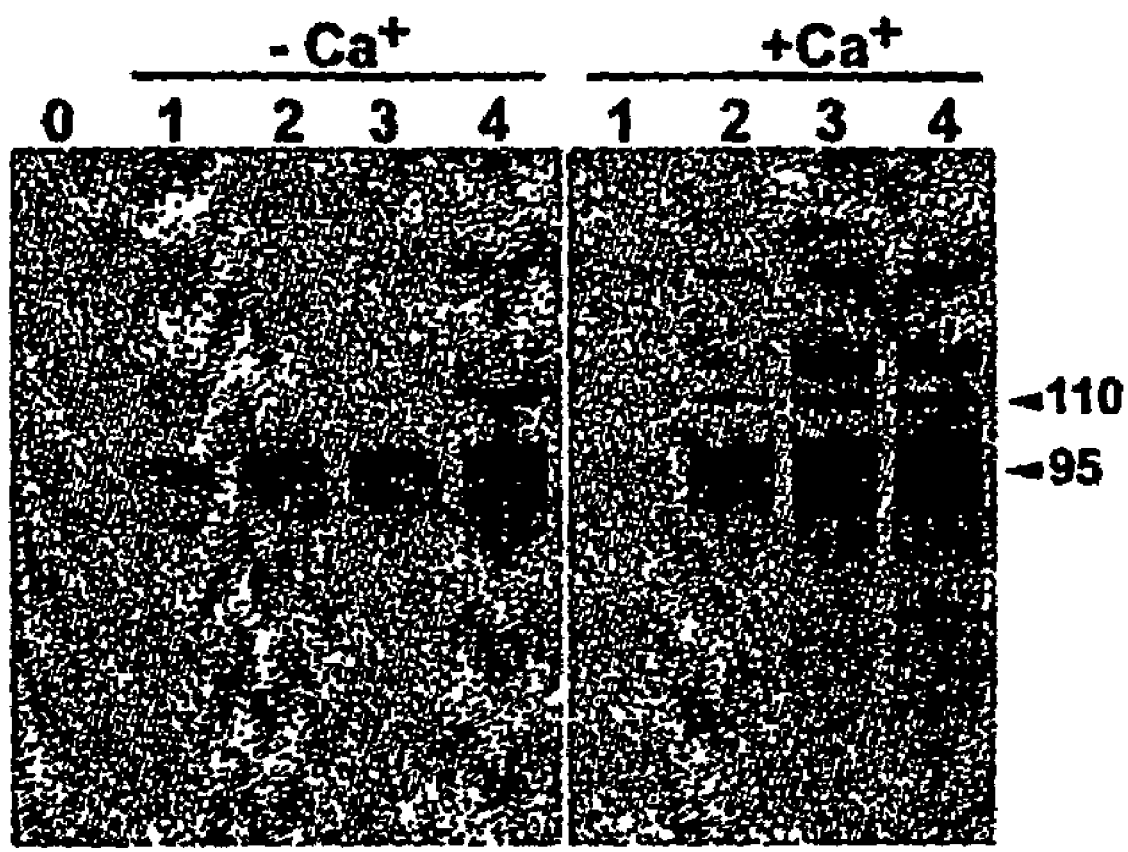

FIG. 4. The requirement of extracellular $Ca^{++}$ for induction of capacitation in rat sperm. Sperm were incubated in BWW solution with ($+Ca^{++}$) or without ($-Ca^{++}$) 1.7 mM $Ca^{++}$. At hourly time points out to 4 hours, sperm were tested for the presence of tyrosine-phosphorylated proteins. The presence of extracellular calcium ion was required for maximal phosphorylation.

Figure 5:
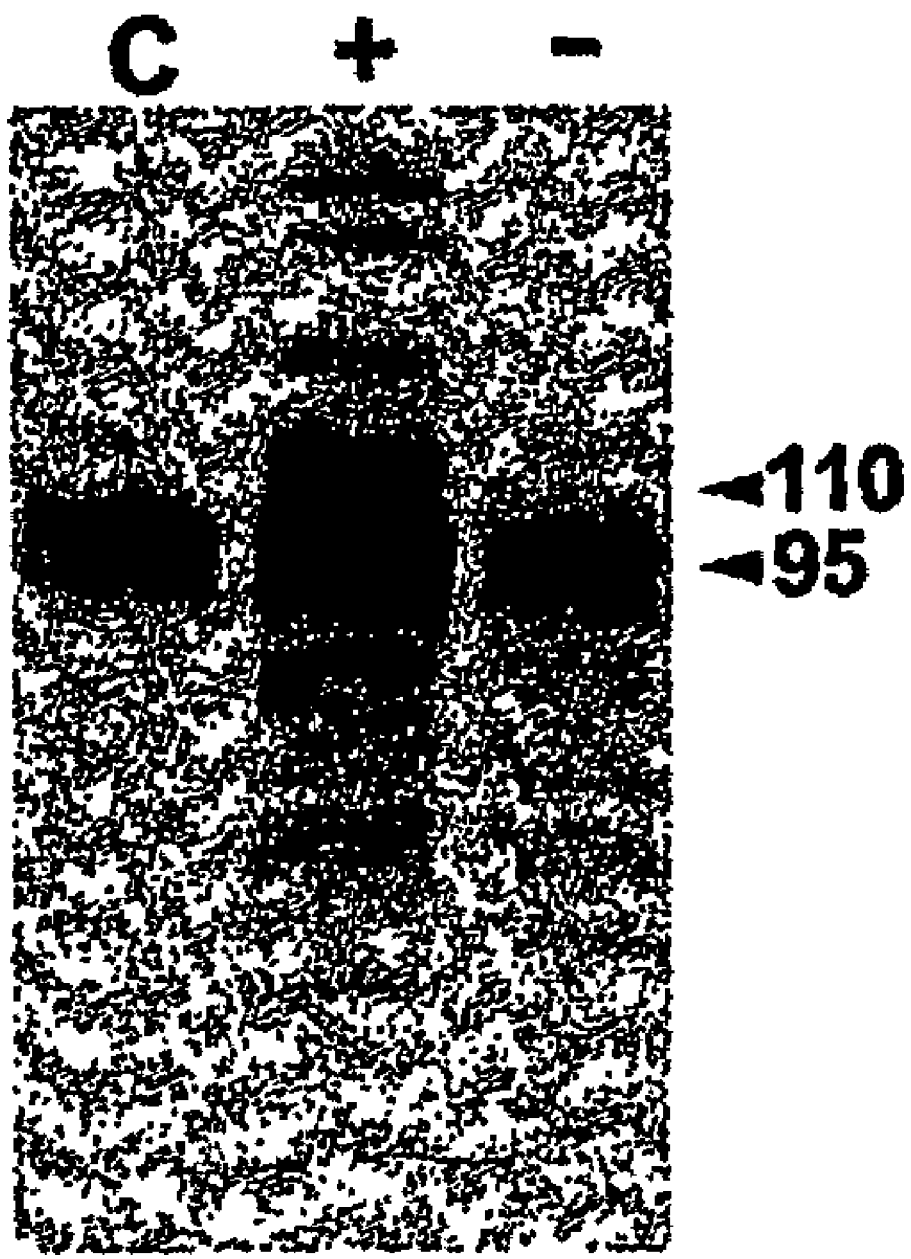

FIG. 5. The requirement of extracellular bicarbonate ion for induction of capacitation in rat sperm. Sperm were incubated in BWW solution with (+) or without (−) 25 mM $HCO_3^-$ for 4 hours and then tested for the presence of tyrosine-phosphorylated proteins. The presence of bicarbonate ion in the media was required for tyrosine phosphorylation of sperm proteins. Omission of bicarbonate resulted in phosphorylation levels the same as BWW alone (C).

Figure 6:
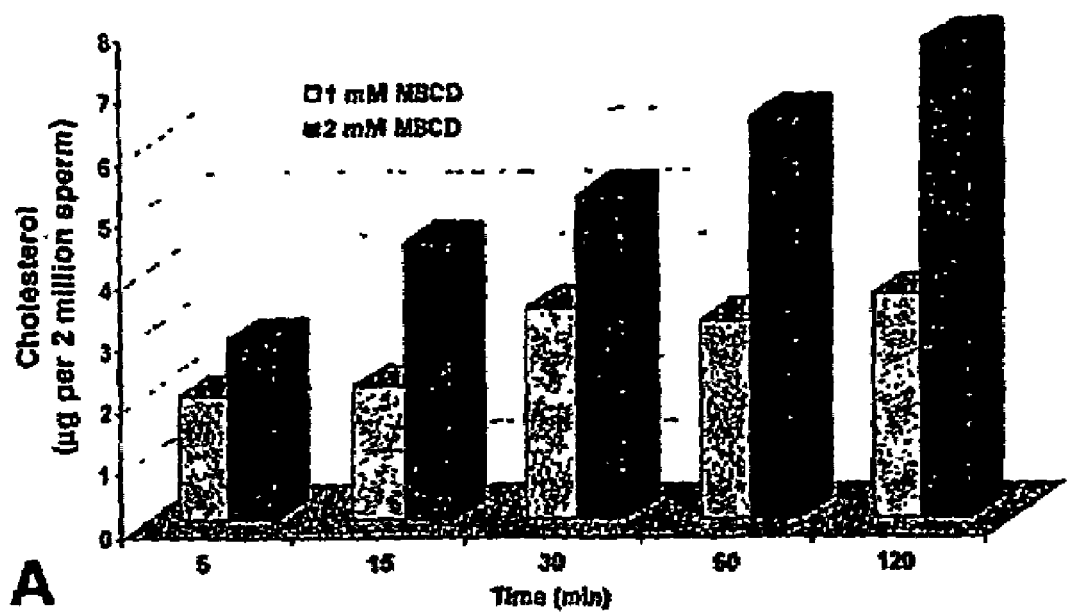
Figure 6:
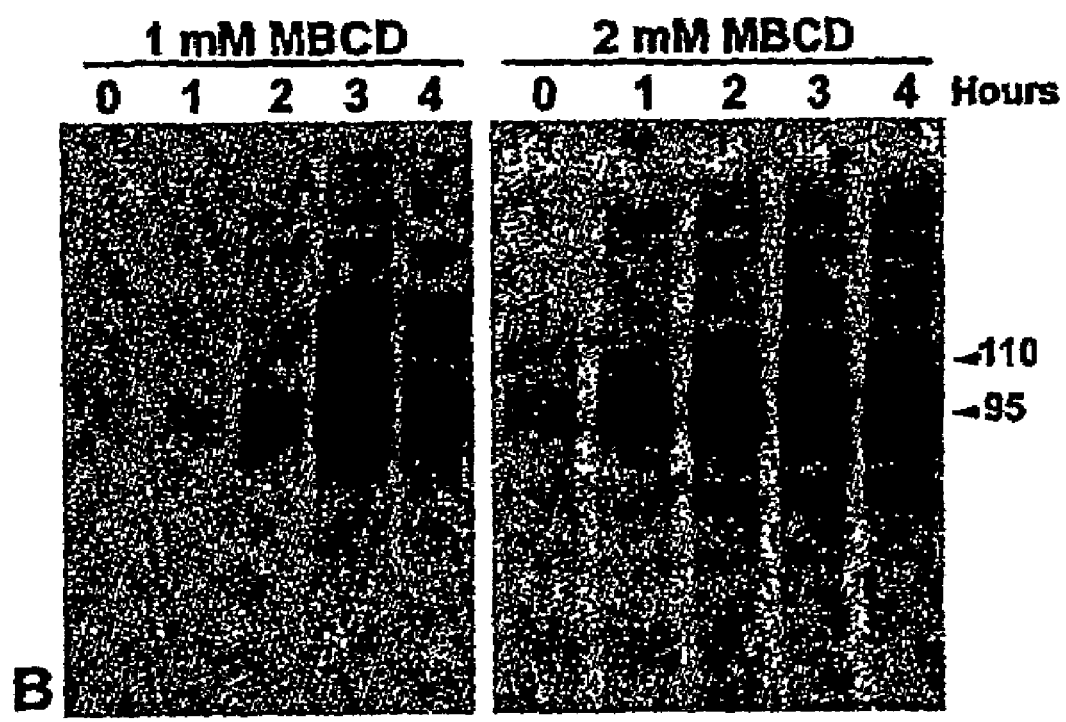

FIG. 6. Quantitative kinetics of cholesterol extraction and protein tyrosine phosphorylation of sperm proteins. Rat epididymal sperm were incubated in 1 or 2 mM methyl-β-cyclodextran (MBCD) and extracted cholesterol measured at time intervals out to 2 hours (FIG. 6A). The levels of cholesterol were determined by the Amplex Red Cholesterol assay and the results normalized to cholesterol extracted in BWW alone. Protein tyrosine phosphorylation was measured by western blot at hourly time points during extraction with MBCD (FIG. 6B). Cholesterol extraction reached a plateau with 1 mM MBCD at 30 minutes and with 2 mM MBCD between 60 and 120 minutes (later time points not shown). Maximal phosphorylation lagged behind maximal cholesterol extraction with both concentrations of MBCD.

Figure 7:
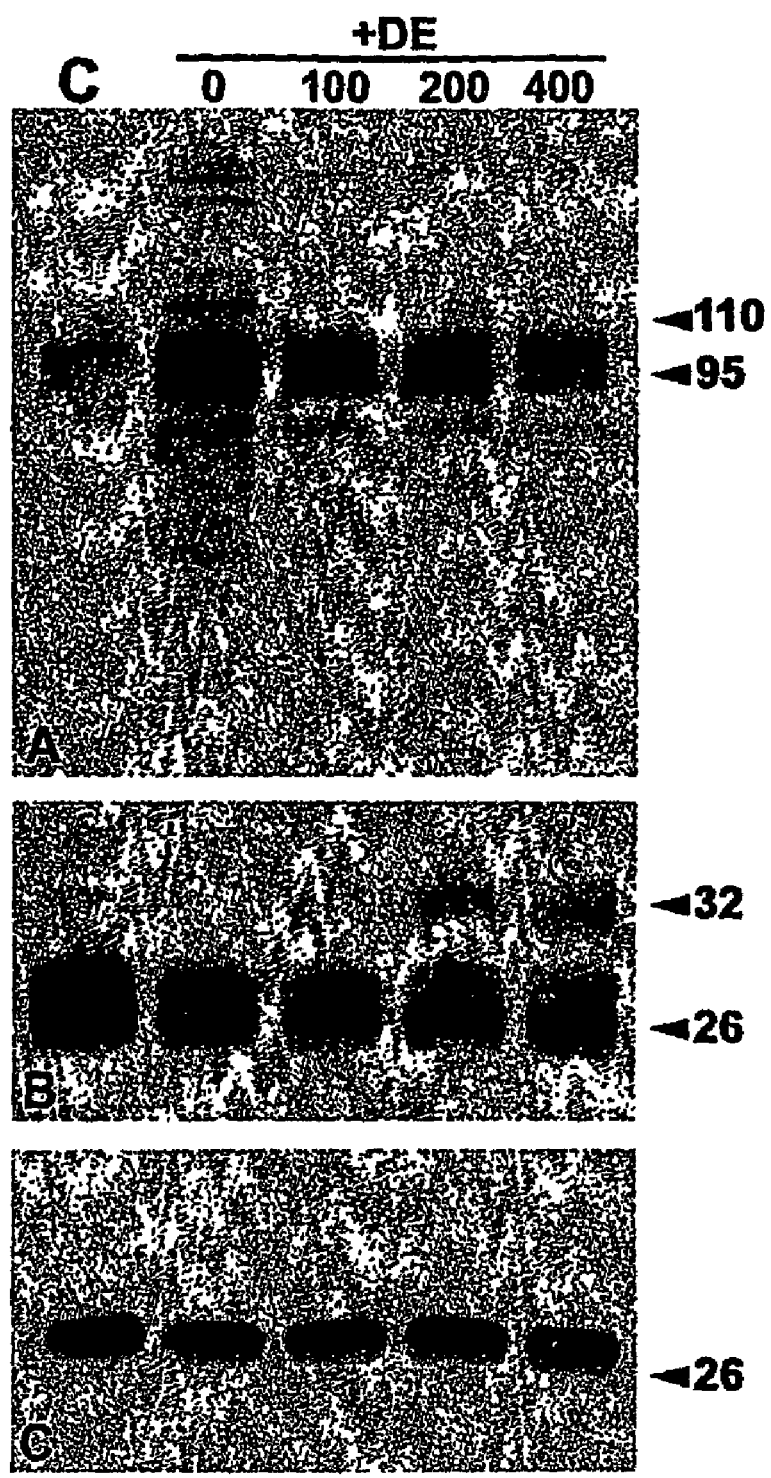

FIG. 7. The effect of incubation of rat epididymal sperm with exogenous purified Crisp-1 on the level of protein tyrosine phosphoryation. Sperm were incubated under capacitating conditions with 15 mg/ml lipid-rich BSA for 5 hours in the presence of increasing concentrations (µg/ml) of purified proteins DE (FIG. 7A). Analysis of cells prior to capacitation incubation are shown as control (C). At 400 µg/ml protein tyrosine phosphorylation was nearly completely inhibited. The same Western blot was stripped and probed with antibody CAP-A (FIG. 7B) and 4E9 (FIG. 7C). Protein detected by CAP-A demonstrates that Crisp-1 re-associates with the sperm in a dose dependent fashion that correlates with the inhibition of capacitation (FIG. 7B). Antibody CAP-A detects all forms of Crisp-1 including processed forms of proteins D and E. Monoclonal antibody 4E9 detects only forms of Protein E (FIG. 7C). Comparison of the staining with 4E9, which stains only a processed form of protein E extracted from the sperm surface, and CAP-A demonstrates that only an unprocessed form of protein D re-associates with sperm to inhibit phosphorylation. The unprocessed Crisp-1 detected by CAP-A is lost with time when the sperm are removed from the exogenous pure Crisp-1 solution, suggesting that unprocessed Crisp-1 associates in a receptor-ligand fashion while processed Crisp-1 is covalently attached to the sperm surface.

Figure 8:
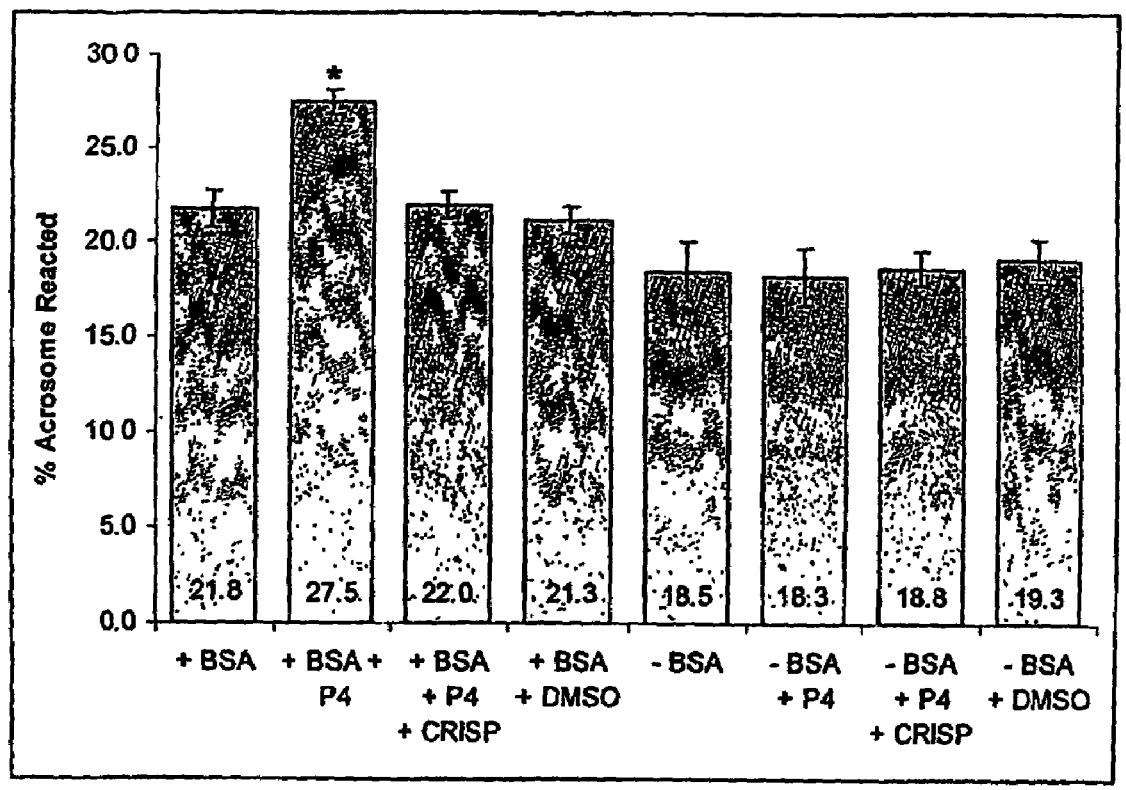

FIG. 8. The effect of incubation of rat epididymal sperm with exogenous purified Crisp-1 on the level of progesterone induced acrosome reaction. Sperm were incubated under capacitating conditions for 1 hours in the presence or absence of 400 µg/ml Crisp-1. Progesterone (P4) at 1 µM was added to sperm after 30 minutes of incubation to induce the acrosome reaction. DMSO, the solvent used for the P4 stock solution, was added to control cells. Addition of P4 to capacitated sperm (+BSA+P4) caused a statistically significant (*P<0.05) increase in acrosome reacted sperm compared to capacitated sperm (+BSA or +BSA+DMSO). This increase is completely abolished by addition of exogenous Crisp-1 (+BSA+P4+CRISP-1), as evidenced by the statistically significant decrease (*P<0.05) in acrosome reacted sperm. Columns are shown with values at base. The percent acrosome reacted sperm in the +BSA+P4 group was significantly higher (*P<0.05) than all other groups and there was no significant difference in the percent acrosome reacted sperm between any of the other groups. Data are presented as means +/−SEM.

Figure 9:
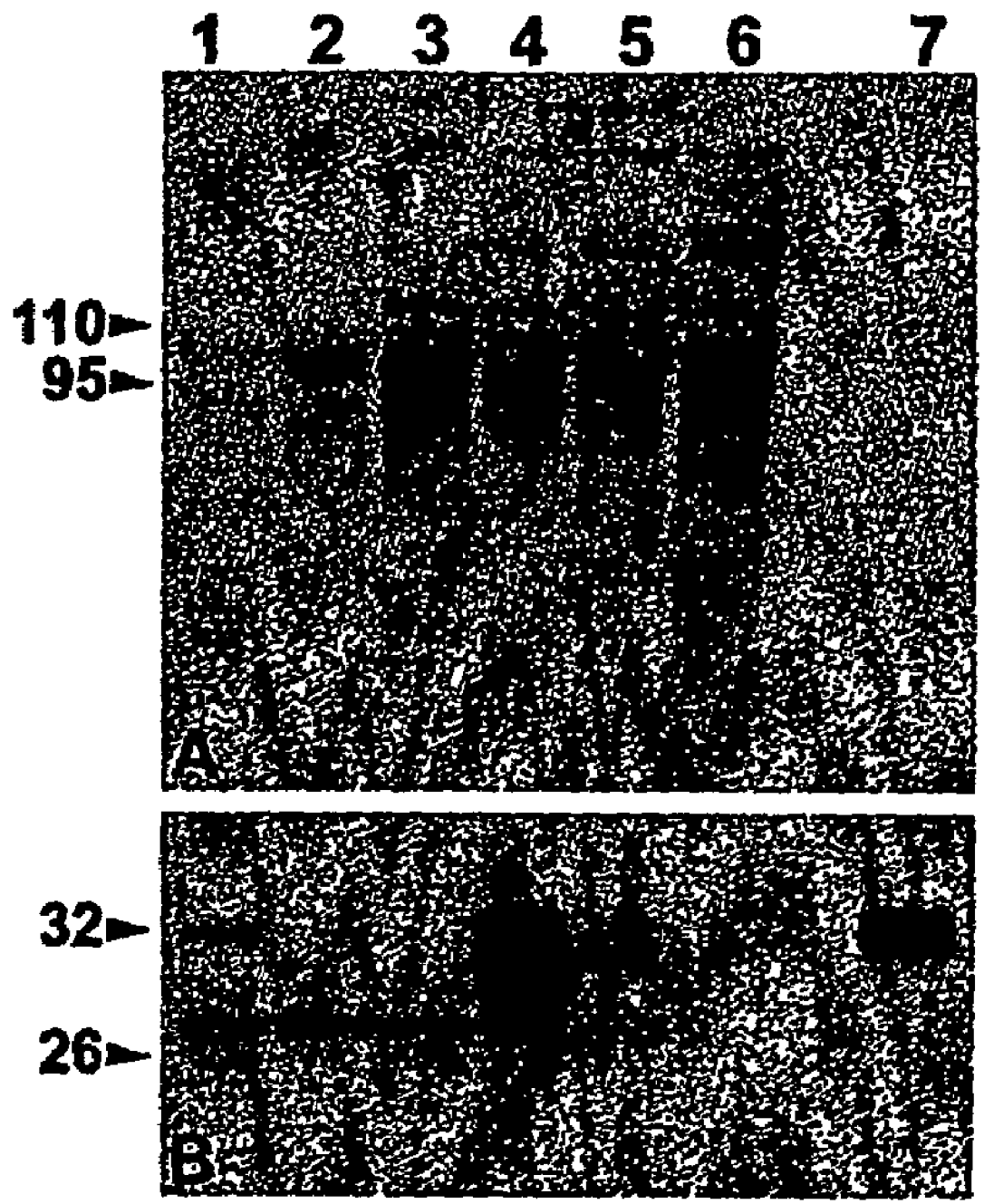

FIG. 9. The reversibility of protein tyrosine phosphoryation inhibition by exogenous purified Crisp-1 in rat epididymal sperm. Sperm were incubated under capacitating conditions with 15 mg/ml lipid-rich BSA for 5 hours in the presence (lane 4) or absence (lane 3) of 200 µg/ml Crisp-1. At 5 hours sperm were washed free of exogenous Crisp-1 and incubated for an additional 3 (lane 5) or 19 (lane 6) hours. Sperm at time zero and after 5 hours in BWW without BSA are shown in lanes 1 and 2, respectively. Sperm proteins were analyzed by western blot analysis for protein tyrosine phosphorylation (FIG. 9A) and Crisp-1 (FIG. 9B). As shown previously, 200 µg/ml Crisp-1 has an inhibitory effect on sperm protein tyrosine phosphorylation. The inhibition of protein tyrosine phosphorylation was reversed with the removal of Crisp-1. Exogenous Crisp-1 associated with sperm after 5 hours incubation is lost from the surface of sperm with time. An aliquot of purified Crisp-1 used in the sperm incubations is shown in lane 7.

Figure 10:
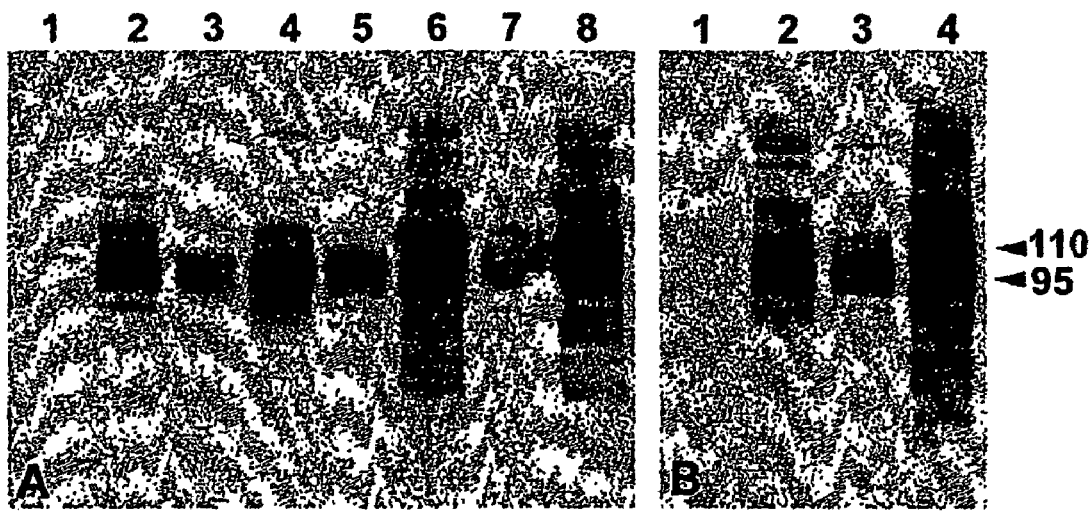

FIG. 10. Effect of exogenous administration of cAMP analog, dibromo-cAMP (db-cAMP), and the phosphodiesterase inhibitor IBMX on the protein tyrosine phosphorylation associated with capacitation. To determine if BSA, $Ca^{++}$, and $HCO_3^-$ act upstream of cAMP in the signaling cascade that leads to protein tyrosine phosphorylation (FIG. 10A), sperm were incubated in the presence (lanes 4, 6, 8) or absence (lanes 3, 5, 7) of db-cAMP/IBMX without BSA (lanes 3, 4), $Ca^{++}$ (lanes 5, 6), or $HCO_3^-$ (lanes 7, 8). Control phosphorylation in BWW or BWW with BSA are shown in lanes 1 and 2, respectively. In each case, exogenous cAMP and IBMX overcome the block to phosphorylation caused by omission of BSA, $Ca^{++}$, or $HCO_3^-$ from the capacitation medium, indicating that cAMP acts downstream for the effect of these three required constituents of capacitation. The ability of cAMP to overcome the inhibition of phosphorylation by Crisp-1 was tested by incubating sperm under capacitating conditions with and without db-cAMP/IBMX in the presence of 400 µg/ml pure Crisp-1 (lanes 3 & 4, respectively, FIG. 10B). Control sperm in BWW only or BWW with BSA are shown in lanes 1 and 2, respectively. The results show that the block to phosphorylation caused by Crisp-1 is also upstream of the effect of cAMP on protein tyrosine phosphorylation.

FIG. 11. Amino acid sequence of human CRISP-1 (SEQ ID NO:1), rat CRISP-1 (SEQ ID NO:2), mouse CRISP-1 (SEQ ID NO:3), human CRISP-2 (SEQ ID NO:4), rat CRISP-2 (SEQ ID NO:5), human CRISP-3 (SEQ ID NO:6) and mouse CRISP-3 (SEQ ID NO7).

FIG. 12. cDNA sequences encoding human CRISP-1 (SEQ ID NO:8), rat CRISP-1 (SEQ ID NO:9), mouse CRISP-1 (SEQ ID NO:10), human CRISP-2 (SEQ ID NO:11), rat CRISP-2 (SEQ ID NO:12), human CRISP-3 (SEQ ID NO:13) and mouse CRISP-3 (SEQ ID NO:14).

DETAILED DESCRIPTION OF PREFERRED EMBODIMENTS

With the present invention it has been demonstrated that a CRISP polypeptide inhibits sperm capacitation, inhibits protein phosphorylation at tyrosine residues, and inhibits the acrosomal reaction. Thus, CRISP polypeptides can be used in improved methods of contraception, without affecting or interfering with the hormonal or immune systems. The CRISP polypeptides of the present invention include naturally occurring CRISP polypeptides and biologically active analogs thereof.

Naturally occurring CRISP polypeptides comprise a family of Cysteine-RIch Secretory Proteins that are expressed in numerous organs in male animals, particularly in the reproductive tract. CRISP polypeptides are not generally expressed in female animals, with the exception of neutrophils, and possibly in tumors. In the male, CRISP-1 is expressed primarily in the epididymis, CRISP-2 is expressed primarily in the testis and CRISP-3 is expressed primarily in salivary glands. Prostate and seminal vesicles also have low expression of some of these proteins. Sperm require passage through the epididymis before they are able to fertilize an egg. This passage is an obligatory maturational process in the male and during this time, CRISP-1, a secretory product of the epididymis, is added to the sperm surface. When sperm are ejaculated into the female reproductive tract they under go a process called "capacitation," which is required as the final maturational step before interaction between sperm and egg. It is well recognized that sperm that are not capacitated win not fertilize. Thus, the identification of agents that inhibit capacitation will lead to development of improved contraceptives.

The CRISP family of polypeptides has been extensively characterized and the amino acid sequences of the CRISP-1, CRISP-2 and CRISP-3 polypeptides from a number of species are known. The CRISP-1 polypeptides from human (Kratzschmar et al., *Eur. J. Biochem.* 236(3):827-36, 1996), rat (Klemme et al., *Gene* 240(2):279-88, 1999; Charest et al., *Mol. Endocrinol.* 2 (10), 999-1004, 1988; Brooks et al., *Eur. J. Biochem* 161(1):13-18, 1986), and mouse (Eberspaecher et al., *Mol. Reprod. Dev.* 42:157-172, 1995; Haendler et al., *Endocrinology* 133 (1), 192-198, 1993) have been characterized. The human CRISP-1 amino acid sequence (SEQ ID NO:1) is available as Genbank Accession Number CAA64524, the rat CRISP-1 amino acid sequence (SEQ ID NO:2) is available as Genbank Accession Number AAD41529, and the mouse CRISP-1 amino acid sequence (SEQ ID NO:3) is available as Genbank Accession A49202, all of which are shown in FIG. 11. The cDNA sequence encoding human CRISP-1 (SEQ ID NO:8) is available as Genbank Accession Number X95237, the cDNA sequence encoding rat CRISP-1 (SEQ ID NO:9) is available as Genbank Accession Number NM_022859, and the cDNA sequence encoding mouse CRISP-1 (SEQ ID NO:10) is available as Genbank Accession Number L05559, all of which are shown in FIG. 12.

The CRISP-2 polypeptides from human (Kratzschmar et al., *Eur. J. Biochem.* 236 (3), 827-836, 1996) and rat (O'Bryan et al., *Mol. Reprod. Dev.* 50 (3), 313-322, 1998) have been characterized. The human CRISP-2 amino acid sequence (SEQ ID NO:4), available as Genbank Accession Number P16562, and the rat CRISP-2 amino acid sequence (SEQ ID NO:5), available as Genbank Accession Number AAD48090, are shown in FIG. 11. The cDNA sequence encoding human CRISP-2 (SEQ ID NO:11) is available as Genbank Accession Number X95239 and the cDNA sequence encoding rat CRISP-2 (SEQ ID NO:12) is available as Genbank Accession Number AF078552, all of which are shown in FIG. 12.

The CRISP-3 polypeptides from human (Kratzschmar et al., *Eur. J. Biochem.* 236 (3), 827-836, 1996) and mouse (Haendler et al., *Endocrinology* 133 (1), 192-198 (1993)) have been characterized. The human CRISP-3 amino acid sequence (SEQ ID NO:6), available as Genbank Accession Number P54108, and the mouse CRISP-3 amino acid sequence (SEQ ID NO:7), available as Genbank Accession Number Q03402, are shown in FIG. 11. The cDNA sequence encoding human CRISP-3 (SEQ ID NO:13) is available as Genbank Accession Number X95240 and the cDNA sequence encoding mouse CRISP-3 (SEQ ID NO:14) is available as Genbank Accession Number L05560, all of which are shown in FIG. 12.

The CRISP polypeptides of the present invention may be derived from a variety of species, including, but not limited to, human, primate, rat, mouse, bovine, and horse. The CRISP polypeptides of the present invention include, but are not limited to, CRISP-1, CRISP-2 and CRISP-3 polypeptides. For example, the CRISP polypeptides of the present invention include, but are not limited to, human CRISP-1 (SEQ ID NO:1), rat CRISP-1 (SEQ ID NO:2), mouse CRISP-1 (SEQ ID NO:3), human CRISP-2 (SEQ ID NO:4), rat CRISP-2 (SEQ ID NO:5), human CRISP-3 (SEQ ID NO:6), and mouse CRISP-3 (SEQ ID NO:7).

"Polypeptide" as used herein refers to a polymer of amino acids and does not refer to a specific length of a polymer of amino acids. Thus, for example, the terms peptide, oligopeptide, protein, and enzyme are included within the definition of polypeptide, whether naturally occurring or synthetically derived, for instance, by recombinant techniques or chemically or enzymatically synthesized. This term also includes post-expression modifications of the polypeptide, for example, glycosylations, acetylations, phosphorylations, and the like. The following abbreviations are used throughout the application:

A=Ala=Alanine
V=Val=Valine
L=Leu=Leucine
I=Ile=Isoleucine
P=Pro=Proline
F=Phe=Phenylalanine
W=Trp=Tryptophan
M=Met=Methionine
G=Gly=Glycine
S=Ser=Serine
T=Thr=Threonine
C=Cys=Cysteine
Y=Tyr=Tyrosine
N=Asn=Asparagine
Q=Gln=Glutamine
D=Asp=Aspartic Acid
E=Glu=Glutamic Acid
K=Lys=Lysine
R=Arg=Arginine
H=His=Histidine As used herein, a CRISP polypeptide also includes "biologically active analogs" of naturally occurring CRISP polypeptides. For example, the CRISP polypeptides of the present invention include, but are not limited to, biologically active analogs of human CRISP-1 (SEQ ID NO:1), rat CRISP-1 (SEQ ID NO:2), mouse CRISP-1 (SEQ ID NO:3), human CRISP-2 (SEQ ID NO:4), rat CRISP-2 (SEQ ID NO:5), human CRISP-3 (SEQ ID NO:6), or mouse CRISP-3 (SEQ ID NO:7).

As used herein to describe a CRISP polypeptide, the term "biologically active" means to inhibit protein tyrosine phosphorylation, inhibit sperm capacitation, inhibit an acrosome reaction, and/or inhibit fertilization of an egg by sperm. Biological activity of a CRISP polypeptide can be easily assessed using the various assays described herein as well as other assays well known to one with ordinary skill in the art. An inhibition in biological activity can be readily ascertained by the various assays described herein, and by assays known to one of skill in the art. An inhibition in biological activity can be quantitatively measured and described as a percentage of the biological activity of a comparable control. The biological activity of the present invention includes an inhibition that is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 99%, at least about 100%, at least about 110%, at least about 125%, at least about 150%, at least about 200%, at least or about 250% of the activity of a suitable control.

A "biologically active analog" of a CRISP polypeptide includes polypeptides having one or more amino acid substitutions that do not eliminate biological activity. Substitutes for an amino acid in the polypeptides of the invention may be selected from other members of the class to which the amino acid belongs. For example, it is well-known in the art of protein biochemistry that an amino acid belonging to a grouping of amino acids having a particular size or characteristic (such as charge, hydrophobicity and hydrophilicity) can be substituted for another amino acid without altering the activity of a protein, particularly in regions of the protein that are not directly associated with biological activity. Substitutes for an amino acid may be selected from other members of the class to which the amino acid belongs. For example, nonpolar (hydrophobic) amino acids include alanine, leucine, isoleucine, valine, proline, phenylalanine, tryptophan, and tyrosine. Polar neutral amino acids include glycine, serine, threonine, cysteine, tyrosine, asparagine and glutamine. The positively charged (basic) amino acids include arginine, lysine and histidine. The negatively charged (acidic) amino acids include aspartic acid and glutamic acid. Examples of such preferred conservative substitutions include Lys for Arg and vice versa to maintain a positive charge; Glu for Asp and vice versa to maintain a negative charge; Ser for Thr so that a free —OH is maintained; and Gln for Asn to maintain a free NH2. Likewise, biologically active analogs of a CRISP polypeptide containing deletions or additions of one or more contiguous or noncontiguous amino acids that do not eliminate the biological activity of the CRISP polypeptide are also contemplated.

A "biologically active analog" of a CRISP polypeptide includes "fragments" and "modifications" of a CRISP polypeptide. As used herein, a "fragment" of a CRISP polypeptide means a CRISP polypeptide that has been truncated at the N-terminus, the C-terminus, or both. The CRISP protein family is characterized by sixteen-conserved cysteine residues located within the C-terminus of the polypeptide. A "fragment" of a CRISP polypeptide may include 1, 2, 3, 4, 5 6, 7, 8, 9, 10, 11, 12, 13, 14, 15, or 16 of the conserved cysteine residues of the CRISP protein family. A fragment may range for about 5 to about 250 amino acids in length. For example it may be about 5, about 10, about 20, about 25, about 50, about 75, about 100, about 125, about 150, about 175, about 200, about 225, or about 250 amino acids in length. Fragments of a CRISP polypeptide with potential biological activity can be identified by many means. One means of identifying such fragments of a CRISP polypeptide with biological activity is to compare the amino acid sequences of a CRISP polypeptide from rat, mouse, human and/or other species to one another. Regions of homology can then be prepared as fragments.

A "modification" of a CRISP polypeptide includes CRISP polypeptides or fragments thereof chemically or enzymatically derivatized at one or more constituent amino acid, including side chain modifications, backbone modifications, and N- and C-terminal modifications including acetylation, hydroxylation, methylation, amidation, and the attachment of carbohydrate or lipid moieties, cofactors, and the like. Modified polypeptides of the invention may retain the biological activity of the unmodified polypeptide or may exhibit a reduced or increased biological activity.

The CRISP polypeptides and biologically active analogs thereof of the present invention include native (naturally occurring), recombinant, and chemically or enzymatically synthesized polypeptides. For example, the CRISP polypeptides of the present invention may be prepared following the procedures for the isolation of CRISP-1 polypeptide from rat sperm detailed by Hall and Tubbs (*Prep. Biochem. Biotechnol.* 27(4):239-51, 1997). For example, the CRISP polypeptides of the present invention can be prepared recombinantly, by well known methods, including, for example, preparation as fusion proteins in bacteria and insect cells.

As used herein, the term "isolated" means that a polynucleotide or polypeptide is either removed from its natural environment or synthetically derived, for instance by recombinant techniques, or chemically or enzymatically synthesized. An isolated polynucleotide denotes a polynucleotide that has been removed from its natural genetic milieu and is thus free of other extraneous or unwanted coding sequences, and is in a form suitable for use within genetically engineered protein production systems. Isolated polynucleotides of the present invention are free of other coding sequences with which they are ordinarily associated, but may include naturally occurring 5' and 3' untranslated regions such as promoters and terminators. Preferably, the polynucleotide or polypeptide is purified, i.e., essentially free from any other polynucleotides or polypeptides and associated cellular products or other impurities.

As used herein, "structural similarity" refers to the identity between two polypeptides. Structural similarity is generally determined by aligning the residues of the two polypeptides to optimize the number of identical amino acids along the lengths of their sequences; gaps in either or both sequences are permitted in making the alignment in order to optimize the number of identical amino acids, although the amino acids in each sequence must nonetheless remain in their proper order. For example, polypeptides may be compared using the Blastp program of the BLAST 2 search algorithm, as described by Tatusova et al. (*FEMS Microbiol. Lett.,* 174; 247-250, 1999) and available on the world wide web at ncbi.nlm.nih.gov/BLAST/. The default values for all BLAST 2 search parameters may be used, including matrix=BLOSUM62; open gap penalty=11, extension gap penalty=1, gap x_dropoff=50, expect=10, wordsize=3, and filter on. In the comparison of two amino acid sequences using the BLAST search algorithm, structural similarity may be referred to by percent "identity" or may be referred to by percent "similarity." "Identity" refers to the presence of identical amino acids and "similarity" refers to the presence of not only identical amino acids but also the presence of conservative substitutions.

The CRISP polypeptides of the present invention include polypeptides with at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% structural identity to a known rat, mouse or human CRISP polypeptide. The CRISP polypeptides of the present invention also include polypeptides with at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% structural similarity to a known rat, mouse or human CRISP polypeptide.

For example, the CRISP polypeptides of the present invention may include, but are not limited to, polypeptides with at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% structural identity to human CRISP-1 (SEQ ID NO:1), rat CRISP-1 (SEQ ID NO:2), or mouse CRISP-1 (SEQ ID NO:3). For example, the CRISP polypeptides of the present invention may also include, but are not limited to, polypeptides with at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% structural similarity to human CRISP-1 (SEQ ID NO:1), rat CRISP-1 (SEQ ID NO:2), or mouse CRISP-1 (SEQ ID NO:3).

According to the present invention, a CRISP polypeptide, including biologically active analogs thereof, can be administered to a subject in an effective amount sufficient to inhibit protein phosphorylation at tyrosine residues, inhibit sperm capacitation, inhibit an acrosome reaction, and/or inhibit the fertilization of an egg by sperm. The CRISP polypeptides of the present invention may be administered to a male or female individual. The individual may be a mammal, including, but not limited to a mouse, rat, primate, bovine, or human. For example, in one embodiment of the present invention, a CRISP-1 polypeptide, or a biologically active analog thereof, can be administered to a subject in an effective amount sufficient to inhibit protein phosphorylation at tyrosine residues, inhibit sperm capacitation, inhibit an acrosome reaction, and/or inhibit the fertilization of an egg by sperm.

As used herein an "acrosome reaction" or "acrosomal reaction" includes the sequence of structural changes that occur in spermatozoa when in the vicinity of an oocyte. Such structural changes serve to facilitate entry of a spermatozoon into the oocyte and include the fusion of portions of the outer membrane of the acrosome with the plasma membrane of the sperm head, creating openings through which the enzymes of the acrosome are released. See, for example, Wasserman et al., *Nat. Cell Biol.* 3:9-14, 2001.

By the term "effective amount" of an agent as provided herein is meant a nontoxic but sufficient amount of the agent or composition to provide the desired effect. Thus, in the context of the present invention, an "effective amount" of a CRISP polypeptide is an amount sufficient to inhibit protein phosphorylation at a tyrosine residue, inhibit sperm capacitation, inhibit an acrosome reaction, and/or affect contraception. The exact amount required will vary from subject to subject, depending on the species, age, and general condition of the subject, the severity of the condition being treated, and the particular agent and its mode of administration, and the like. Thus, it is not possible to specify an exact "effective amount." However, an appropriate effective amount may be determined by one of ordinary skill in the art using only routine experimentation. Therapeutically effective concentrations and amounts may be determined for each application herein empirically by testing the compounds in known in vitro and in vivo systems, such as those described herein; dosages for humans or other animals may then be extrapolated therefrom.

In some embodiments of the present invention, a CRISP polypeptide may be delivered by intravaginal administration. For such administration, a CRISP polypeptide may be provided as a cream gel, foam, emulsion, suppository, and the like. In certain embodiments of the present invention, CRISP polypeptides may be contained within a time released vaginal implant.

In some embodiments of the present invention, a CRISP polypeptide may be delivered by oral administration. For such oral administration, a CRISP polypeptide may be provided as a liquid, a tablet, a pill, a capsule, a gel coated tablet, a syrup, or some other oral administration method. In certain embodiments of the present invention, CRISP polypeptides may be contained within a bio-erodible matrix for time-controlled release.

In some embodiments of the present invention, a CRISP polypeptide may be delivered by transdermal administration. For such administration, a CRISP polypeptide may be provided as a cream, a transdermal patch, and the like. In certain embodiments of the present invention, CRISP polypeptides may be contained within a time released composition.

In some embodiments of the present invention, a CRISP polypeptide may be delivered by parenteral administration.

For such administration, a CRISP polypeptide may by provided in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intraperitoneal, and intratumoral administration. In this connection, sterile aqueous media that can be employed will be known to those of skill in the art in light of the present disclosure (see for example, "Remington's Pharmaceutical Sciences" 15th Edition). Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA.

In some aspects, the present invention includes contraceptive compositions including an effective amount of a CRISP polypeptide, or a biologically active analog thereof, in an amount effective to inhibit sperm capacitation, inhibit protein tyrosine phosphorylation, inhibit an acrosome reaction, and/or effect contraception. These contraceptive compositions may contain one or more active agents. For example, such contraceptive compositions may include, one or more CRISP polypeptides. Such contraceptive compositions may include one or more additional active agents that are not a CRISP polypeptide. Such active agents may include, but are not limited to, spermicidal agents and/or antiviral agents.

The CRISP polypeptides of the present invention may be administered at once, or may be divided into a number of smaller doses to be administered at intervals of time. It is understood that the precise dosage and duration of treatment is a function of the desired therapeutic outcome and may be determined empirically using known testing protocols or by extrapolation from in vivo or in vitro test data. It is to be noted that concentrations and dosage values may also vary with the severity of the condition to be treated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods. The agents of the present invention may be administered to the subject in combination with other modes of contraception. The agents of the present invention can be administered before, during or after the administration of the other therapies.

The CRISP polypeptides of the present invention may be formulated in a composition along with a "carrier." As used herein, "carrier" includes any and all solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

By "pharmaceutically acceptable" is meant a material that is not biologically or otherwise undesirable, i.e., the material may be administered to an individual along with a CRISP polypeptide without causing any undesirable biological effects or interacting in a deleterious manner with any of the other components of the pharmaceutical composition in which it is contained.

A "subject" or an "individual" is an organism, including, for example, a mammal. A mammal may include, for example, a rat, mouse, a primate, a domestic pet, such as, but not limited to, a dog or a cat, livestock, such as, but not limited to, a cow, a horse, and a pig, or a human. Subject also includes model organisms, including, for example, animal models, used to study fertilization of an egg by sperm, sperm capacitation, protein tyrosine phosphorylation, or the acrosome reaction.

A "control" sample or subject is one in which a CRISP pathway has not been manipulated in any way.

As used herein in vitro is in cell culture, ex vivo is a cell that has been removed from the body of a subject and in vivo is within the body of a subject. Unless otherwise specified, "a," "an," "the," and "at least one" are used interchangeably and mean one or more than one.

The present invention also includes an isolated molecule, the molecule being present on the sperm plasma membrane and binds to a CRISP polypeptide. The molecule may be an isolated component of a calcium channel or a receptor involved in calcium channel signaling. For example, the isolated molecule may be a molecule being present on the sperm plasma membrane and binds to a CRISP-1 polypeptide, or a biologically active analog, fragment, or modification thereof. This molecule that binds to a CRISP-1 polypeptide may be an isolated component of a calcium channel or a receptor involved in calcium channel signaling.

EXAMPLES

The present invention is illustrated by the following example. It is to be understood that the particular example, materials, amounts, and procedures are to be interpreted broadly in accordance with the scope and spirit of the invention as set forth herein.

Example 1

Role of CRISP Proteins in the Regulation of Sperm Capacitation and Use in Contraception The results of Example 1 are shown in FIG. 1. Rat sperm were collected from the end of the epididymis and incubated in a defined capacitation medium in vitro for 5 hours under controlled conditions. A sample of sperm was taken at the beginning of incubation to provide the time zero conditions (lane 1 of FIG. 1). Aliquots of collected sperm were incubated under the following various conditions:

For 5 hours under non-capacitation conditions (lane 2 of FIG. 1)

For 5 hours under capacitating conditions (lane 3 of FIG. 1)

For 5 hours under capacitating conditions with increasing concentrations of CRISP-1 (lanes 4, 5 and 6 of FIG. 1).

At the end of incubation, sperm were solubilized and solubilized sperm proteins were separated by SDS gel electrophoresis. Proteins were then transblotted onto a membrane and treated with a primary anti-phosphotyrosine antibody. The results of this anti-phosphotyrosine western blot are shown in FIG. 1A. After recording the results with the anti-phosphotyrosine antibody, the transblot was striped of antibodies and re-probed with an antibody against CRISP-1. The results of this anti-CRISP-1 western blot are shown as FIG. 1B.

FIG. 1A shows phosphotyrosine distribution in sperm under the various incubation conditions. Under non-capacitating conditions, there appears to be some phosphorylation activity. This phosphorylation activity is significantly increased under capacitation conditions, with numerous different proteins exhibiting phosphorylation. Phosphorylation activity is inhibited on many proteins by the addition of CRISP-1. FIG. 1B shows the same gel stained with an anti-CRISP-1 antibody. In lane 1 (time zero) one can see two bands (the D form and the E form of CRISP-1). Under both non-capacitating and capacitating conditions, the D form of CRISP-1 is lost from sperm (see lanes 2 and 3). When CRISP-1 is added back (see lanes 4, 5 and 6), the D form re-appears in a dose-dependent fashion. The E form, which is also present in the added CRISP-1 protein, remains constant under all experimental conditions.

Thus, the addition of CRISP-1 to the capacitating incubation medium inhibits protein tyrosine phosphorylation, a universal indicator of capacitation.

Example 2

Inhibition of Capacitation-associated Tyrosine Phophorylation Signaling in Rat Sperm by Epididymal Protein Crisp-1

In mammals, development of fertilizing ability and progressive motility by sperm, the process of post-testicular maturation, begin as sperm are moved through the male reproductive tract and are completed when sperm are deposited in the female reproductive tract and undergo capacitation.

In the male post-testicular duct system, sperm acquire new proteins and glycoproteins on their surfaces and undergo numerous biochemical changes during their passage through the ducts that make them capable of vigorous, directed movement and able to fertilize an egg (*Yanagimachi R. Mammalian Fertilization. The Physiology of Reproduction* 1994: 186-317). Crisp-1 (DE, AEG) is a glycoprotein couplet (comprised of protein D and protein E, hereinafter referred to collectively as Crisp-1) that is secreted by the epididymal epithelium (Brooks and Higgins, *Journal of Reproduction & Fertility* 1980; 59: 363-375; Moore et al, *Molecular Reproduction & Development* 1994; 37: 181-194) and associates with the sperm surface (Rochwerger and Cuasnicu, *Molecular Reproduction & Development* 1992; 31: 3441; Xu et al, *Mol Reprod Dev* 1997; 46: 377-382.). A portion of the Crisp-1 on the sperm surface, in particular Protein E, is proteolytically-processed (Roberts et al, *Biology of Reproduction* 2002; 67: 525-533). Crisp-1 is one of many epididymis-secreted proteins that associate with sperm (Faye et al, *Biol Reprod* 1980, 23: 423-432; Kohane et al, *Biol Reprod* 1980, 23: 737-742; Moore, *J Exp Zool* 1981, 215: 77-85 (1981); Wong and Tsang, *Biol Reprod* 1982, 27: 1239-1246; Tezon et al, *Biol Reprod* 1985, 32: 591-597; Iusem et al, *Biol Reprod* 1989, 40: 307-316; Vreeburg et al., *Bull Assoc Anat (Nancy)* 1991, 75: 171-173; Rankin et al., *Biology of Reproduction* 1992, 46: 747-766; Boue et al, *Biol Reprod* 1996, 54: 1009-1017). The mechanism(s) of the interaction (e.g., covalent bonds, charge effects, hydrophobic bonds) between the sperm plasma membrane and extracellular epididymal molecules is unknown, but is likely to be varied. In contrast seminal vesicle secretions that are known to participate in capacitation in mice (Huang et al., *Biol Reprod* 2000, 63: 1562-1566 (2000); Huang et al., *Biochem J* 1999, 343 Pt 1: 241-248; Luo et al, *J Biol Chem* 2001 276: 6913-6921) and bulls (Huang et al, *Biol Reprod* 2000, 63: 1562-1566 (2000); Huang et al, *Biochem J* 1999, 343 Pt 1: 241-248; Luo et al., *J Biol Chem* 2001, 276: 6913-6921) are added to the cell surfaces after ejaculation by binding to sperm plasma membrane phospholipid head groups. In rats there is evidence that seminal vesicle proteins are added to the sperm surface (Manco and Abrescia, *Gamete Res* 1988, 21: 71-84; Manco et al., *Eur J Cell Biol* 1988, 47: 270-274), possibly by transglutaminase activity in semen (Paonessa et al., *Science* 1984, 226: 852-855), and it has been reported also that a prostate-derived protein binds to rat spermatozoa (Sansone and Abrescia, *J Exp Zool* 1991, 259: 379-385). Thus, addition of proteins and glycoproteins derived from different parts of the duct to sperm surfaces occurs throughout the male excurrent duct system.

Under normal conditions ejaculated sperm are unable to fertilize an egg until they have resided in the female tract for a number of hours (the time varies from species to species (Bedford, *Biol Reprod* 1970, 2: *Suppl* 2:128-158; Davis, *Proc Natl Acad Sci USA* 1981, 78: 7560-7564), and have undergone capacitation. Capacitation was independently, and virtually simultaneously, described in two laboratories (Austin, *Australian Journal of Scientific Research, B* 1951, 4: 581-589; Chang, *Nature* 1951, 168: 697) as the time required for sperm to penetrate an egg after having been deposited in the female reproductive tract. Residence in the female tract is required for capacitation in vivo, resulting in the acquisition of hyperactivated motility in many, but not all species; the loss or changes in some constituents of the plasma membrane, including proteins and glycoproteins and in the acquisition of the ability to undergo the acrosome reaction.

During the more than half century since its discovery, capacitation has been the subject of intense investigation, particularly since it is possible to capacitate sperm in vitro and use them to fertilize an egg. Common themes about what happens during capacitation are beginning to emerge. In all species that have been examined, it is necessary for cholesterol to be removed from the membrane, which can be accomplished in vitro by incubating sperm in a medium containing serum albumin (Davis, *Proc Soc Exp Biol Med* 1976, 151: 240-243; Davis et al., *Proc Natl Acad Sci USA* 1980, 77: 1546-1550) or other cholesterol-binding agents such as cyclodextrins (Choi and Toyoda, *Biol Reprod* 1998, 59: 1328-1333; Visconti et al., *Biol Reprod* 1999, 61: 76-84). Cholesterol removal results in a cAMP-dependent tyrosine phosphorylation of a number of proteins, both in the sperm plasma membrane and in intracellular structures such as the axoneme and fibrous sheath. Initiation and completion of capacitation is absolutely dependent on extracellular $Ca^{++}$ and $HCO_3^-$, in addition to a cholesterol sequestering agent.

In this example we report the results of experiments designed to elucidate the conditions required for in vitro capacitation of rat spermatozoa and the effects of Crisp-1, an epididymal secretory protein, on capacitation. We demonstrate that protein tyrosine phosphorylation, a hallmark of capacitation in other species' sperm, occurs during five hours of in vitro incubation and that this phosphorylation is dependent upon cAMP. $HCO_3^-$, $Ca^{++}$, and the removal of cholesterol from the membrane. We also show that Crisp-1, added to the sperm surface in the epididymis in vivo, is lost during capacitation and that addition of exogenous Crisp-1 to the incubation medium inhibits tyrosine phosphorylation in a dose dependent manner, and thus inhibits capacitation and ultimately the acrosome reaction. We further show that the inhibition of capacitation by Crisp-1 is upstream of the production of cAMP by the sperm.

Materials and Methods

Chemicals and Reagents: Anti-Phosphotyrosine (4G10) monoclonal IgG conjugated to horseradish peroxidase (HRP)

was purchased from Upstate Biotechnology Inc. (Lake Placid, N.Y.). ALEXA FLUOR 488 goat anti-rabbit IgG, AMPLEX Red Cholesterol Assay Kit and Slow-Fade were purchased from Molecular Probes (Eugene, Oreg.). Cold water fish skin gelatin (40% solution) was purchased from Electron Microscopy Sciences (Washington, Pa.). SUPER SIGNAL West Pico Chemiluminescent Substrate was purchased from Pierce Chemical Co. (Rockford, Ill.). ALBUMAX I lipid-rich bovine serum albumin (BSA) was purchased from Gibco BRL (Grand Island, N.Y.). Original and modified BWW were purchased from Irvine Scientific (Santa Ana, Calif.). All other chemicals and reagents were purchased from Sigma-Aldrich (St. Louis, Mo.). Generation of the CAP-A anti-peptide polyclonal antibody and the 4E9 monoclonal antibody have been previously described (Moore et al., *Molecular Reproduction & Development* 1994, 37:181-194; Roberts et al., *Biology of Reproduction* 2002, 67: 525-533).

Media: The base media used for collection and experimental incubation of sperm was original formula BWW medium (Biggers et al, *Methods in Mammalian Embryology* 1971, 86-116). BWW minus calcium or bicarbonate was prepared according to the recipe reported by Biggers, et. al. (1971) (Biggers et al, *Methods in Mammalian Embryology* 1971, 86-116). Sperm were capacitated in BWW with 15 mg/ml ALBUMAX I lipid-rich BSA, unless otherwise noted. Other cholesterol acceptor molecules included Fraction V BSA and methyl-β-cyclodextrin, and were added to BWW in some experiments.

Sperm Collection and Preparation: Spague-Dawley male retired breeder rats were euthanized by $CO_2$ asphyxiation and epididymes were surgically removed. Radial slits were made in each of the cauda epididymes followed by a 5 minute incubation in 1 ml of BWW buffered with 21 mM HEPES on an orbital shaker to facilitate the swim out of sperm into the media. The sperm suspensions were placed in a 1.5 ml microcentrifuge tube, leaving behind the epididymes, and gently shaken by hand to ensure an even concentration of sperm. Sperm counts were performed using a hemacytometer. Aliquots of approximately $3.5 \times 10^6$ sperm were diluted into 0.5 ml of capacitation medium that was pre-equilibrated overnight at 37° C. in 5% $CO_2$. The incubation wells were overlayed with 0.5 ml of mineral oil and incubated for times indicated (in figure legends) at 37° C. in 5% $CO_2$. Subjective assessment of sperm motility showed minimal decreases during capacitation incubation. All animal experiments were approved by the Institutional Animal Care and Use Committee of the University of Minnesota.

SDS-PAGE and Western Blotting: Samples were prepared for SDS-PAGE analysis using a modification of the protocol described by Visconti et. al., (1995). Briefly, sperm were collected from under oil and centrifuged at 16,000×g in microcentrifuge tubes for 5 minutes immediately following the capacitation incubation. The sperm pellet was washed twice with 1 ml of phosphate buffered saline (PBS) and resuspended in 100 µl of 1× Laemmli sample buffer (*Laemmli. Nature* 1970, 227: 680-685). The samples were vortexed for 15 seconds, heated to 95° C. for 5 minutes and centrifuged at 16,000×g to remove insoluble material. Supernatants were transferred to new tubes, reduced by the addition of β-mercaptoethanol (to a final concentration of 2.5%) and heated again to 95° C. for 5 minutes. 20 µl of each sample, equivalent to $7 \times 10^5$ sperm, were subjected to polyacrylamide gel electrophoresis (PAGE) on tris-glycine gels (7.5%, 12% or 15%, depending on the experiment). Proteins were transferred to Immobilon P membrane (Millipore, Bedford, Mass.) at 100 volts for 1 hour at 4° C.

For detection of tyrosine-phosphorylated proteins, blots were blocked with 6.5% fish skin gelatin in TBS-T (Tris Buffererd Saline with 0.1% Tween 20) for 30 minutes followed by incubation with anti-phosphotyrosine-HRP antibody (1:15,000), in blocking solution, for 1 hour at room temperature. The blots were washed with TBS-T, followed by incubation with HRP substrate (Super Signal West Pico) for 5 minutes. Blots were exposed to X-ray film for 5 to 30 seconds. Western blot detection of the protein D and E forms of Crisp-1 with anti-peptide antibody CAP-A and monoclonal antibody 4E9 were done as previously described (Moore et al., *Molecular Reproduction & Development* 1994, 37: 181-194; Roberts et al., *Biology of Reproduction* 2002, 67: 525-533.).

Immunocytochemistry: Sperm were stained immunocytochemically with anti-peptide antibody CAP-A and monoclonal antibody 4E9 essentially as previously described (Moore et al., *Molecular Reproduction & Development* 1994; 37: 181-194). Briefly, sperm were washed 3× in BWW to remove media, fixed with Bouin's fixative for 30 minutes and washed extensively with PBS. Cells were blocked for 30 minutes with 1% BSA/PBS and antibodies were added for an hour incubation at room temperature. The anti-peptide antibody CAP-A was used at a dilution of 1:200 while mAb 4E9 was used at 1:1000. Sperm were washed 3× with PBS and Alexa-Fluor 488 anti-rabbit antibody was added to the CAP-A tubes while anti-mouse—FITC was added to the 4E9 tubes. After incubation for 1 hour in Alexa-Fluor second antibody at room temperature, cells were washed with PBS mounted on slides in Slow-Fade® and viewed using a Nikon fluorescent microscope.

Cholesterol Assay: Total lipids were extracted from BWW containing MBCD after incubation with sperm essentially as described by Bligh and Dyer (Bligh and Dyer, *Canadian Journal of Biochemistry and Physiology* 1959, 37: 911-917). Briefly, after incubating sperm with BWW/MBCD, sperm were removed by centrifugation and 0.8 ml of supernatant was recovered. Chloroform and methanol were added to the supernatant, with vortexing, to a final ratio of chloroform to methanol to aqueous supernatant of 2:2:1.8. After vigorous vortexing, the final mixture was centrifuged for 5 minutes at 600×g and one ml of the organic (lower) phase was removed to a new tube. The lipids in the organic phase were dried under a stream of desiccated nitrogen and stored at −20° C.

Cholesterol was measured in the extracted lipid samples using the Amplex Red Cholesterol Assay Kit, according to the manufacturers instructions. Briefly, dried lipid samples were resuspended in 50 µl of reaction buffer and mixed 1:1 with working solution containing 300 µM Amplex Red reagent, 2 U/ml horseradish peroxidase, 2 U/ml cholesterol oxidase and 2 U/ml cholesterol esterase in wells of a 96-well microtiter plate. A standard curve was prepared using the cholesterol reference standard provided with the kit. All samples were incubated for 2 hrs at 37° C. Fluorescence of reaction product was measured at various time points in a FL600 Microplate Reader (BIOTEK Instruments, Inc., Winooski, Vt.) with an excitation filter of 530 nm and an emission filter of 590 nm.

Acrosome reaction and staining: The acrosome reaction and assessment of acrosomal status was performed essentially as described by Bendahmane et al. (Bendahmane et al., *Arch Biochem Biophys* 2002, 404: 38-47). Following incubation under capacitating or non-capacitating conditions for 30 minutes, progesterone (P4), dissolved in DMSO, was added to a final concentration of 1 µM. After an additional 30 minutes of incubation, sperm were fixed in 4% paraformaldehyde, washed and dried on slides. To visualize the acrosome, the sperm were stained with 0.22% Coomassie blue G-250 solution for 2 minutes, rinsed with distilled water and allowed to air dry. Slides were coverslipped using Permount mounting media and observed under a Nikon brightfield microscope at a magnification of 600×. For each condition within an experiment, 500 cells were assessed for acrosomal status.

Statistical Analysis: All experiments reported in the manuscript were repeated a minimum of three times. Raw data from the acrosome reaction experiments were subjected to the Tukey analysis for determination of statistically significant differences (P<0.05) between pairs of all treatment groups.

Results

Initial studies were carried out to characterize the dependence of rat sperm capacitation on the presence of a cholesterol binding molecule, $Ca^{++}$ and $HCO_3^-$; the three components shown to be requirements of capacitation in most other species. Capacitation conditions for rat sperm were tested using tyrosine phosphorylation of sperm proteins as an indication of the extent of the capacitation process. FIG. 2A demonstrates, by western blot with an antibody against phosphotyrosine, the dependence of capacitation on incubation with a lipid-accepting molecule, in this experiment bovine serum albumin (BSA). In the presence of 15 mg/ml lipid rich BSA, protein tyrosine phosphorylation on sperm proteins increased over 5 hours of incubation. Cholesterol was determined to be the lipid responsible for capacitation since incubation with exogenous cholesterol sulfate inhibited protein tyrosine phosphorylation (FIG. 2B).

Initial capacitation experiments were carried out in solution of a 15 mg/ml lipid-rich BSA (Gibco-BRL), a concentration of BSA routinely used in our BWW solution for in vitro fertilization. Because most capacitation experiments are conducted using fraction V BSA, we compared the efficacy of using lipid-rich or fraction V BSA at various concentrations. FIG. 3A demonstrates that lipid-rich BSA was superior to fraction V for inducing tyrosine phosphorylation in rat sperm at all concentrations investigated. In fact, incubation of sperm with fraction V BSA gave very low levels of tyrosine phosphorylation in rat sperm. When the same comparison was performed using mouse sperm, where fraction V BSA is routinely used, the efficacy of tyrosine phosphorylation was the same (FIG. 3B). These results suggest that different BSA preparations have different effects on sperm depending on the species. The basis for this difference is not clear.

The dependence of rat sperm capacitation on exogenous $Ca^{++}$ is shown in FIG. 4. Incubation in the absence of exogenously added $Ca^{++}$ for 4 hours was accompanied by minimal tyrosine phosphorylation compared to sperm incubated in the presence of 1.7 mM $Ca^{++}$. The level of tyrosine phosphorylation in the absence of exogenous $Ca^{++}$ was higher than that seen in the absence of BSA, which may be attributable to trace amounts of $Ca^{++}$ in the medium or to the availability of $Ca^{++}$ from intracellular sources. Likewise, capacitation was shown to be dependent on the presence of bicarbonate ion in the medium by assessing protein tyrosine phosphorylation in the presence and absence of $HCO_3^-$ (FIG. 5). Solutions in this experiment were buffered with HEPES buffer to insure that the requirement of bicarbonate was not simply due to its buffering capacity in the medium.

To examine the relationship between cholesterol removal from the sperm plasma membrane and the protein tyrosine phosphorylation events associated with capacitation, sperm were incubated with two doses of the cholesterol-binding molecule methyl-β-cyclodextran (MBCD). During incubation with MBCD, cholesterol was removed from the sperm in a dose-dependent fashion. MBCD at 2 mM removed twice as much cholesterol as 1 mM MBCD (FIG. 6A). When protein tyrosine phosphorylation was measured, phosphorylation in 2 mM MBCD was increased in both kinetics and total amount over that observed with 1 mM MBCD (FIG. 6B). Protein tyrosine phosphorylation lagged behind the removal of cholesterol from the sperm plasma membrane, as indicated by the fact that cholesterol removal was at a plateau within 30 minutes with 1 mM MBCD (FIG. 6A) yet no increase in phosphorylation was observed until 2 hours (FIG. 6B). These results indicated that protein tyrosine phosphorylation is dependent on cholesterol removal in a dose dependent fashion, but that the kinetics of cholesterol removal is not rate limiting to the phosphorylation process.

The removal of cholesterol from cell membranes has been shown to affect the organization of lipid micro-domains, or rafts, which in turn can affect signaling events in the cell (Simons, *Nat Rev Mol Cell Biol* 2000, 1: 31-39). To determine if the removal of cholesterol from rat epididymal sperm might be associated with changes in lipid rafts, sperm were stained with the β subunit of cholera toxin (βCT), which binds to the ganglioside $GM_1$ (a lipid known to be present in many lipid rafts) before and after cholesterol removal. Rat epididymal sperm were incubated in BWW with or without BSA or MBCD to facilitate the removal of cholesterol from the sperm plasma membrane. After 5 hours the sperm were fixed and stained with a fluorescent-tagged β-subunit of cholera toxin, which binds to the sugar moiety of $GM_1$. In control sperm at time zero or after 5 hours in BWW only, $GM_1$ staining is tightly confined to the post-acrosomal and head cap regions of the sperm. After removal of cholesterol by BSA or MBCD, $GM_1$ staining begins to diffuse over the equatorial region and acrosome, and increased staining is seen on the sperm tail. Immediately after isolation of sperm from the rat epididymis the sperm show very specific staining with βCT over the equatorial segment and the head cap region. This staining pattern remained constant after 5 hours of incubation in BWW devoid of a cholesterol-binding molecule. However, after 5 hours of incubation with 15 mg/ml BSA or 1 mM MBCD, βCT staining became diffuse over the entire sperm head and became visible on the sperm tail. Virtually all of the sperm observed (>99%) underwent this redistribution. This result indicates that lipid microdomains on sperm are disrupted by removal of cholesterol, and raft components, such as $GM_1$, are redistributed on the surface of the sperm. This redistribution correlates with sperm capacitation, implicating raft-associated signaling events in the capacitation process.

Crisp-1 is a sperm maturation protein secreted in two forms, proteins D and E (Roberts et al., *Biology of Reproduction* 2002, 67: 525-533., Cameo and Blaquier, *Journal of Endocrinology* 1976, 69: 47-55; Xu and Hamilton, *Mol Reprod Dev* 1996, 43: 347-357) by the epididymal epithelium, both of which become bound to the sperm surface during epididymal transit (Moore et al., *Molecular Reproduction & Development* 1994, 37: 181-194., Brooks and Tiver, *Journal of Reproduction & Fertility* 1983, 69: 651-657). Studies have shown that the majority of Crisp-1 is lost from sperm during incubation after ejaculation or after incubation of sperm isolated from the epididymis (Tubbs et al., *J Androl* 2002, 23: 512-521). Staining of the protein D and E forms of Crisp1 by anti-peptide antibody CAP-A and monoclonal antibody 4E9 in the presence or absence of MBCD reveals that CAP-A binds to both the D and E forms of Crisp-1 and localizes to the entire surface of the sperm. With time the staining of sperm with CAP-A becomes less intense in both the absence and, even more so, in the presence of MBCD. The intensity of staining with antibody 4E9, which recognizes only the E form of Crisp-1, does not change with time in BWW and decreases only marginally when the sperm are incubated for 4 hours with MBCD. Staining, with antibodies that differentiate the binding of the protein D and E form of Crisp-1, demonstrates that the majority of the protein D and E forms of Crisp-1 is lost during capacitation incubation, with or without a cholesterol binding agent. However, the protein E form of Crisp-1 remains confined to the tail of the sperm without detectable loss or redistribution during the capacitation process.

Since the loss of the protein D form of Crisp-1 occurs during the time frame of sperm capacitation, it is possible that the presence of exogenous Crisp-1 may inhibit the capacitation process. FIG. 7A shows the effect on protein tyrosine phosphorylation of incubating sperm under capacitating conditions in the presence of increasing concentrations of purified Crisp-1. At a dose of 400 µg/ml, Crisp-1 inhibits almost completely the protein tyrosine phosphorylation associated with capacitation. Re-probing of these western blots with anti-peptide antibody CAP-A, which recognizes all forms of the Crisp-1 proteins, showed that the endogenous D-form of Crisp-1 (protein D at 32 kDa) is lost from the sperm during capacitation and that exogenous protein D becomes associated with the sperm coincident with the inhibition of capacitation (FIG. 7B). When this western blot was probed with a monoclonal antibody 4E9, which recognizes only the E-form of Crisp-1 (protein E at ~28 kDa), the blot showed that protein E is not lost from the sperm surface during capacitation and no additional protein E associates with sperm during the incubation with exogenous Crisp-1 (FIG. 7C).

It has been recently reported that the protein E form of Crisp-1 is processed as it associates with sperm in the epididymis and that a portion of the protein D form of Crisp-1 may also be processed as it associates with sperm (Roberts et al., *Biology of Reproduction* 2002, 67: 525-533). Comparison of FIGS. 7B and 7C demonstrates the presence of a processed form of Crisp-1 that is not recognized by the 4E9 antibody. This observation suggests that the processed forms of Crisp-1 attach permanently to the sperm while the unprocessed form of protein D interacts dynamically with the sperm plasma membrane to reversibly prevent capacitation-associated tyrosine phosphorylation.

If the tyrosine phosphorylation events suppressed by Crisp-1 represent the suppression of capacitation, then Crisp-1 should also be able to inhibit the ability of the cells to undergo an induced acrosome reaction. To test this, rat sperm were capacitated for one hour with 15 mg/ml BSA in the presence or absence of 400 µg/ml Crisp-1 and the acrosome reaction induced with 1 µM progesterone (P4). FIG. 8 shows a significant increase ($P<0.05$) in the acrosome reaction in capacitated sperm after incubation with P4. This increase was completely suppressed by addition of exogenous Crisp-1. The suppression of the acrosome reaction by Crisp-1 was statistically significant ($P<0.05$). This result indicates that Crisp-1 is inhibiting capacitation in rat sperm.

The dynamic nature of the interaction between Crisp-1 (unprocessed form) and the sperm surface suggests that the inhibition of protein tyrosine phosphorylation by Crisp-1 may be reversible. To test this possibility, sperm were incubated under capacitating conditions in the presence 200 µg/ml Crisp-1 for 5 hours and then removed to capacitation media devoid of Crisp-1. As the data of FIG. 9A demonstrate, significant suppression of protein tyrosine phosphorylation was observed at 5 hours by Crisp-1. After 3 additional hours of incubation in the absence of Crisp-1, protein tyrosine phosphoryation had resumed and continued out to 24 hours. The resumption of phosphorylation activity correlates with the loss of Crisp-1 from the sperm (FIG. 9B).

Previous studies on the requirements for capacitation in mouse sperm have shown that $Ca^{++}$, $HCO_3^-$, and removal of cholesterol from the sperm plasma membrane are all required for the protein tyrosine phosphorylation events of capacitation (Visconti et al., *Development* 1995, 121: 1129-1137). However, the absence of any of these three could be compensated for by the addition of cAMP analogs, demonstrating that cAMP signaling in the sperm is intermediary to protein tyrosine phosphorylation (Visconti et al., *Development* 1995, 121: 1139-1150). FIG. 10 demonstrates that a similar signaling pathway exists for rat sperm. When sperm were incubated in the presence of the cAMP analog db-cAMP and the phophodiesterase inhibitor IBMX, protein tyrosine phosphorylation occurred in the absence of any of the three molecules required for capacitation (FIG. 10A). Furthermore, stimulation of the cAMP pathway by db-cAMP and IBMX also overcame the inhibition of capacitation caused by exogenous Crisp-1 (FIG. 10B). These results indicate that the signaling pathway leading to capacitation is similar between mouse and rat, and that Crisp-1 inhibits capacitation by intervening in an event upstream of the stimulation of cAMP production by the sperm.

Discussion

This study provides the first characterization of the requirements for capacitation of rat sperm using tyrosine-phosphorylation of sperm proteins as the indication that the capacitation signaling cascade has been activated. As with previous work in other laboratories, primarily using mouse sperm, we have shown that rat sperm capacitation requires the presence of a cholesterol-binding agent, such as BSA, calcium ion, and bicarbonate ion (Visconti et al., *Development* 1995, 121: 1129-1137; Visconti et al., *J Androl* 1998, 19: 242-248). Further, the action of all three of these required molecules likely leads to the production of cAMP, as evidenced by the ability of exogenous db-cAMP with the phosphodiesterase inhibitor IBMX to overcome the absence of BSA, $Ca^{++}$ or $HCO_3^-$, consistent with the results of studies of mouse sperm capacitation (Visconti et al., *Development* 1995, 121: 1129-1137).

Most, if not all, mammalian sperm require cholesterol removal from the plasma membrane in order for capacitation to occur. However, the mechanism by which cholesterol removal facilitates capacitation in sperm is not known. One likely possibility is that removal of cholesterol from lipid microdomains, or rafts, facilitates the movement of signaling molecules in the plasma membrane, allowing critical interactions that lead to the activation of adenylate cyclase and subsequent tyrosine phosphorylation of target proteins. Several recent studies have provided evidence for the existence of lipid rafts on mouse and guinea pig sperm (Travis et al., *Dev Biol* 2001, 240: 599-610; Trevino et al., *FEBS Lett* 2001, 509: 119-125.; Honda et al., *J Biol Chem* 2002, 277: 16976-16984). We demonstrate here that rat sperm contain discrete regions of staining for binding of cholera toxin β subunit, which binds to the ganglioside $GM_1$, a common lipid component of membrane rafts. Furthermore, the discrete localization of $GM_1$ is lost during cholesterol extraction with either BSA or MBCD, suggesting that molecules within the sperm plasma membrane begin to diffuse upon removal of cholesterol. A similar diffusion of lipids in the sperm plasma membrane has been reported in boar sperm during in vitro capacitation (Gadella et al., *J Cell Sci* 1995, 108 (Pt 3):935-946)).

Our data also show that the degree of tyrosine phosphorylation in rat sperm is dependent upon the extent of cholesterol extraction. The data of FIG. 6 demonstrate that doubling the amount of MBCD used to extract cholesterol from the sperm membrane increases the maximal degree of tyrosine phosphorylation at the 5 hour time point. Increasing MBCD also increases the kinetics of phosphorylation. Taken together these findings suggest that, if liberation of signaling molecules to move in the plasma membrane is the mechanism by which cholesterol extraction works, removing more cholesterol facilitates more interactions and with faster kinetics. However, it is also clear that removal of cholesterol under the conditions of our experiments is not rate limiting to subsequent tyrosine phosphorylation. Using 1 mM MBCD, extraction of cholesterol reached a plateau within 30 minutes, but an increase in tyrosine phosphorylation was not detected until 2 hours and is not maximal until 3 hours. The delay between cholesterol removal and tyrosine phosphorylation is consistent with a requirement for physical redistribution of signaling molecules within the plasma membrane.

The requirement for bicarbonate ion in rat sperm capacitation is consistent with a role for the bicarbonate-dependent soluble adenylate cyclase that has been implicated in the capacitation process in sperm from other mammalian species (Sinclair et al., *Mol Reprod Dev* 2000, 56: 6-11; Wuttke et al., *Jop* 2001, 2: 154-158; Flesch et al., *J Cell Sci* 2001, 114: 3543-3555). A previous study using boar sperm demonstrated that without bicarbonate ion in the media, cholesterol was not lost from the plasma membrane during incubation in the presence of BSA (Flesch et al., *J Cell Sci* 2001, 114: 3543-3555). The authors of this study proposed that the role of bicarbonate ion was to activate the bicarbonate-dependent adenylate cyclase, which in turn caused the cAMP-dependent activation of flipase, which was required for cholesterol removal from the plasma membrane. In the work presented here, the absence of bicarbonate was overcome by addition of cAMP analog and IBMX, consistent with a capacitation requirement for cAMP downstream of the requirement for bicarbonate ion. However, cholesterol removal from the membrane proceeded normally in the absence of bicarbonate ion, supporting a mechanism of capacitation where cAMP acts downstream of cholesterol removal from the membrane.

Both capacitation and the acrosome reaction are calcium ion dependent functions of mammalian sperm (Visconti et al., *J Reprod Immunol* 2002, 53: 133-150); Breitbart, *Mol Cell Endocrinol* 2002, 187: 139-144). Our results demonstrate that exogenous calcium is required for the tyrosine phosphorylation accompanying capacitation, consistent with this requirement shown in earlier studies for other mammalian species (Visconti et al., *Development* 1995, 121: 1129-1137; Dorval et al., *Biol Reprod* 2002, 67: 1538-1545). The specific calcium-dependent molecular events of capacitation have not been determined, but the ability to overcome the absence of calcium in the medium with exogenous cAMP analogs suggests that the calcium-dependent events in the sperm are upstream of the activation of adenylate cyclase.

In addition to the requirement for $Ca^{++}$, $HCO_3^-$, and a cholesterol-binding agent in capacitation, a requirement for the disassociation of Crisp-1 from the sperm membrane for capacitation to proceed in rat sperm has also been demonstrated. It has been demonstrated by immunocytochemistry that a portion of the Crisp-1 staining is lost from the sperm with incubation, primarily from the head region and by western blot analysis that it is the 32 kDa form of Crisp-1 that is lost from the sperm membrane (FIG. 7). The addition of exogenous Crisp-1 inhibits protein tyrosine phosphorylation in a reversible manner, suggesting that Crisp-1 interacts with a specific protein or lipid on the sperm surface, in a dynamic ligand-receptor fashion, and inhibits the capacitation process. Given this effect of Crisp-1 on rat sperm capacitation and the high concentration of Crisp-1 in epididymal fluid, it is likely that Crisp-1 acts as a capacitation inhibiting factor.

Crisp-1 was also shown to inhibit the P4 induced acrosome reaction, supporting the conclusion that Crisp-1 inhibits capacitation and that protein tyrosine phosphorylation is required for capacitation in the rat. The level of induced acrosome reaction is low compared with that seen in other species but is consistent with a previous report for rat sperm (Bendahmane et al., *Arch Biochem Biophys* 2002, 404: 38-47). The very high level of spontaneous acrosome reactions that occur in rat sperm with time during capacitation, over 75% by 3 hours, make it difficult to measure the induced acrosome reaction at extended time points where phosphorylation is more easily measured.

The mechanism by which Crisp-1 inhibits the progression of rat sperm to capacitation is unknown. However, potential mechanisms of action can be inferred from similarities of this protein to proteins of known function. The primary amino acid sequence of Crisp-1 is highly similar to that of many toxins, in particular the toxin helothermine produced by the lizard *Heloderma horridum* (Morrissette et al., *Biophysical Journal* 1995, 68: 2280-2288). Helothermine is known to act as an inhibitor of calcium flux through the ryanodine receptor, a regulated calcium channel in muscle cells (Morrissette et al., *Biophysical Journal* 1995, 68: 2280-2288). Since calcium is required for capacitation, Crisp-1 may prevent the uptake of needed calcium via channels in the sperm plasma membrane. Ryanodine receptors have been reported to be present in testicular germ cells and sperm, but their exact localization remains unclear (Gianni et al., Journal of Cell Biology 1995, 128: 893-904; Trevino et al., Zygote 1998, 6: 159-172). However, it is certainly plausible that Crisp-1 acts on the sperm by interacting with a ryanodine receptor or a ryanodine receptor-like channel in the sperm plasma membrane.

It appears that Crisp-1 is the only secretory protein of the epididymis to possess capacitation inhibitory activity. However, proteins or factors in secretions of the male reproductive tract with apparent capacitation inhibitory activity have been reported from several species (Huang et al., *Biol Reprod* 2000, 63: 1562-1566 (2000); Aonuma et al., *Chem Pharm Bull (Tokyo)* 1976, 24:907-911; Eng and Oliphant, *Biol Reprod* 1978, 19: 1083-1094; Kanwar et al., *Fertil Steril* 1979, 31: 321-327; Tomes et al., *Mol Hum Reprod* 1998, 4: 17-25). The mouse seminal vesicle autoantigen has been shown to inhibit protein tyrosine phosphorylation associated with sperm capacitation and human seminal plasma has been shown to contain a factor(s) with similar activity (Huang et al., *Biol Reprod* 2000, 63: 1562-1566 (2000); Tomes et al., *Mol Hum Reprod* 1998, 4: 17-25). Although little is known of the mechanism of capacitation suppression reported in seminal plasma and secretory proteins of the seminal vesicles, it appears that suppression of premature capacitation is an important function of fluids of the male excurrent reproductive tract.

In addition to the 32 kDa form of Crisp-1 that interacts in a reversible way with the sperm plasma membrane to inhibit capacitation, a second smaller molecular weight form is also found on sperm; this form is strongly attached and is not removed during incubation under capacitating conditions. It has been previously shown that both the D and E forms of Crisp-1 are processed (Roberts et al., *Biology of Reproduction* 2002, 67: 525-533). The processed E form of Crisp-1 is recognized by monoclonal antibody 4E9 and localizes to the sperm tail; its function there is unknown (Roberts et al., *Biology of Reproduction* 2002, 67: 525-533).

Crisp-1 has been implicated as playing a role in sperm-egg fusion. A number of studies in rat, mouse and human systems have shown that fusion of sperm to the plasma membrane of zona pellucida-free eggs is inhibited in the presence of Crisp-1 (Rochwerger et al., *Developmental Biology* 1992, 153: 83-90); Cohen et al., *Biol Reprod* 2000, 63: 462-468, Cohen et al., *Biol Reprod* 2001, 65: 1000-1005). Further, preincubation of zona pellucida-free eggs with Crisp-1, followed by immunocytochemistry with an antibody specific to Crisp-1, demonstrates specific binding sites for Crisp-1 on the surface of eggs (Rochwerger et al., *Developmental Biology* 1992, 153: 83-90). Taken together, these studies suggest that Crisp-1 can inhibit sperm-egg fusion and are consistent with the hypothesis that Crisp-1 is involved in sperm-egg fusion. However, there are no known fusogenic domains contained within the amino acid sequence of Crisp-1 and nothing in the predicted tertiary structure of the protein suggests a role in membrane fusion. Therefore, it is unlikely that Crisp-1 mediates the sperm-egg fusion event directly. Given the ability of Crisp-1 to block the signaling cascade leading to capacitation, as shown in the present example, a possible role for Crisp-1 in sperm-egg fusion may involve regulation of signaling events, particularly those associated with protein tyrosine phosphorylation. Processed Crisp-1 remaining on the sperm plasma membrane could interact with signaling molecules on the egg surface to initiate or otherwise regulate the fusion event.

The complete disclosures of all patents, patent applications including provisional patent applications, and publications, and electronically available material (e.g., GenBank amino acid and nucleotide sequence submissions) cited herein are incorporated by reference. The foregoing detailed description and examples have been provided for clarity of understanding only. No unnecessary limitations are to be understood therefrom. The invention is not limited to the exact details shown and described; many variations will be apparent to one skilled in the art and are intended to be included within the invention defined by the claims.

SEQUENCE LISTING FREE TEXT

SEQ ID NO: 1-7 are amino acid sequences.
SEQ ID NO: 8-14 are cDNA sequences.

What is claimed is:

1. A method of inhibiting sperm capacitation comprising contacting sperm that have not undergone capacitation with a cysteine-rich secretory protein (CRISP) polypeptide under capacitation conditions, wherein the CRISP polypeptide has at least 95% sequence identity to human CRISP-1 (SEQ ID NO: 1) and the CRISP polypeptide inhibits tyrosine phosphorviation of sperm proteins.

2. A method of inhibiting sperm capacitation comprising contacting sperm that have not undergone capacitation with a cysteine-rich secretory protein (CRISP) polypeptide under capacitating conditions, wherein the CRISP polypeptide is human CRISP-1 (SEQ ID NO:1).

3. A method of inhibiting sperm capacitation comprising contacting sperm with the human CRISP-1 polypeptide SEQ ID NO: 1.

* * * * *